US012605374B2

(12) United States Patent
Musso et al.

(10) Patent No.: US 12,605,374 B2
(45) Date of Patent: Apr. 21, 2026

(54) METHODS FOR DRUG SCREENING AND COMPOSITIONS USEFUL FOR THE INHIBITION OF CELL PROLIFERATION AND/OR CELL SURVIVAL

(71) Applicant: The Brigham and Women's Hospital, Inc., Boston, MA (US)

(72) Inventors: Gabriel Musso, Boston, MA (US); Calum A. Macrae, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 858 days.

(21) Appl. No.: 17/782,441

(22) PCT Filed: Nov. 30, 2020

(86) PCT No.: PCT/US2020/062569
§ 371 (c)(1),
(2) Date: Jun. 3, 2022

(87) PCT Pub. No.: WO2021/113170
PCT Pub. Date: Jun. 10, 2021

(65) Prior Publication Data

US 2023/0093878 A1 Mar. 30, 2023

Related U.S. Application Data

(60) Provisional application No. 62/944,864, filed on Dec. 6, 2019.

(51) Int. Cl.
*A61K 31/4709* (2006.01)
*A61K 31/5377* (2006.01)
*A61K 31/55* (2006.01)
*A61P 35/00* (2006.01)

(52) U.S. Cl.
CPC ...... *A61K 31/4709* (2013.01); *A61K 31/5377* (2013.01); *A61K 31/55* (2013.01); *A61P 35/00* (2018.01)

(58) Field of Classification Search
CPC ............ A61K 31/4709; A61K 31/5377; A61K 31/55; A61P 35/00; A61P 43/00
See application file for complete search history.

(56) References Cited

U.S. PATENT DOCUMENTS

| | | | |
|---|---|---|---|
| 9,267,122 | B2 | 2/2016 | DiPaolo et al. |
| 2003/0219849 | A1 | 11/2003 | Tsao et al. |

FOREIGN PATENT DOCUMENTS

| | | | |
|---|---|---|---|
| WO | 2021113170 | A1 | 6/2021 |

OTHER PUBLICATIONS

Krishnam et al Alzheimer's & Dementia: Translational Research & Clinical Interventions 2018, 4, 89-102 (Year: 2018).*
Cho et al Mol Cells 2017, 40(11), 805-813 (Year: 2017).*
Adams et al., Compound classification using image-based cellular phenotypes, 2006, pp. 440-468, vol. 414, In Methods in enzymology, Academic Press.
Aitken et al., The gene encoding the phosphatidylinositol transfer protein is essential for cell growth, 1990, pp. 4711-4717 (7 pages), vol. 265, Issue No. 8, Journal of Biological Chemistry.
Bankaitis et al., The Sec14 superfamily and mechanisms for crosstalk between lipid metabolism and lipid signaling, 2010, pp. 150-160 (22 pages), vol. 35, Issue No. 3, Trends in biochemical sciences.
Barretina et al., The Cancer Cell Line Encyclopedia enables predictive modelling of anticancer drug sensitivity, 2012, pp. 603-607 (13 pages), vol. 483, Issue No. 7391, Nature.
Bornot et al., The role of historical bioactivity data in the deconvolution of phenotypic screens, 2014, pp. 696-706 (11 pages), vol. 19, Issue No. 5, SLAS Discovery.
Bray et al., Cell Painting, a high-content image-based assay for morphological profiling using multiplexed fluorescent dyes, 2016, pp. 1757-1774 (43 pages), vol. 11, Issue No. 9 Nature protocols.
Bray et al., A dataset of images and morphological profiles of 30 000 small-molecule treatments using the Cell Painting assay, 2017, 5 pages, vol. 6, Issue No. 12, Document No. giw014, Gigascience.
Breiman, Leo, Random forests, 2001, pp. 5-32 (28 pages), vol. 45, Issue No. 1, Machine learning.
Burns et al., Caenorhabditis elegans is a useful model for anthelmintic discovery, 2015, pp. 1-11 (11 pages), vol. 6, Issue No. 1, Nature Communications.
Chung et al., The varied roles of nuclear receptors during vertebrate embryonic development, 2003, 7 pages, signaling vol. 1, Issue No. 1, Document No. nrs-01007, Nuclear receptor.
Cocco et al., Phosphoinositide-specific phospholipase C in health and disease, 2015, pp. 1853-1860 (8 pages), vol. 56, Issue No. 10, Journal of lipid research.
Enright et al., An efficient algorithm for large-scale detection of protein families, 2002, pp. 1575-1584 (10 pages), Nucleic acids research vol. 30, Issue No. 7.
Foley et al., Quinoline antimalarials: mechanisms of action and resistance and prospects for new agents, 1998, pp. 55-87, vol. 79, Issue No. 1, Pharmacology & therapeutics.
Futamura et al., Morphobase, an encyclopedic cell morphology database, and its use for drug target identification, 2012, pp. 1620-1630 (11 pages), vol. 19, Issue No. 12, Chemistry & biology.
Giaever et al., Functional profiling of the *Saccharomyces cerevisiae* genome, 2002, pp. 387-391, vol. 418, Issue No. 6896, nature.

(Continued)

*Primary Examiner* — Yevgeny Valenrod
(74) *Attorney, Agent, or Firm* — QUARLES & BRADY LLP

(57) ABSTRACT

The present disclosure relates to the field of drug discovery and therapeutics, including systems and methods to predict drug function, to classify or prioritize drugs based on predicted function, and to test known and novel compounds for function in a vertebrate system. The present disclosure also relates to compounds identified using the disclosed systems and methods, the novel mechanisms of action of the compounds, and applications of the compounds as therapeutics, e.g., as cancer therapeutics.

16 Claims, 24 Drawing Sheets

(56) References Cited

OTHER PUBLICATIONS

Giaever et al., Chemogenomic profiling: identifying the functional interactions of small molecules in yeast, 2004, pp. 793-798 (6 pages), vol. 101, Issue No. 3, Proceedings of the National Academy of Sciences.
Griffin et al., Clemizole and modulators of serotonin signalling suppress seizures in Dravet syndrome, 2017, pp. 669-683 (15 pages), vol. 140, Issue No. 3 Brain.
Haggard et al., Transcriptomic and phenotypic profiling in developing zebrafish exposed to thyroid hormone receptor agonists, 2018, pp. 80-93 (28 pages), vol. 77, Reproductive Toxicology.
Hann et al., Finding the sweet spot: the role of nature and nurture in medicinal chemistry, 2012, pp. 355-365 (11 pages), vol. 11, Issue No. 5, Nature reviews Drug discovery.
Hillenmeyer et al., The chemical genomic portrait of yeast: uncovering a phenotype for all genes, 2008, pp. 362-365 (8 pages), vol. 320, Issue No. 5874, Science.
Hughes et al., Principles of early drug discovery, 2011, pp. 1239-1249 (11 pages), vol. 162, Issue No. 6, British journal of Pharmacology.
Hui, David Y., Phospholipase A2 enzymes in metabolic and cardiovascular diseases, 2012, pp. 235-240 (11 pages), vol. 23, Issue No. 3, Current opinion in lipidology.
Johannessen et al., Integrating phenotypic small-molecule profiling and human genetics: the next phase in drug discovery, 2015, pp. 16-23 (19 pages), vol. 31, Issue No. 1, Trends in Genetics.
Keiser et al., Relating protein pharmacology by ligand chemistry, 2007, vol. 25, Issue No. 2 pp. 197-206 (11 pages), Nature biotechnology.
Kim et al., PubChem substance and compound databases, 2016, pp. D1202-D1213 (12 pages), vol. 44, Article No. D1, Nucleic acids research.
Kutchukian et al., Chemistry informer libraries: a chemoinformatics enabled approach to evaluate and advance synthetic methods, 2016, pp. 2604-2613 (10 pages), vol. 7, Issue No. 4, Chemical science.
Kutchukian et al., Iterative focused screening with biological fingerprints identifies selective Asc-1 inhibitors distinct from traditional high throughput screening, 2017, pp. 519-527 (18 pages), vol. 12, Issue No. 2, ACS Chemical Biology.
Kwok et al., A small-molecule screen in C. elegans yields a new calcium channel antagonist, 2006, pp. 91-95 (6 pages), vol. 441, Nature.
Ljosa et al., Comparison of methods for image-based profiling of cellular morphological responses to small-molecule treatment, 2013, pp. 1321-1329 (9 pages), Journal of biomolecular screening vol. 18, Issue No. 10.
Luciani et al., Dafadine inhibits DAF-9 t o promote dauer format ion and longevity of Caenorhabditis elegans, Dec. 2011, (64 pages) vol. 7, Nature Chemical Biology.
Mao et al., Synthesis and antituberculosis activity of novel mefloquine-isoxazole carboxylic esters as prodrugs, Nov. 26, 2009, pp. 1263-1268 (6 pages), Bioorganic & Medicinal Chemistry Letters.
Mason et al., Some pharmacological properties of piperazine, 1972, pp. 169-176 (8 pages), vol. 44, Issue No. 2, British Journal of Pharmacology.
Mathew et al., Using C. elegans forward and reverse genetics to identify new compounds with anthelmintic activity, 2016, 28 pages, vol. 10, Issue No. 10 Document No. e0005058, PLoS neglected tropical diseases.
Mendelsohn et al., The zebrafish embryo as a dynamic model of anoxia tolerance, 2008, pp. 1780-1788 (9 pages), vol. 237, Issue No. 7, Developmental dynamics: an official publication of the American Association of Anatomists.
Mervin et al., Understanding cytotoxicity and cytostaticity in a high-throughput screening collection, 2016, 18 pages, vol. 11, Issue No. 11, ACS chemical biology.
Mousley et al., The Sec14-superfamily and the regulatory interface between phospholipid metabolism and membrane trafficking, 2007, pp. 727-736 (19 pages), vol. 1771, Issue No. 6, Biochimica et Biophysica Acta (BBA)-Molecular and Cell Biology of Lipids.
Mousley et al., Sec14 like PITPs couple lipid metabolism with phosphoinositide synthesis to regulate Golgi functionality, 2012, pp. 271-287, Phosphoinositides II: The Diverse Biological Functions.
Musso et al., Novel cardiovascular gene functions revealed via systematic phenotype prediction in zebrafish, 2014, pp. 224-235 (12 pages), vol. 141, Issue No. 1, Development.
Nica et al., Zebrafish pit1 mutants lack three pituitary cell types and develop severe dwarfism, 2004, pp. 1196-1209 (14 pages), vol. 18, Issue No. 5, Molecular Endocrinology.
North et al., Prostaglandin E2 regulates vertebrate haematopoietic stem cell homeostasis, 2007, pp. 1007-1011 (14 pages), vol. 447, Issue No. 7147, Nature.
O'Boyle et al., Open Babel: An open chemical toolbox, 2011, pp. 1-14 (14 pages), vol. 3, Issue No. 1, Journal of Cheminformatics.
Paricharak et al., Analysis of iterative screening with stepwise compound selection based on Novartis in-house HTS data, 2016, pp. 1255-1264, vol. 11, Issue No. 5, ACS chemical biology.
Park et al., Phospholipase signalling networks in cancer, 2012, vol. 12, Issue No. 11, pp. 782-792 (12 pages), Nature Reviews Cancer.
Paul et al., How to improve R&D productivity: the pharmaceutical industry's grand challenge, 2010, pp. 203-214 (12 pages), Nature reviews Drug discovery vol. 9, Issue No. 3.
Paull et al., Display and analysis of patterns of differential activity of drugs against human tumor cell lines: development of mean graph and Compare algorithm, 1989, pp. 1088-1092, vol. 81, Issue No. 14, JNCI: Journal of the National Cancer Institute.
PCT International Search Report and Written Opinion, PCT/US2020/062569, mailed Mar. 12, 2021, 7 pages.
Peal et al., Small molecule screening in zebrafish, 2010, pp. 454-460, vol. 3, Issue No. 5, Journal of cardiovascular translational research.
Pierce et al., A unique and universal molecular barcode array, 2006, pp. 601-603, vol. 3, Issue No. 8, Nature methods.
Pinho et al., How mitochondrial dysfunction affects zebrafish development and cardiovascular function: an in vivo model for testing mitochondria-targeted drugs, 2013, pp. 1072-1090 (19 pages), vol. 169, Issue No. 5, British journal of pharmacology.
Polyakov et al., Enrichment analysis for discovering biological associations in phenotypic screens, 2014, pp. 377-386, vol. 54, Issue No. 2, Journal of Chemical Information and Modeling.
Raschi et al., hERG-related drug toxicity and models for predicting hERG liability and QT prolongation, 2009, pp. 1005-1021, vol. 5, Issue No. 9, Expert Opinion on Drug Metabolism & Toxicology.
Recanatini et al., QT prolongation through hERG K+ channel blockade: current knowledge and strategies for the early prediction during drug development, 2005, pp. 133-166, vol. 25, Issue No. 2, Medicinal research reviews.
Reisen et al., Linking phenotypes and modes of action through high-content screen fingerprints, 2015, pp. 415-427 (14 pages), vol. 13, Issue No. 7, Assay and drug development technologies.
Rihel et al., Behavioral screening for neuroactive drugs in zebrafish, 2012, pp. 373-385 (29 pages), vol. 72, Issue No. 3, Developmental neurobiology.
Riniker et al., Using information from historical high-throughput screens to predict active compounds, 2014, pp. 1880-1891, vol. 54, Issue No. 7, Journal of chemical information and modeling.
RohitKumar et al., Cell Cycle Arrest and Induction of Apoptosis in Colon Adenocarcinoma Cells by a DNA Intercalative Quinoline Derivative, 4-Morpholinopyrimido [4', 5': 4, 5] Selenolo (2, 3-b) Quinoline, 2015, pp. 525-543, vol. 34, Issue No. 8, Nucleosides, Nucleotides and Nucleic Acids.
RohitKumar et al., DNA intercalative 4-butylaminopyrimido [4', 5': 4, 5] thieno (2, 3-b) quinoline induces cell cycle arrest and apoptosis in leukemia cells, 2015, pp. 1121-1133, vol. 75, Issue No. 6, Cancer Chemotherapy and Pharmacology.
Rudge et al., Differential regulation of Saccharomyces cerevisiae phospholipase D in sporulation and Sec14-independent secretion, 2002, pp. 1353-1361 (10 pages), vol. 160, Issue No. 4 Genetics.
Shannon et al., Cytoscape: a software environment for integrated models of biomolecular interaction networks, 2003, pp. 2498-2504 (8 pages), vol. 13, Issue No. 11, Genome research.

(56) References Cited

OTHER PUBLICATIONS

Shelat et al., The interdependence between screening methods and screening libraries, 2007, pp. 244-251, vol. 11, Issue No. 3, Current opinion in chemical biology.
Sheridan et al., Similarity to molecules in the training set is a good discriminator for prediction accuracy in QSAR, 2004, pp. 1912-1928, vol. 44, Issue No. 6, Journal of chemical information and computer sciences.
Sing et al., ROCR: visualizing classifier performance in R, 2005, pp. 3940-3941 (2 pages), Bioinformatics vol. 21, Issue No. 20.
Smith et al., Highly-multiplexed barcode sequencing: an efficient method for parallel analysis of pooled samples, 2010, 7 pages, vol. 38, Issue No. 13, Document No. e142, Nucleic acids research.
Stackley et al., Bioenergetic profiling of zebrafish embryonic development, 2011, 12 pages, vol. 6, Issue No. 9, Document No. e25652, PloS one.
Subramanian et al., Gene set enrichment analysis: a knowledge-based approach for interpreting genome-wide expression profiles, 2005, pp. 15545-15550 (6 pages), vol. 102, Issue No. 43, Proceedings of the National Academy of Sciences.
Sun et al., Efficient identification of novel leads by dynamic focused screening: PDK1 case study, 2010, pp. 16-26 (12 pages), vol. 13, Issue No. 1, Combinatorial Chemistry & High Throughput Screening.
Sundaramurthy et al., Integration of chemical and RNAi multiparametric profiles identifies triggers of intracellular mycobacterial killing, 2013, pp. 129-142 (14 pages), vol. 13, Issue No. 2, Cell host & microbe.
Svetnik et al., Random forest: a classification and regression tool for compound classification and QSAR modeling, 2003, pp. 1947-1958, vol. 43, Issue No. 6, Journal of chemical information and computer sciences.
Swinney et al., How were new medicines discovered?, 2011, pp. 507-519 (13 pages), vol. 10, Issue No. 7, Nature reviews Drug discovery.
Viswanadhan et al., Atomic physicochemical parameters for three dimensional structure directed quantitative structure-activity relationships. 4. Additional parameters for hydrophobic and dispersive interactions and their application for an automated superposition of certain naturally occurring nucleoside antibiotics, 1989, pp. 163-172, vol. 29, Issue No. 3, Journal of chemical information and computer sciences.
Wallace et al., Compound prioritization methods increase rates of chemical probe discovery in model organisms, 2011, pp. 1273-1283 (11 pages), vol. 18, Issue No. 10, Chemistry & biology.
Wang et al., PubChem bioassay: 2014 update, 2014, pp. D1075-D1082 (8 pages), vol. 42, Issue No. D1, Nucleic acids research.
Wassermann et al., Efficient search of chemical space: Navigating from fragments to structurally diverse chemotypes, 2013, pp. 8879-8891, vol. 56, Issue No. 21, Journal of Medicinal Chemistry.
Wassermann et al., The opportunities of mining historical and collective data in drug discovery, 2015, pp. 422-434, vol. 20, Issue No. 4, Drug Discovery Today.
Weinstein et al., An information-intensive approach to the molecular pharmacology of cancer, 1997, pp. 343-349 (7 pages), vol. 275, Issue No. 5298, Science.
Yu et al., BMP type I receptor inhibition reduces heterotopic ossification, 2008, pp. 1363-1369 (14 pages), vol. 14, Issue No. 12, Nature medicine.
Yu et al., Dorsomorphin inhibits BMP signals required for embryogenesis and iron metabolism, 2008, pp. 33-41 (21 pages), vol. 4, Issue No. 1, Nature chemical biology.
Zheng et al., Phenotypic screens as a renewed approach for drug discovery, 2013, pp. 1067-1073 (16 pages), vol. 18, Issue No. 21-22, Drug discovery today.

* cited by examiner

Positive Enrichment

Methyl Benzoate
28 / 29
$q < 0.001$

Methyl-piperidin-4-ylmethyl-amine
71 / 128
$q < 0.05$

4-Methyl phenetole
21 / 27
$q < 0.05$

Negative Enrichment 1,4 Dimethylpyrazole
9 / 71
$q < 0.01$

Phenycyclohexane
1 / 29
$q < 0.05$

FIG. 13
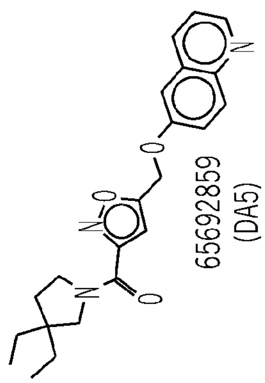
65692859
(DA5)
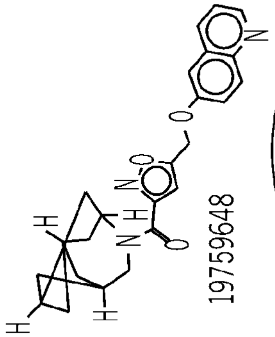
19759648
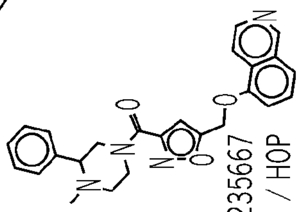
27235667
HIP / HOP
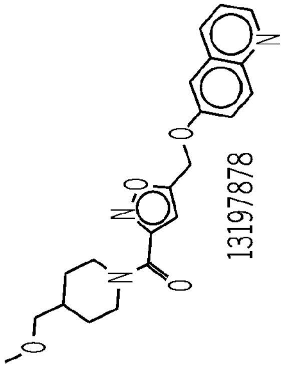
13197878
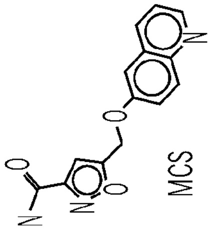
MCS
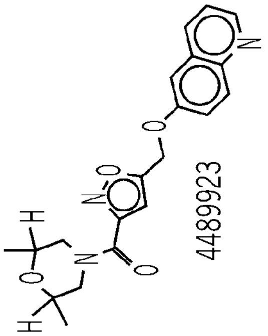
4489923
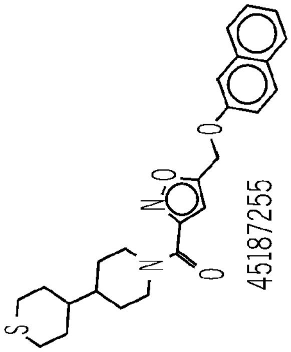
45187255
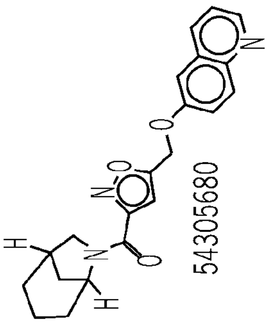
54305680
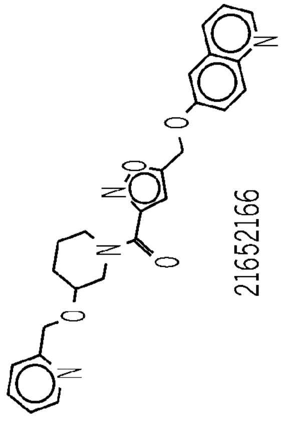
21652166

Ctrl 1
Ctrl 2
Ctrl 3
Ctrl 4
Ctrl 5
Ctrl 6
Ctrl 7
Ctrl 8
Ctrl 9
Ctrl 10
Ctrl 11
Ctrl 12

| Term | Cutoff | ActivityID | Num_Actives | Num_Inactives | AccInSet | InactInSet | p | q | Description |
|---|---|---|---|---|---|---|---|---|---|
| Cardiac | 0.8 | 720553 | 3260 | 336265 | 10 | 10 | 1.1024E-15 | 2.76563E-10 | QHTS For Inhibitors Of KCHN2 3.1: Mutant QHTS |
| Cardiac | 0.8 | 651702 | 2404 | 361030 | 9 | 16 | 4.38965E-14 | 1.10124E-08 | Flow Cytometric HTS Screening For Inhibitors Of Lytic Granule Exocytosis With MLPCN Compound Library |
| Cardiac | 0.8 | 720551 | 1267 | 341912 | 7 | 18 | 4.13738E-12 | 1.03796E-06 | QHTS For Inhibitors Of KCHN2 3.1: Wildtype QHTS |
| Cardiac | 0.8 | 624417 | 6432 | 321734 | 6 | 1 | 3.88178E-10 | 9.73834E-05 | qHTS of GLP-1 Receptor Inverse Agonists (Inhibition Mode) |
| Cardiac | 0.8 | 652054 | 9117 | 339862 | 8 | 13 | 3.1213E-08 | 0.007830489 | QHTS Of D3 Dopamine Receptor Antagonist: QHTS |
| Cardiac | 0.8 | 743279 | 17205 | 328767 | 9 | 11 | 1.77953E-07 | 0.044643705 | qHTS for Inhibitors of Inflammasome Signaling: IL-1-beta AlphaLISA Primary Screen |
| Cardiac Only | 0.8 | 652054 | 9117 | 339862 | 6 | 2 | 8.42946E-09 | 0.002114723 | QHTS Of D3 Dopamine Receptor Antagonis: QHTS |
| Cranial Edema | 0.6 | 651702 | 2404 | 361030 | 4 | 3 | 6.5523E-08 | 0.016437957 | Flow Cytometric HTS Screing For Inhibitors of Lytic Granule Exocytosis With MLPCN Coumpound Library |
| Dead | 0.8 | 588342 | 25159 | 304590 | 38 | 21 | 3.28491E-28 | 8.24095E-23 | qHTS profiling assay for firefly luciferase inhibitor/activator using purified enzyme and Km concentrations of substrate (counterscreen for miR-21 project) |
| Dead | 0.8 | 2314 | 37055 | 259390 | 48 | 22 | 1.99152E-27 | 4.99618E-22 | Cycloheximide Counterscreen For Small Molecule Inhibitors Of Shiga Toxin |
| Dead | 0.8 | 1814 | 21692 | 277104 | 38 | 31 | 1.94453E-25 | 4.8783E-20 | MLPCN Alpha-Synuclein 5'UTR-5'-UTR binding-activators |
| Dead | 0.8 | 687014 | 6840 | 363434 | 24 | 49 | 1.14194E-23 | 2.86483E-18 | Luminescence-based cell-based primary high throughput screening assay to identify activators of the DAF-12 from the parasite H.glycines (hgDAF-12). |
| Dead | 0.8 | 2315 | 26913 | 266718 | 36 | 29 | 6.58462E-21 | 1.6519E-15 | A QHTS For Small Molecule Inhibitors Of Shiga Toxin |
| Dead | 0.8 | 652126 | 3700 | 366574 | 16 | 57 | 2.85292E-17 | 7.1572E-12 | Luminescence-based cell-based primary high throughput screening assay to identify activators of the DAF-12 from the parasite S. stercoralis (ssDAF-12) |
| Dead | 0.8 | 652067 | 5354 | 364920 | 16 | 57 | 8.22851E-15 | 2.06431E-09 | Luminescence-based cell-based primary high throughput screening assay to identify activators of the DAF-12 from the parasite H.contortus (hcDAF-12) |
| Dead | 0.8 | 2796 | 7990 | 316867 | 18 | 49 | 2.95095E-14 | 7.40312E-09 | Luminescence-based primary cell-based high throughput screening assay to identify activators of the Aryl Hydrocarbon Receptor (AHR) |
| Dead | 0.8 | 434973 | 4906 | 326852 | 14 | 56 | 1.97484E-12 | 4.95434E-07 | uHTS Luminescent assay for identification of inhibitors of Sentrin-specific protease 7 (SENP7) |
| Dead | 0.8 | 2540 | 4122 | 326357 | 13 | 57 | 4.03678E-12 | 1.01272E-06 | HTS Luminescent assay for identification of inhibitors of Sentrin-specific protease 8 (SENP8) |
| Dead | 0.8 | 932 | 5134 | 190877 | 13 | 24 | 5.07728E-12 | 1.27375E-06 | Primary cell-based high throughput screening assay to measure STAT1 activation |
| Dead | 0.8 | 2599 | 5820 | 324659 | 14 | 56 | 1.94641E-11 | 4.88301E-06 | uHTS Luminescent assay for identification of inhibitors of Sentrin-specific protease 6 (SENP6) |
| Dead | 0.8 | 652104 | 7165 | 371527 | 13 | 46 | 6.63257E-11 | 1.66393E-05 | qHTS of TDP-43 Inhibitors |
| Dead | 0.8 | 1463 | 2576 | 251621 | 8 | 21 | 3.81584E-10 | 9.5729E-05 | Counterscreen QHTS For Inhibitors Of Tau Fibril Formation, Fluorescence Polarization |
| Dead | 0.8 | 743279 | 17205 | 328767 | 18 | 47 | 1.55779E-09 | 0.000390808 | qHTS for Inhibitors of Inflammasome Signaling: IL-1-beta AlphaLISA Primary Screen |

FIG. 17

| | | | | | | | | | |
|---|---|---|---|---|---|---|---|---|---|
| Dead | 0.8 | 485297 | 9143 | 301950 | 13 | 39 | 2.40541E-09 | 0.000603452 | QHTS Assay For Rab9 Promoter Activators |
| Dead | 0.8 | 602393 | 7048 | 338975 | 11 | 41 | 6.4629E-09 | 0.001621368 | Screen for inhibitors of the SWI/SNF chromation remodeling complex (esBAF) in mouse embryonic stem cells with Luciferase reporter assay Measured in Cell-Based System Using Plate Reader-2141- |
| Dead | 0.8 | 1460 | 5823 | 221865 | 8 | 17 | 1.26898E-07 | 0.031835207 | QHTS For Inhibitors Of Tau Fibril Formation, Thioflavin T Binding |
| Dead | 0.8 | 651644 | 751 | 354319 | 5 | 57 | 2.39745E-07 | 0.06014559 | qHTS Assay for Inhibitors of the HIV-1 protein Vpr |
| Dead | 0.8 | 504466 | 4174 | 306923 | 8 | 41 | 2.70678E-07 | 0.067905782 | qHTS screen for small molecules that induce genotoxicity in human embryonic kidney (HEK293T) cells expressing luciferase-tagged ELG1 |
| Dead | 0.8 | 1304 | 800 | 217316 | 5 | 33 | 2.91682E-07 | 0.073175106 | Primary cell-based high-throughout screening assay for potentiators or agonists of NYP-Y1 |
| Dead | 0.8 | 651820 | 11664 | 271341 | 11 | 29 | 3.96237E-07 | 0.099405099 | QHTS Assay For Inhibitors Of Hepatitis C Virus (HCV) |
| Dead 24th | 0.8 | 2314 | 37055 | 259390 | 25 | 6 | 8.6857E-18 | 2.17901E-12 | Cycloheximide Counterscreen For Small Molecule Inhibitors Of Shiga Toxin |
| Dead 24th | 0.8 | 2315 | 26913 | 266718 | 22 | 8 | 3.96068E-17 | 9.93628E-12 | A QHTS For Small Molecule Inhibitors Of Shiga Toxin |
| Dead 24th | 0.8 | 588342 | 25159 | 304590 | 18 | 7 | 2.10621E-15 | 5.2839E-10 | qHTS profiling assay for firefly luciferase inhibitor/activator using purified enzyme and Km concentrations of substrates (counterscreen for miR-21 project) |
| Dead 24th | 0.8 | 1814 | 21692 | 277104 | 19 | 12 | 1.29278E-14 | 3.24324E-09 | MLPCN Alpha-Synuclein 5'UTR-5'-UTR binding-activators |
| Dead 24th | 0.8 | 687014 | 6840 | 363434 | 13 | 21 | 1.81079E-14 | 4.54279E-09 | Luminescence-based cell-based primary high throughout screening assay to identify agonists of the DAF-12 from the parasite H. glycines (hgDAF-12) |
| Dead 24th | 0.8 | 2540 | 4122 | 326357 | 8 | 24 | 4.53074E-09 | 0.001136639 | HTS Luminescent assay for identification of inhibitors of Sentrin-specific protease 8 (SENP8) |
| Dead 24th | 0.8 | 485297 | 9143 | 301950 | 8 | 11 | 3.02223E-08 | 0.007581971 | QHTS Assay For Rab9 Promoter Activators |
| Dead 24th | 0.8 | 932 | 5134 | 190877 | 8 | 13 | 3.17699E-08 | 0.007970205 | Primary cell-based high throughput screening assay to measure STAT1 activation |
| Dead 24th | 0.8 | 2599 | 5820 | 324659 | 8 | 24 | 6.32669E-08 | 0.015871963 | uHTS Luminescent assay for identification of inhibitors of Sentrin-specific protease 6 (SENP6) |
| Dead 24th | 0.8 | 434973 | 4906 | 326852 | 7 | 25 | 3.57333E-07 | 0.089645167 | uHTS Luminescent assay for identification of inhibitors of Sentrin-specific protease 7 (SENP7) |
| Dead 48th | 0.8 | 2314 | 37055 | 259390 | 36 | 11 | 1.21809E-23 | 3.05586E-18 | Cycloheximide Counterscreen For Small Molecule Inhibitors Of Shiga Toxin |
| Dead 48th | 0.8 | 588342 | 25159 | 304590 | 28 | 11 | 3.54641E-23 | 8.89699E-18 | qHTS profiling assay for firefly luciferase inhibitor/activator using purified enzyme and Km concentrations of substrate (counterscreen for miR-21 project) |
| Dead 48th | 0.8 | 1814 | 21692 | 277104 | 28 | 18 | 9.13063E-21 | 2.29063E-15 | MLPCN Alpha-Synuclein 5'UTR-5'-UTR binding-activators |
| Dead 48th | 0.8 | 2315 | 26913 | 266718 | 29 | 15 | 4.29178E-20 | 1.07669E-14 | A QHTS For Small Molecule Inhibitors Of Shiga Toxin |
| Dead 48th | 0.8 | 687014 | 6840 | 363434 | 18 | 32 | 6.11153E-19 | 1.53322E-13 | Luminescence-based cell-based primary high throughput screening assay to identify agonists of the DAF-12 from the parasite S. stercoralis (ssDAF-12) |
| Dead 48th | 0.8 | 2796 | 7900 | 316867 | 18 | 28 | 1.49688E-17 | 3.75527E-12 | Luminescence-based cell-based primary high throughput screening assay to identify activators of the Aryl Hydrocarbon Receptor (AHR) |
| Dead 48th | 0.8 | 652126 | 3700 | 366574 | 12 | 38 | 8.08108E-14 | 2.0732E-08 | Luminescence-based cell-based primary high throughput screening assay to identify activators of the DAF-12 from the parasite S. stercoralis (ssDAF-12) |

FIG. 17, con't.

| | | | | | | | | | |
|---|---|---|---|---|---|---|---|---|---|
| Dead 48th | 0.8 | 434973 | 4906 | 326852 | 13 | 34 | 1.35137E-13 | 3.39021E-08 | uHTS Luminescent assay for identification of inhibitors of Sentrin-specific protease 7 (SENP7) |
| Dead 48th | 0.8 | 652067 | 5354 | 364920 | 13 | 37 | 2.46798E-13 | 6.19149E-08 | Luminescence-based cell-based primary high throughput screening assay to identify activators of the DAF-12 from the parasite H. contortus (hcDAF-12) |
| Dead 48th | 0.8 | 2540 | 4122 | 326357 | 12 | 35 | 4.70493E-13 | 1.18034E-07 | HTS Luminescent assay for ientification of inhibitors of Sentrin-specific protease 8 (SENP8) |
| Dead 48th | 0.8 | 2599 | 5820 | 324659 | 13 | 34 | 1.1908E-12 | 2.98739E-07 | uHTS Luminescent assay for ientification of inhibitors of Sentrin-specific protease 6 (SENP6) |
| Dead 48th | 0.8 | 485297 | 9143 | 301950 | 12 | 19 | 3.30438E-11 | 8.2898E-06 | QHTS Assay For Rab9 Promoter Activators |
| Dead 48th | 0.8 | 485313 | 7586 | 304845 | 10 | 24 | 5.151E-09 | 0.001292246 | QHTS Assay For NPC1 Promoter Activators |
| Dead 48th | 0.8 | 504466 | 4174 | 306923 | 8 | 26 | 1.33401E-08 | 0.003346679 | qHTS screen for small molecules that induce genotoxicity in human embryonic kidney (HEK293T) cells expressing luciferase-tagged ELG1 |
| Dead 48th | 0.8 | 932 | 5134 | 190877 | 9 | 18 | 1.67632E-08 | 0.004205435 | Primary cell-based high-throughout screening assay to measure STAT1 activation |
| Dead 48th | 0.8 | 602393 | 7048 | 338975 | 9 | 27 | 3.24528E-08 | 0.008141537 | Screen for inhibitors of the SWI/SNF chromation remodeling complex (esBAF) in mouse embryonic stem cells with Luciferase reporter assay Measured in Cell-Based System Using Plate Reader-2141- |
| Dead 48th | 0.8 | 651644 | 751 | 354319 | 5 | 37 | 3.28707E-08 | 0.008246377 | qHTS Assay for Inhibitors of the HIV-1 protein Vpr |
| Dead 48th | 0.8 | 1463 | 2576 | 251621 | 6 | 16 | 6.82885E-08 | 0.017131734 | Counterscreen QHTS For Inhibitors Of Tau Fibril Formation, Fluorescence Polarization |
| Dead 48th | 0.8 | 743279 | 17205 | 328767 | 13 | 32 | 1.61834E-07 | 0.040599703 | qHTS Assay for Inhibitors of Inflammasome Signaling: IL-1-beta AlphaLISA Primary Screen |
| Delay / Arrest | 0.6 | 602229 | 1282 | 361068 | 4 | 1 | 7.77047E-10 | 0.00019494 | Luminescence-based cell-based primary high throughput primary screening assay to identify agonists of nuclear receptor subfamily 2, group E, member 3 (NR2E3) |
| Delay / Arrest | 0.6 | 686940 | 2610 | 367664 | 4 | 1 | 1.22287E-08 | 0.003067848 | Luminescence-based cell-based primary high throughput screening assay to identify inhibitors of COUP-TFII (NR2F2) |
| Delay / Arrest | 0.6 | 651719 | 1564 | 356555 | 3 | 2 | 8.24146E-07 | 0.206755864 | Fluorescence-based cell-based primary high throughput screening assay to identify antagonist of teh Galanin Receptro 3 (GalR3) |
| More Than One | 0.5 | 651702 | 2404 | 361030 | 6 | 19 | 1.3002E-08 | 0.003261398 | Flow Cytometric HTS Screening For Inhibitors Of Lytic Granula Exocytosis With MLPCN Compound Library |

FIG. 17, con't.

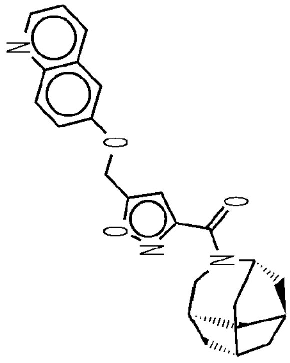
19759648
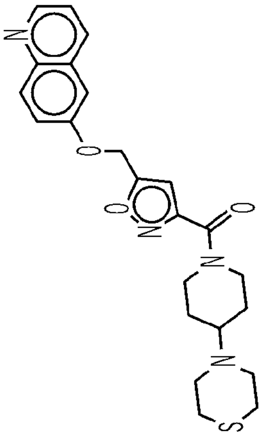
45187255
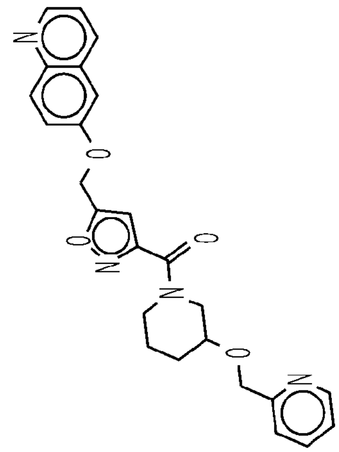
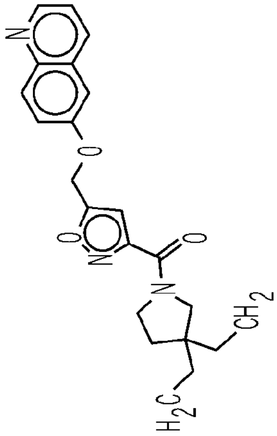
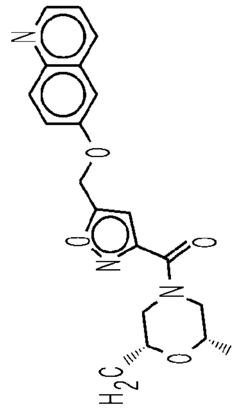
4488923
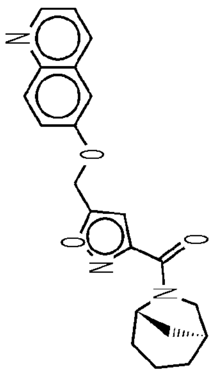
54305680
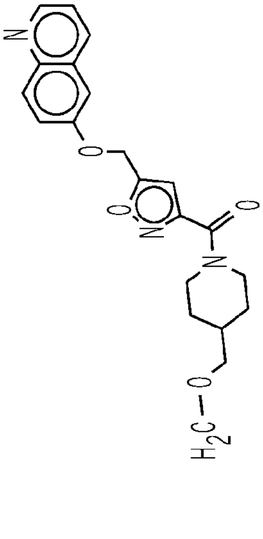
13197878
FIG. 18

METHODS FOR DRUG SCREENING AND COMPOSITIONS USEFUL FOR THE INHIBITION OF CELL PROLIFERATION AND/OR CELL SURVIVAL

CROSS-REFERENCE TO RELATED APPLICATIONS

This application is the U.S. National Stage of PCT/US2020/062569 with international filing date of 30 Nov. 2020, and which claims priority to U.S. Application No. 62/944,864 filed 6 Dec. 2019. The entire content of each of the above-referenced applications is incorporated herein by reference in its entirety.

STATEMENT REGARDING FEDERALLY SPONSORED RESEARCH

This invention was made with government support under OD017870 awarded by the National Institutes of Health. The government has certain rights in the invention.

FIELD OF THE INVENTION

The present disclosure relates to the field of drug discovery and therapeutics, including systems and methods to predict drug function, to classify or prioritize drugs based on predicted function, and to test known and novel compounds for function in a vertebrate system. The present disclosure also relates to compounds identified using the disclosed systems and methods, the novel mechanisms of action of the compounds, and applications of the compounds as therapeutics, e.g., as cancer therapeutics.

BACKGROUND OF THE INVENTION

Drug discovery in the post-genomic era has largely focused on modulation of disease-relevant drug targets in hypothesis-driven screens[1]. Small molecules or biologics found to modulate these targets in cellular reporter assays are nominated as leads and then undergo medicinal chemistry for optimization, subsequent preclinical testing, and clinical trials[2]. However, despite tremendous achievements in drug development, the timeline, failure rate, and expense of the entire process continue to limit the productivity of pharmaceutical companies[3]. Failures in the clinical phases of development may arise from lack of efficacy, unexpected toxicity arising from off-target or on-target effects, or unexpected anomalies in absorption, distribution, metabolism, or excretion. As a consequence of these constraints, the pharmaceutical industry has begun to explore complementary strategies in drug discovery[3].

One such strategy, phenotype-based screening, has been variably successful, and is capable of accessing multiple relevant specificity and toxicity phenotypes simultaneously. In addition to enabling program-specific compounds, this approach can also provide vital annotation of small molecule libraries early in the discovery process independent of the therapeutic indication. Nevertheless, systematic approaches to phenotype-driven library annotation have only recently begun to impact drug development[1,4].

Typical phenotypic screening involves the investigation of one or a small number of observable endpoints, however, advances in high-throughput microscopy over the past two decades[5] have facilitated classification of compounds based on in-depth phenotypic measurements[6]. These measurements can correspond to drug mechanism of action[5-8], and as such, have been useful in identifying compound targets[9,10]. The recent emergence of high-content microscopy-based techniques, notably including cell painting[11], have generated hundreds of phenotypic measurements for the purpose of generating multidimensional phenotypic barcodes, a valuable resource for small molecule mechanistic studies[12]. Similarly, so-called co-clinical studies, with parallel assessment of the growth of cancer cell lines[13,14] holds particular relevance for personalized medicine, as patient cells may be used to identify or infer sensitivities to specific small molecules, dictating subsequent treatment[15]. The addition of fully agnostic or semi-agnostic machine-based cell phenotyping and machine-trained suppression of cellular disease phenotypes has begun to be incorporated into drug discovery with some success. Ideally, it might be feasible to adopt such agnostic approaches across entire libraries and incorporate both cell autonomous and non-cell autonomous endpoints through the use of screenable organisms.

Due to their experimental tractability, model eukaryotes such as *S. cerevisiae* and *C. elegans* have become popular over the past several years for investigative analysis of the phenotypic effects of small molecules targeting core eukaryotic bioprocesses[16-21]. While assays in these organisms often allow the elegant determination of putative small molecule targets[17,20], such models lack disease-relevant phenotypic endpoints, limiting eventual clinical applicability. Embryonic zebrafish, owing to their vertebrate evolution, transparency, permeability, and rapid growth have become increasingly popular for phenotype-based small molecule screening. Since phenotypes observed during zebrafish development typically map directly onto processes in higher vertebrates, drugs identified in phenotype-driven screens often have corresponding effects in mammalian systems. For example, zebrafish screening identified dorsomorphin as a BMP pathway inhibitor[22], an analog of which was found to reduce heterotopic ossification in a transgenic mouse model[23]. Similarly, North and colleagues examined small-molecule effects on hematopoietic stem cell development, identifying ten compounds that affect the prostaglandin pathway, specifically prostaglandin E2[24] (pgE2). Subsequent work demonstrated that these compounds could improve graft potency in a murine transplantation model, and as a result pgE2 is being evaluated as a graft enhancer in humans[25]. More recently, Griffin et al recently used a SCN1A mutant phenotype complementation screen to identify novel therapeutics that immediately showed promise in treating Dravet syndrome, a childhood epilepsy[26]. Zebrafish phenotype-based screens can provide sufficient numbers of hits to begin clustering compounds based on shared phenotypes[27,28], however to date there have been no systematic efforts to annotate libraries across a broad set of in vivo phenotypes.

DESCRIPTION OF THE INVENTION

High-throughput screening platforms have demonstrated the utility of agnostic or semi-agnostic phenotypic profiling for the reproducible identification of molecular function and as an immediate readout of cellular efficacy to complement traditional target-based lead discovery. Here we demonstrate the utility of an in vivo, animal-based phenotypic screening platform for small molecule annotation combining the benefits of high-throughput screening with the capability to capture heterologous or non-cell-autonomous effects.

We screened a library of bioactive compounds in embryonic zebrafish, recording compound-phenotype associations spanning a series of simple, discrete, binary developmental phenotypes. Initial analysis of the compounds identified molecular sub-structures frequently associated with specific phenotypic outcomes, allowing the generation of machine learning models that prioritized the as-yet-untested compounds on the basis of their likelihood to generate individual phenotypic effects. We prioritized these effects across 56 million PubChem compounds, and were able to validate multiple predicted specific in vivo phenotypes. In one such set of experiments, we identified a class of small molecules capable of causing developmental arrest in zebrafish through an apparently novel mechanism. These results highlight a mechanism-agnostic means for combined in vivo and in silico screening of large chemical libraries, generating results with potentially immediate relevance for a range of biomedical applications.

Disclosed herein are compound identified in the screening methods that show activity with respect to one or more of cell proliferation and/or cell survival, developmental delay/developmental arrest, cardiac development and function, pigmentation, and body axis development. Thus, in some embodiments, these compounds are formulated as therapeutic compositions, and are useful to treat disease and conditions in a subject in need thereof. By way of example, in some embodiments, a subject is suffering from or is diagnosed with a disease or condition characterized by aberrant cell growth, cell division, and/or cell proliferation, and is administered a compound comprising Formula I, or derivatives, isomers, or pharmaceutically acceptable salts thereof.

As another example, in some embodiments disclosed herein are methods for inhibiting cell proliferation and/or cell survival comprising administering an effective amount of a compound comprising Formula I, or derivatives, isomers, or pharmaceutically acceptable salts thereof. In some embodiments disclosed herein are methods of treating a disease or condition characterized by increased cell proliferation and/or cell growth in a subject in need thereof, comprising administering to the subject an effective amount of a compound comprising Formula I, or derivatives, isomers, or pharmaceutically acceptable salts thereof. In some embodiments, the subject is human. In some embodiments, the disease or condition comprises cancer. In some embodiments, the cancer comprises bone cancer. In some embodiments, the bone cancer comprises osteosarcoma.

In some embodiments, methods disclosed herein includes reversibly decreasing the activity of phospholipase D and/or reducing the amount of phosphatidic acid in a subject in need thereof, comprising administering to the subject an effective amount of a compound comprising Formula I, or derivatives, isomers, or pharmaceutically acceptable salts thereof. In some embodiments, the subject is human. In some embodiments, the subject is diagnosed with or is suspected of having Alzheimer's disease.

In some embodiments, methods disclosed herein includes increasing the activity of phospholipase A and/or phospholipase C in a subject in need thereof, comprising administering to the subject an effective amount of a compound comprising Formula I, or derivatives, isomers, or pharmaceutically acceptable salts thereof. In some embodiments, the subject is human.

The present invention is described herein using several definitions, as set forth below and throughout the application.

Definitions

Unless otherwise specified or indicated by context, the terms "a", "an", and "the" mean "one or more."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, the term "subject" may be used interchangeably with the term "patient" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

As used herein "control," as in "control subject" or "control sample" has its ordinary meaning in the art, and refers to a sample, or a subject, that is appropriately matched to the test subject or test sample and is treated or not treated as appropriate.

A "therapeutic agent" or "therapeutic molecule" includes a compound or molecule that, when present in an effective amount, produces a desired therapeutic effect, pharmacologic and/or physiologic effect on a subject in need thereof. It includes any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition.

BRIEF DESCRIPTION OF THE FIGURES

FIG. 13: Chemical structure of the delay/arrest confirmation compounds. Shown are the structures of the 7 top predictions from the ChemBridge library for the delay/arrest phenotype that elicited the expected phenotypic effect (outer circle). The maximum common substructure (MCS) among these compounds is shown in the center. The yeast active compound used as the query in HIP/HOP screening is shown in the bottom right (red box).

FIG. 17. Provides a table showing each phenotypic class for enrichment in 250,873 published bioactivity assays.

FIG. 18. Exemplary delay/arrest compounds identified by the screening methods disclosed herein.

COMPOUNDS

Figure 1A:
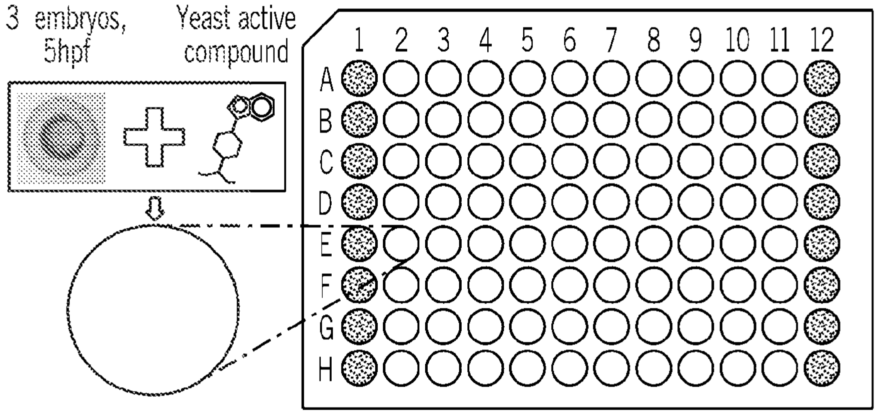
FIG. 1 (A)-(D): Screening procedure and observed phenotypes. Embryonic zebrafish were arrayed at 3 embryos per well in E3 media using standard 96 well plates (A), with either a single compound of interest (grey wells) or DMSO (blue wells) introduced at 5 hours post fertilization (hpf). The compound library used was enriched for biological activity through screening in *Saccharomyces Cerevisiae*, resulting in compounds having different mass and log P values than randomly selected purchasable compounds (B). Embryos were screened by two independent observers for phenotypic effects at 24 (C) and 48 (D) hours post-fertilization. Wild-type (DMSO) treated embryos are shown in the larger images for both time points, and common developmental abnormalities are shown in the smaller images (24 hpf (C) shows developmental arrest (top) and death (bottom), 48 hpf (D) shows embryos with cardiac defects (top left), body axis defects/death (top right and bottom left), and pigmentation defects (bottom right)). Bar graphs below the images indicate the frequency of observation of phenotypes at each time point.

Disclosed herein are methods and processes for drug screening and drug discovery comprising a vertebrate platform. Also disclosed herein are compounds identified in the drug screening methods that are useful for variety of medical and therapeutic applications. In some embodiments, the compounds are formulated into therapeutic compositions and are administered to subjects in need thereof.

A. Compounds that Inhibit Cell Proliferation and/or Cell Survival

Disclosed herein are compounds that exhibit inhibitory activity with respect to cell proliferation, cell growth, and/or cell survival. Such compounds comprise Formula I, derivatives, isomers, or pharmaceutically acceptable salts thereof:

(I)

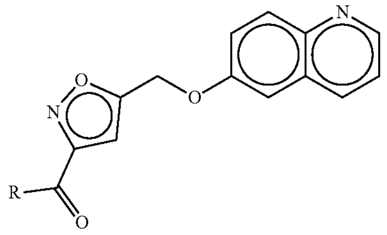

In some embodiments, R is an atom or a group of atoms. In some embodiments, R is selected from the group consisting of:

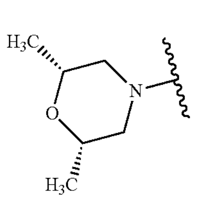
,
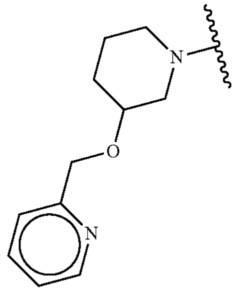
,
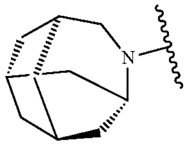
,
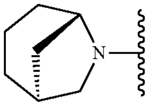
,
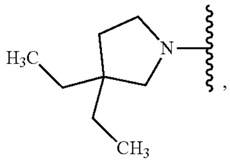
,
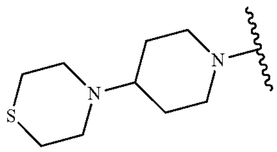
,
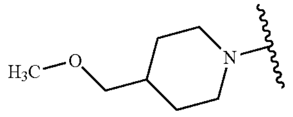
, and $NH_2$.

In some embodiments, compounds which exhibit inhibitory activity with respect to cell proliferation and/or cell growth, and/or cell survival comprise one or more compounds shown in FIG. 18, and as reproduced in Table 1 below.

TABLE 1
| Compounds that affect cell proliferation and/or cell survival | |
|---|---|
| ChemBridge ID No. (FIG. 18) | Compound structure |
| 4488923 | 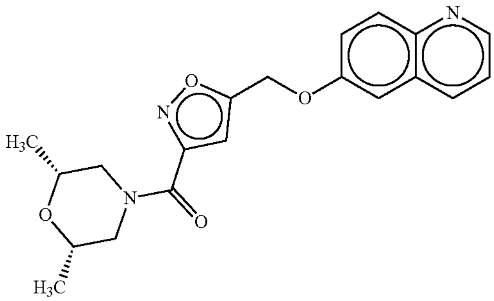 |
| 21652166 | 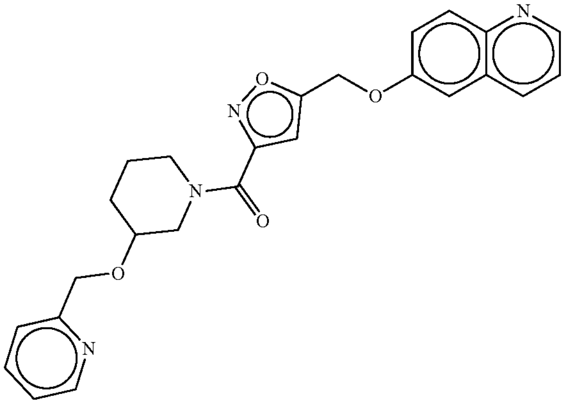 |
| 19759648 | 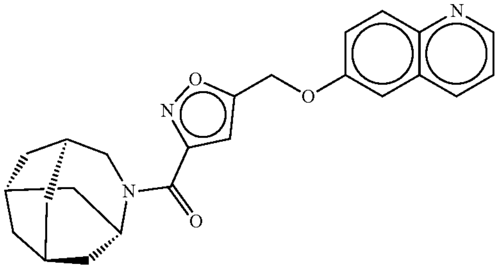 |
| 54305680 | 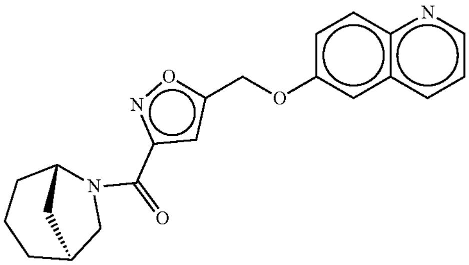 |

TABLE 1-continued

| Compounds that affect cell proliferation and/or cell survival | |
|---|---|
| ChemBridge ID No. (FIG. 18) | Compound structure |
| 65692859 ("DA5") | 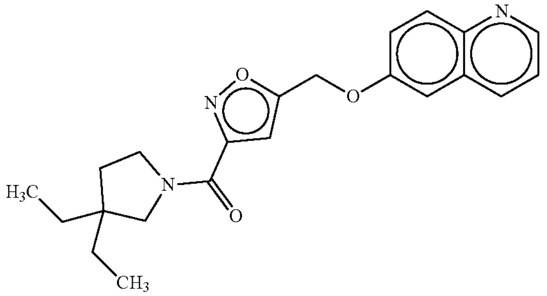 |
| 45187255 | 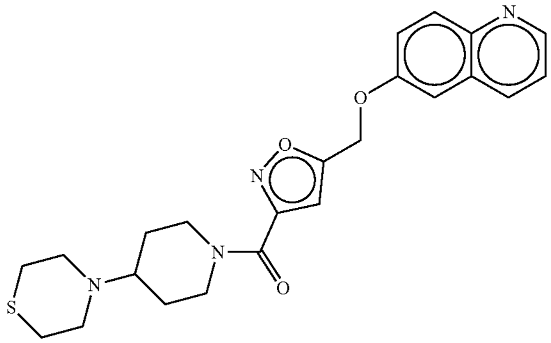 |
| 13197878 | 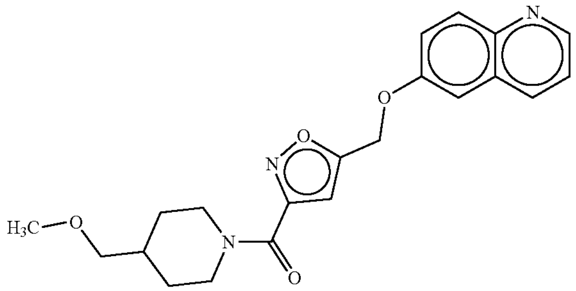 |

In some embodiments, one or more of the compounds is formulated as a therapeutic composition for administration to a subject in need thereof. In some embodiments, a subject in need thereof is suffering from a disease or condition characterized by an increased level of cell growth and/or cell division in one or more tissues, organs, or cell populations as compared to a control tissue, organ, or cell population.

In some embodiments, the disease or conditions characterized by an increased level of cell growth and/or cell division comprises cancer. By way of example, but not by way of limitation, in some embodiments, the cancer comprises one or more of Acute Lymphoblastic Leukemia (ALL); Acute Myeloid Leukemia (AML); Adrenocortical Carcinoma; AIDS-Related Cancers; Kaposi Sarcoma (Soft Tissue Sarcoma); AIDS-Related Lymphoma (Lymphoma); Primary CNS Lymphoma (Lymphoma); Anal Cancer; Astrocytomas, Childhood (Brain Cancer); Atypical Teratoid/Rhabdoid Tumor, Childhood, Central Nervous System (Brain Cancer); Basal Cell Carcinoma of the Skin; Bile Duct Cancer; Bladder Cancer; Bone Cancer (includes Ewing Sarcoma and Osteosarcoma and Malignant Fibrous Histiocytoma); Brain Tumors; Breast Cancer; Bronchial Tumors (Lung Cancer); Burkitt Lymphoma (Non-Hodgkin Lymphoma); Carcinoid Tumor (Gastrointestinal); Carcinoma of Unknown Primary origin; Cardiac (Heart) Tumors, Childhood Central Nervous System; Atypical Teratoid/Rhabdoid Tumor, Childhood (Brain Cancer); Medulloblastoma and Other CNS Embryonal Tumors, Childhood (Brain Cancer); Germ Cell Tumor, Childhood (Brain Cancer); Primary CNS Lymphoma; Cervical Cancer; Cholangiocarcinoma (Bile Duct Cancer); Chordoma, Bone Cancer; Chronic Lymphocytic Leukemia (CLL); Chronic Myelogenous Leukemia (CML); Chronic Myeloproliferative Neoplasms; Colorectal Cancer; Craniopharyngioma; utaneous T-Cell Lymphoma (Lymphoma (Mycosis Fungoides and Sezary Syndrome); Ductal Carcinoma In Situ (DCIS) (Breast Cancer); Embryonal Tumors, edulloblastoma and Other Central Nervous System, Endometrial Cancer (Uterine Cancer); Ependymoma, Esophageal Cancer; Esthesioneuroblastoma (Head and Neck Cancer); Ewing Sarcoma (Bone Cancer); Extracranial Germ Cell Tumor, Eye Cancer; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Gastrointestinal Carcinoid Tumor; Gastrointestinal Stromal Tumors (GIST) (Soft Tissue Sarcoma); Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer (Head and Neck Cancer); Intraocular Melanoma; Islet Cell Tumors, Pancreatic Neuroendocrine Tumors; Kaposi Sarcoma (Soft Tissue Sarcoma); Kidney (Renal Cell) Cancer; Langerhans Cell Histiocytosis; Laryngeal Cancer (Head and Neck Cancer); Leukemia; Lip and Oral Cavity Cancer (Head and Neck Cancer); Liver Cancer; Lung Cancer (Non-Small Cell, Small Cell, Pleuropulmonary Blastoma, and Tracheobronchial Tumor); Lymphoma; Male Breast Cancer; Malignant Fibrous Histiocytoma of Bone and Osteosarcoma; Melanoma; Melanoma, Intraocular (Eye)'; Merkel Cell Carcinoma (Skin Cancer); Mesothelioma, Malignant; Metastatic Cancer; Metastatic Squamous Neck Cancer with Occult Primary (Head and Neck Cancer); Midline Tract Carcinoma With NUT Gene Changes; Mouth Cancer (Head and Neck Cancer); Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer (Head and Neck Cancer); Nasopharyngeal Cancer (Head and Neck Cancer); Neuroblastoma; Non-Hodgkin Lymphoma; Non-Small Cell Lung Cancer; Oral Cancer, Lip and Oral Cavity Cancer and Oropharyngeal Cancer (Head and Neck Cancer); Osteosarcoma and Undifferentiated Pleomorphic Sarcoma of Bone Treatment; Ovarian Cancer; Pancreatic Cancer; Pancreatic Neuroendocrine Tumors (Islet Cell Tumors); Papillomatosis (Childhood Laryngeal); Paraganglioma; Paranasal Sinus and Nasal Cavity Cancer (Head and Neck Cancer); Parathyroid Cancer; Penile Cancer; Pharyngeal Cancer (Head and Neck Cancer); Pheochromocytoma; Pituitary Tumor; Plasma Cell Neoplasm/Multiple Myeloma; Pleuropulmonary Blastoma (Lung Cancer); Pregnancy and Breast Cancer; Primary Central Nervous System (CNS) Lymphoma; Primary Peritoneal Cancer; Prostate Cancer; Rectal Cancer; Renal Cell (Kidney) Cancer; Retinoblastoma; Rhabdomyosarcoma; Salivary Gland Cancer (Head and Neck Cancer); Sarcoma; Childhood Rhabdomyosarcoma (Soft Tissue Sarcoma); Childhood Vascular Tumors (Soft Tissue Sarcoma); Ewing Sarcoma (Bone Cancer); Kaposi Sarcoma (Soft Tissue Sarcoma); Osteosarcoma (Bone Cancer); Soft Tissue Sarcoma; Uterine Sarcoma; Sezary Syndrome (Lymphoma); Skin Cancer; Small Cell Lung Cancer; Small Intestine Cancer; Soft Tissue Sarcoma; Squamous Cell Carcinoma of the Skin; Squamous Neck Cancer with Occult Primary, Metastatic (Head and Neck Cancer); T-Cell Lymphoma, Cutaneous (Mycosis Fungoides and Sezary Syndrome); Throat Cancer (Head and Neck Cancer); Nasopharyngeal Cancer; Oropharyngeal Cancer; Hypopharyngeal Cancer; Thymoma and Thymic Carcinoma; Thyroid Cancer; Tracheobronchial Tumors (Lung Cancer); Transitional Cell Cancer of the Renal Pelvis and Ureter (Kidney (Renal Cell) Cancer); Ureter and Renal Pelvis, Transitional Cell Cancer (Kidney (Renal Cell) Cancer; Urethral Cancer; Uterine Cancer, Endometrial; Uterine Sarcoma; Vaginal Cancer; Vascular Tumors (Soft Tissue Sarcoma); Vulvar Cancer; Wilms Tumor.

By way of example, in some embodiments, a subject suffering from cancer, e.g., bone cancer, is administered a pharmaceutical composition comprising Formula I, or a derivative, isomer, or pharmaceutically acceptable salt thereof, in an amount sufficient to slow or inhibit the proliferation and/or cell growth, and/or cell survival of the bone cancer cells. In some embodiments, the subject is human. In some embodiments, the bone cancer comprises chondrosarcoma, Ewing sarcoma, or osteosarcoma. In some embodiments, the bone cancer is the result of a metastatic event (i.e., a cancer that begins elsewhere and metastasizes to the bone). In some embodiment, the bone cancer affects one or more types of bone cells, for example, the affected cells may be one or more of osteoblasts, osteocytes, osteoclasts and bone lining cells. In some embodiments, the compound comprises "DA5."

In some embodiments, a subject in need thereof is suffering from a disease or conditions characterized by increased levels of phospholipase D, or a condition or disease that that would be improved by reducing the level of phospholipase D. By way of example, but not by way of limitation, the disease or condition is Alzheimer's diseases, stroke, or other neurological disease, condition, or injury. In some embodiments, the subject is administered a pharmaceutical composition comprising Formula I, or a derivative, isomer, or pharmaceutically acceptable salt thereof, in an amount sufficient to decrease the levels of phospholipase D. In some embodiments, the compound comprises "DA5."

In some embodiments, a subject in need thereof is suffering from a disease or conditions characterized by reduced levels of phospholipase A and/or phospholipase C. Accordingly, some embodiments comprise a method of increasing the activity of phospholipase A and/or phospholipase C in a subject in need thereof, the method comprising: administering to the subject a therapeutically effective amount of a composition comprising Formula I, a derivative, isomer, or pharmaceutically acceptable salt thereof, in an amount sufficient to increase the levels of phospholipase A and/or phospholipase C. In some embodiments, the compound comprises "DA5." Abnormalities in phospholipase C have been associated with altered immune response (impaired T-cell migration and macrophage differentiation), hematological disorders (leukemia), and cancer (see Review by Cocco et al (2015) *Journal of Lipid Research,* 56(10):1853-60). Alterations in phospholipase A have been associated with cancer, specifically tumorigenesis, migration, invasion, and angiogenesis (see Review by Park et al (2012) *Nature Reviews Cancer,* 12:782-92), as well as inflammatory metabolic diseases such as diabetes and atherosclerosis (see Review by Hui (2012) Curr Opin Lipidol, 23(3):235-40).

In some embodiments, the population of cells to be treated comprises mammalian cells. By way of example but not by way of limitation, such cells may comprise osteoblasts, osteoclasts, myocytes, neurons, hematopoietic cells, epithelial cells, stem cells, and germ cells. In some embodiments, the cells comprise the cells or tissue of an organ. For example, the cells may comprise skin cells, liver cells, pancreatic cells, kidney cells, adrenal cells, lung cells, prostate cells, skin cells, brain cells, breast cells, bladder cells, bone cells, bone marrow cells, cardiac cells, or blood cells. In some embodiments, the cells are cancerous and exhibit aberrant cell growth, division and/or proliferation.

In some embodiments, the compound is used to inhibit cell growth, proliferation, and/or cell division in a population of cells in vitro. By way of example, the population of cells may be mammalian cells in culture. In some embodiments, the population of cells may be diseased cells, such as cancer cells.

B. Developmental Delay or Developmental Arrest

In some embodiments, compounds which result in delay/arrest phenotype are provided herein. In some embodiments, compounds that result in delay/arrest phenotype are shown in FIG. 13, and FIG. 18. Structures of these compounds are shown in the Table 2 below.

TABLE 2

| Compounds that cause developmental delay/arrest | |
|---|---|
| ChemBridge ID No. (FIG. 13) | Compound structure |
| 45187255 | 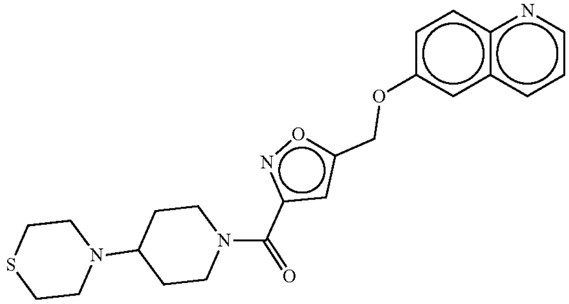 |
| 13197878 | 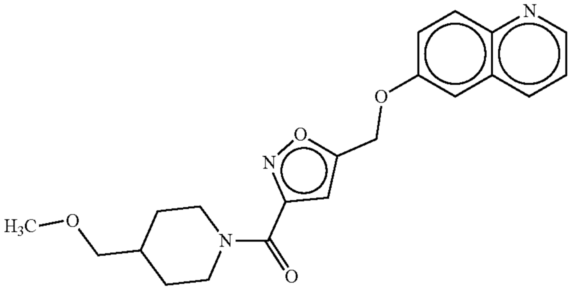 |
| 65692859 (DA5) | 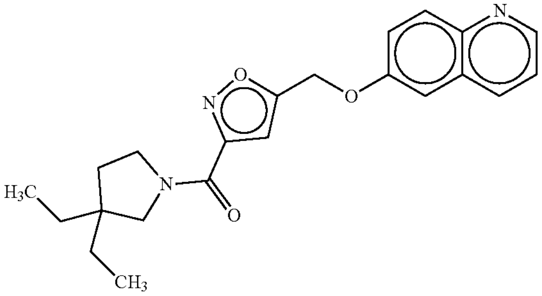 |
| 54305680 | 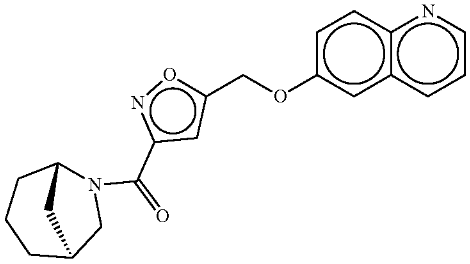 |
| 19759648 | 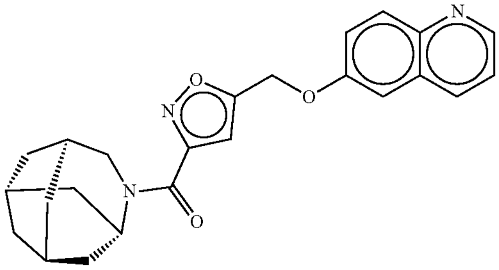 |

TABLE 2-continued

| Compounds that cause developmental delay/arrest | |
| --- | --- |
| ChemBridge ID No. (FIG. 13) | Compound structure |
| 21652166 | 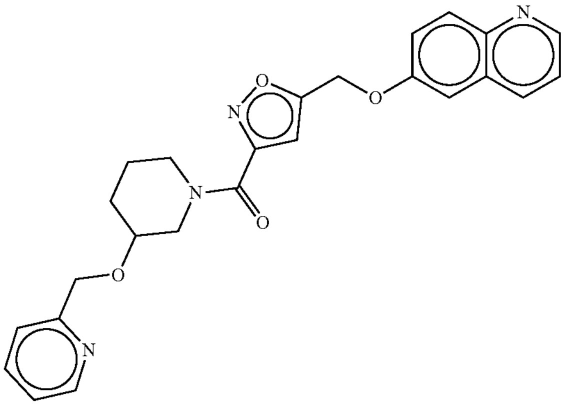 |
| 44889923 | 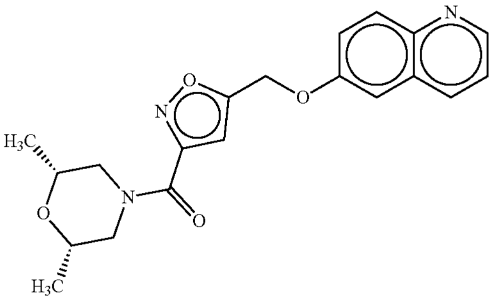 |
| 27235667 | 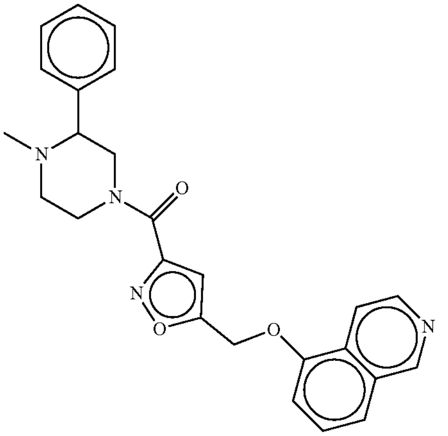 |

In some embodiments, compounds which result in delay/arrest phenotype comprise one or more of the following moieties

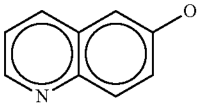

6-Hydroxyquinoline

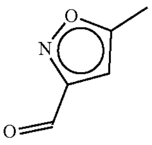

5-Methylisoxazole-3-carbaldehyde and

-continued

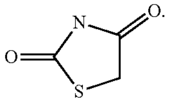

2,4-Thiazolidinedione

In some embodiments, compounds which result in a delay/arrest phenotype comprise a compound comprising Formula II:

II

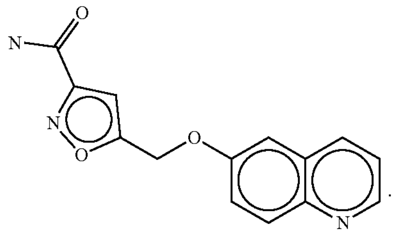

In some embodiments, a population of cells (e.g., target cells) is treated with a compound comprising Formula II, or a derivative, isomer, or pharmaceutically acceptable salt thereof, or a compound of Table 2, in an amount sufficient to delay or arrest development of target cells, or cells derived therefrom. In some embodiments, the cells are in an organism (e.g., a vertebrate subject, and/or in a mammalian subject). In some embodiments, the subject is human and the population of cells to be treated is within the human subject. In some embodiments, a pharmaceutical composition comprising Formula II or one or more of the compounds of Table 2 is administered to the subject. In some embodiments, the population of target cells is treated directly (e.g, by direct injection, or topical administration) of the pharmaceutical composition. For example, these compounds would allow discrete control of metabolism and cell biology in a reversible manner, as may be useful in cancer or in preservation of tissue under hypoxic or other threatening conditions.

C. Compounds that Affect Cardiac Development and Function

In some embodiments, compounds that affect cardiac development and/or cardiac function are provided herein. In some embodiments, compounds comprises those listed in FIG. 9. Structures of these compounds are shown in Table 3 below.

TABLE 3

| Cardiac compounds | |
|---|---|
| ChemBride ID No. (FIG. 9) | Compound structure |
| 37690524 | 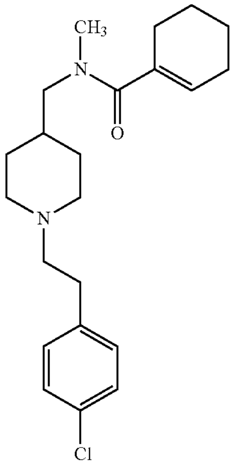 [SMILES: CN(CC1CCN(CCc2ccc(Cl)cc2)CC1)C(=O)C1=CCCCC1] |

TABLE 3-continued

| Cardiac compounds | |
|---|---|
| ChemBride ID No. (FIG. 9) | Compound structure |
| 39911836 | 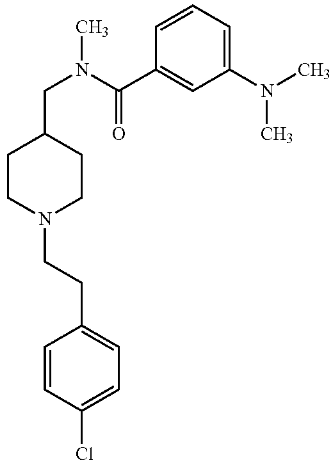 [SMILES: CN(CC1CCN(CCc2ccc(Cl)cc2)CC1)C(=O)c1cccc(N(C)C)c1] |
| 59314184 | 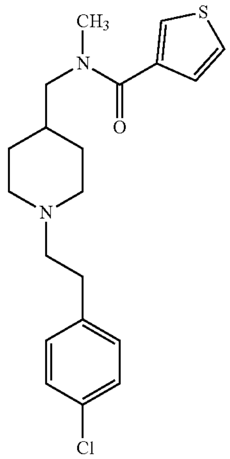 [SMILES: CN(CC1CCN(CCc2ccc(Cl)cc2)CC1)C(=O)c1ccsc1] |
| 18069546 | 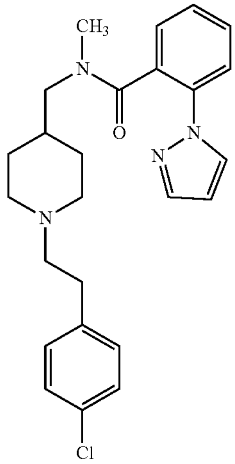 [SMILES: CN(CC1CCN(CCc2ccc(Cl)cc2)CC1)C(=O)c1ccccc1-n1cccn1] |

TABLE 3-continued
| Cardiac compounds | |
|---|---|
| ChemBride ID No. (FIG. 9) | Compound structure |
| 35983174 | 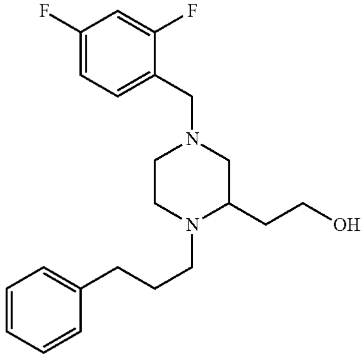 [SMILES: OCCC1CN(Cc2ccc(F)cc2F)CCN1CCCc1ccccc1] |
| 23490385 | 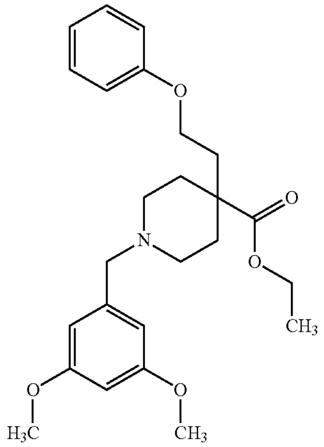 [SMILES: CCOC(=O)C1(CCOc2ccccc2)CCN(Cc2cc(OC)cc(OC)c2)CC1] |
| 87194463 | 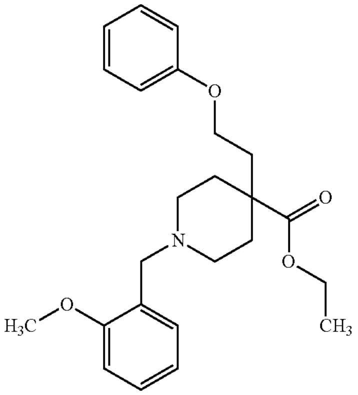 [SMILES: CCOC(=O)C1(CCOc2ccccc2)CCN(Cc2ccccc2OC)CC1] |
| 26410496 | 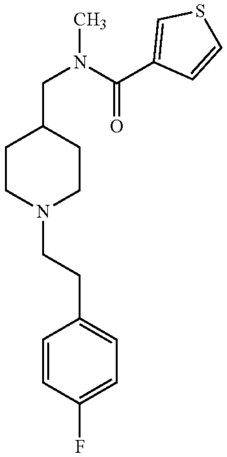 [SMILES: CN(CC1CCN(CCc2ccc(F)cc2)CC1)C(=O)c1ccsc1] |
| 38617825 | 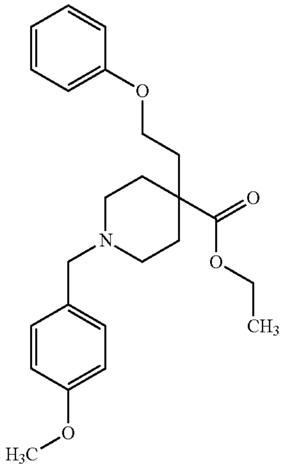 |
In some embodiments, the compounds comprise one or more of the following moieties:
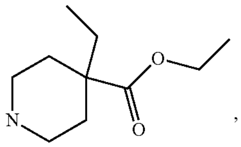
4-Ethyl-piperidine-4-carboxylic acid ethyl ester
,
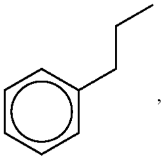
n-Propylbenzene
, and
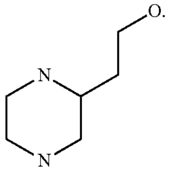
Monohydroxyethyl piperazine In some embodiments, a population of cells (e.g., target cells) is treated with a composition comprising one or more of the compounds of Table 3, or a derivative, isomer, or pharmaceutically acceptable salt thereof, in an amount sufficient to affect development or function of the target cells, or cells derived therefrom. In some embodiments, the cells are in an organism (e.g., a vertebrate subject). In some embodiments, the subject is human and the population of cells to be treated is within the human subject. In some embodiments, a pharmaceutical composition comprising any one or more of the compounds of Table 8 or a derivative, isomer, or pharmaceutically acceptable salt thereof, is administered to the subject. In some embodiments, the population of target cells is treated directly (e.g, by direct injection, or topical administration) of the pharmaceutical composition. These data suggest that the range of cellular processes that can be controlled by these compounds in a reversible manner may include: manipulation of cardiomyocyte behaviour in ischemia, heart muscle disease, or heart failure.

D. Compounds that Affect Pigmentation

In some embodiments, compounds that affect pigmentation are provided herein. In some embodiments, compounds comprises those listed in FIG. 11. Structures of these compounds are shown in Table 4 below.

TABLE 4

| Pigmentation compounds | |
|---|---|
| ChemBridge ID No. (FIG. 11) | Compound structure |
| 6108849 | 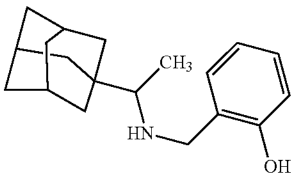 [SMILES: CC(NCc1ccccc1O)C12CC3CC(CC(C3)C1)C2] |
| 69904708 | 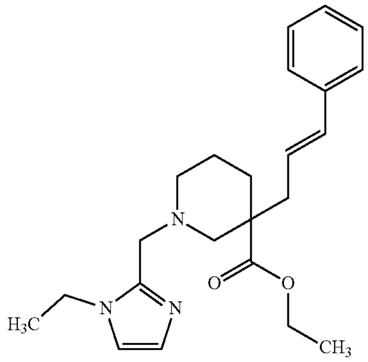 [SMILES: CCOC(=O)C1(C/C=C/c2ccccc2)CCCN(Cc2nccn2CC)C1] |
| 13300080 | 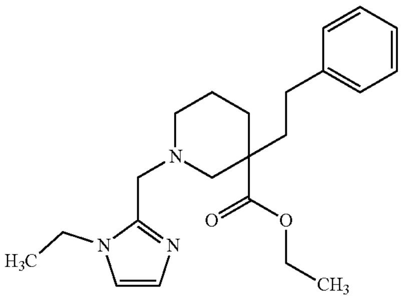 [SMILES: CCOC(=O)C1(CCc2ccccc2)CCCN(Cc2nccn2CC)C1] |

TABLE 4-continued

| Pigmentation compounds | |
|---|---|
| ChemBridge ID No. (FIG. 11) | Compound structure |
| 38433186 | 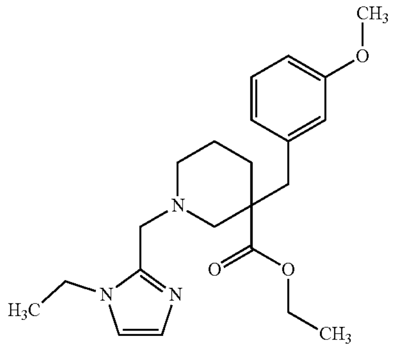 [SMILES: CCOC(=O)C1(Cc2cccc(OC)c2)CCCN(Cc2nccn2CC)C1] |
| 23702187 | 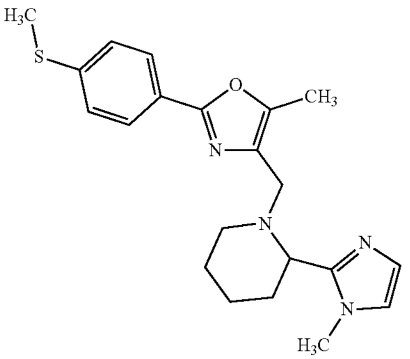 [SMILES: CSc1ccc(-c2nc(CN3CCCCC3c3nccn3C)c(C)o2)cc1] |
| 98334673 | 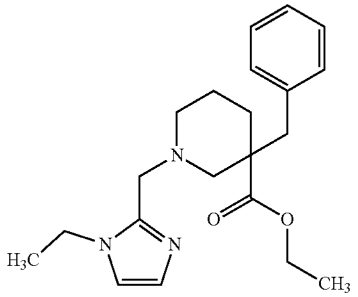 [SMILES: CCOC(=O)C1(Cc2ccccc2)CCCN(Cc2nccn2CC)C1] |
| 91866361 | 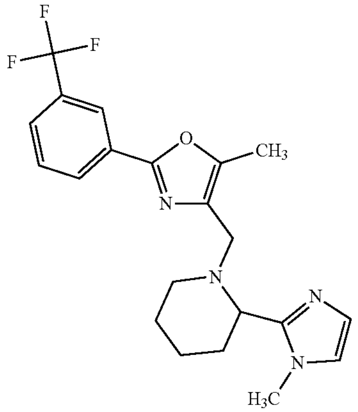 [SMILES: Cc1oc(-c2cccc(C(F)(F)F)c2)nc1CN1CCCCC1c1nccn1C] |

In some embodiments, the compounds comprise one or more of the following moieties:

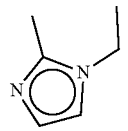

1-Ethyl-2-methyl-1H-imidazole

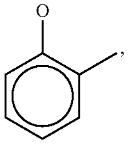

, and

2-Cresol

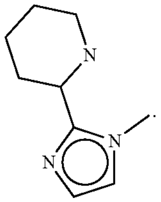

2-(1-methyl)-2-imidazolyl)piperidine

In some embodiments, a population of cells (e.g., target cells) is treated with a compound comprising one or more of the compounds of Table 4, or a derivative, isomer, or pharmaceutically acceptable salt thereof, in an amount sufficient to affect the pigmentation of the target cells, or cells derived therefrom. In some embodiments, the cells are in an organism (e.g., a vertebrate subject). In some embodiments, the subject is human and the population of cells to be treated is within the human subject. In some embodiments, a pharmaceutical composition comprising any one or more of the compounds of Table 4 is administered to the subject. In some embodiments, the population of target cells is treated directly (e.g, by direct injection, or topical administration) of the pharmaceutical composition. These data suggest that the range of cellular processes that can be controlled by these compounds in a reversible manner may include: melanoma or other melanocyte disorders.

E. Compounds that Affect Body Axis Development

In some embodiments, compounds that affect the development of body axis are provided herein. In some embodiments, compounds comprises those listed in FIG. 10. Structures of these compounds are shown in Table 5, below.

TABLE 5

| Body axis compounds | |
|---|---|
| CamBridge ID No. (FIG. 10) | Compound structure |
| 20494296 | 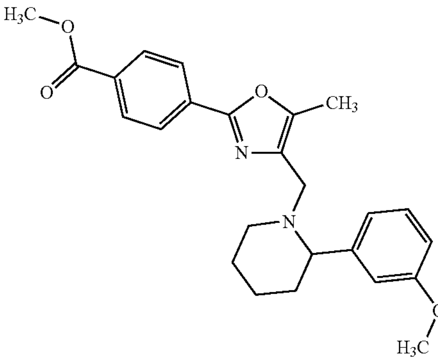 |

TABLE 5-continued

| Body axis compounds | |
|---|---|
| CamBridge ID No. (FIG. 10) | Compound structure |
| 34105851 | 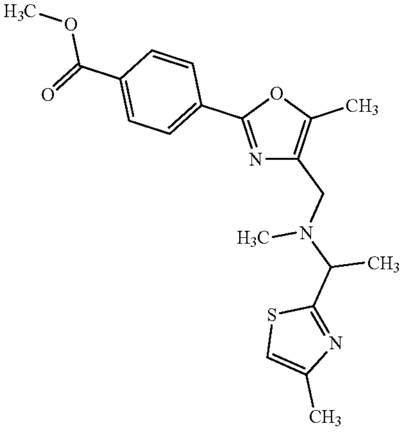 [SMILES: COC(=O)c1ccc(-c2nc(CN(C)C(C)c3nc(C)cs3)c(C)o2)cc1] |
| 86606851 | 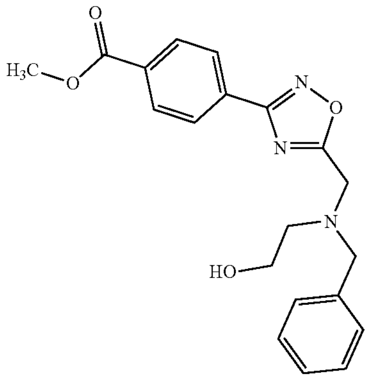 [SMILES: COC(=O)c1ccc(-c2noc(CN(CCO)Cc3ccccc3)n2)cc1] |
| 18809966 | 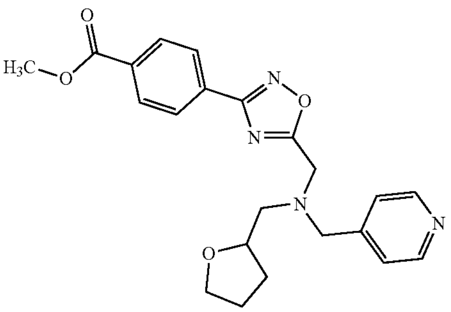 [SMILES: COC(=O)c1ccc(-c2noc(CN(Cc3ccncc3)CC3CCCO3)n2)cc1] |
| 22685803 | 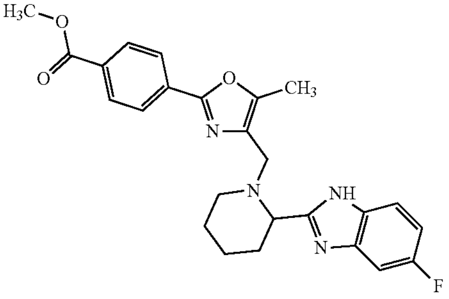 [SMILES: COC(=O)c1ccc(-c2nc(CN3CCCCC3c3nc4cc(F)ccc4[nH]3)c(C)o2)cc1] |

TABLE 5-continued

| Body axis compounds | |
|---|---|
| CamBridge ID No. (FIG. 10) | Compound structure |
| 56638922 | 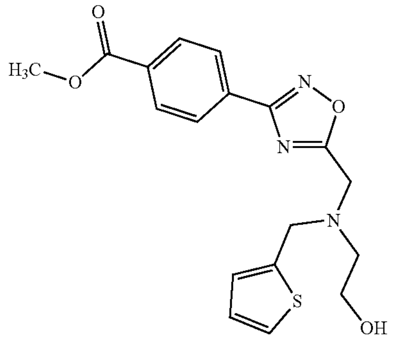 [SMILES: COC(=O)c1ccc(-c2noc(CN(CCO)Cc3cccs3)n2)cc1] |

In some embodiments, the compounds comprise one or more of the following moieties:

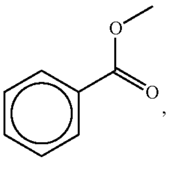

Methyl Benzoate

,

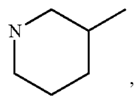

3-methyl piperidine

, and

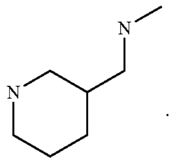

methyl-piperidin-3-ylmethyl-amine

.

In some embodiments, a population of cells (e.g., target cells) is treated with a compound comprising one or more of the compounds of Table 5, or a derivative, isomer, or pharmaceutically acceptable salt thereof, in an amount sufficient to affect the developmental orientation of the target cells, or cells derived therefrom. In some embodiments, the cells are in an organism (e.g., a vertebrate subject). In some embodiments, the subject is human and the population of cells to be treated is within the human subject. In some embodiments, a pharmaceutical composition comprising any one or more of the compounds of Table 5 is administered to the subject. In some embodiments, the population of target cells is treated directly (e.g, by direct injection, or topical administration) of the pharmaceutical composition. These data suggest that the range of cellular processes that can be controlled by these compounds in a reversible manner may include muscle disorders.

Formulations and Modes of Administration

While the compositions disclosed herein may include pharmaceutical compositions comprising any of the compounds disclosed herein, Formula I, derivatives, isomers and pharmaceutically acceptable salts thereof, will be used as an example throughout the discussion of the various embodiments. It is to be understood that any of the compounds disclosed herein can be formulated and administered as described in this section at a dosage effective to treat a subject in need thereof.

Such compositions can be formulated and/or administered in dosages and by techniques well known to those skilled in the medical arts taking into consideration such factors as the age, sex, weight, and condition of the particular patient, and the route of administration.

The compositions may include pharmaceutical solutions comprising carriers, diluents, excipients, and surfactants, as known in the art. Further, the compositions may include preservatives (e.g., anti-microbial or anti-bacterial agents such as benzalkonium chloride). The compositions also may include buffering agents (e.g., in order to maintain the pH of the composition between 6.5 and 7.5).

The pharmaceutical compositions may be administered therapeutically. In therapeutic applications, the compositions are administered to a patient in an amount sufficient to elicit a therapeutic effect (e.g., a response which cures or at least partially arrests or slows symptoms and/or complications of disease (i.e., a "therapeutically effective dose").

In some embodiments, compositions are formulated for systemic delivery, such as oral or parenteral delivery. In some embodiments, minimally invasive microneedles and/or iontophoresis may be used to administer the composition. In some embodiments, compositions are formulated for site-specific administration, such as by injection into a specific tissue or organ, or by topical administration (e.g., by patch applied to the target tissue or target organ, e.g., cancer tissue or brain/neuronal tissue, etc.).

The therapeutic composition may include, in addition a compound of Formula I, one or more additional active agents. By way of example, the one or more active agents may include an antibiotic, anti-inflammatory agent, a steroid, or a non-steroidal anti-inflammatory drug, and chemotherapeutics.

According to various aspects, a compound of the present disclosure, and optionally the one or more active or inactive agents may be present in the composition as particles or may be soluble. By way of example, in some embodiments, micro particles or microspheres may be employed, and/or nanoparticles may also be employed, e.g., by utilizing biodegradable polymers and lipids to form liposomes, dendrimers, micelles, or nanowafers as carriers for targeted delivery of the compounds. In some embodiments, polymeric implants may be used. By way of example but not by way of limitation, in some embodiments, a therapeutic composition comprising DA5 is applied to a patch and placed in contact with the target tissue (e.g., a tumor).

In some embodiments, the composition formulated for administration comprises between 500 mg/ml and 1000 mg/ml of the compound, e.g., a compound comprising Formula I. In some embodiments, the composition formulated for administration comprises between 0.1 ng and 500 mg/ml of the compound, e.g., a compound comprising Formula I. In some embodiments, the compositions if formulated such that between 0.1 ng and 500 μg/ml of the compound (e.g., a compound comprising Formula I) is administered to a subject.

In some embodiments, the methods include administration of the therapeutic compositions once per day; in some embodiments, the composition may be administered multiple times per day, e.g., at a frequency of one or two times per day, or at a frequency of three or four times per day or more. In some embodiments, the methods include administration of the composition once per week, once per month, or as symptoms dictate.

In some embodiments, the composition is administered at between 500 mg/ml and 1000 mg/ml of inhibitor; between 0.1 ng and 500 mg/ml of the inhibitor; or between about 0.1 ng and 500 μg/ml of the inhibitor.

In some embodiments, the treatment reduces, alleviates, prevents, or otherwise lessens the symptoms of the disease or condition more quickly than if no treatment is provided to a subject suffering the same or similar disease, condition, or injury. By way of example, for a subject suffering from cancer, e.g., bone cancer, a treated subject would exhibit one or more of reduced tumor size, reduced tumor growth, reduced metastatic activity, reduced swelling near the tumor, and reduced joint or bone pain, sooner or at a greater degree than a non-treated subject with the same or similar cancer. By way of example, for a subject suffering from Alzheimer's disease, stroke, or other neurological disease or condition, a treated subject would exhibit an improvement in, or a reduced worsening of one or more of the following: memory, judgement, speech, writing, general confusion, understanding verbal and/or written communication, motor coordination, sooner or at a greater degree than a non-treated subject with the same or similar disease or condition.

In some embodiments, improvements in the condition of the subject's condition is observed more quickly than if no treatment is provided for the same or similar condition or disease.

By way of example, in some embodiments, improvements in the condition is observed within about 1 to about 3 days; within about 3 to about 5 days, or within about a week of the first administration. In some embodiments, improvements in the subject's condition is observed within about 10 days, about 14 days or within about 1 month of the first administration. In some embodiments, improvements in the subject's condition is observed within about 1-3 month, about 3-6 months or within about 1 year of the first administration.

EXEMPLARY EMBODIMENTS

Non-limiting exemplary embodiments of the present disclosure are provided below.

Embodiment 1. A method for inhibiting cell proliferation and/or cell survival, comprising administering to a population of cells, a compound of Formula I, derivatives, isomers, or pharmaceutically acceptable salts thereof, at a dosage effective to inhibit cell proliferation and/or survival, wherein Formula I is:

(I)

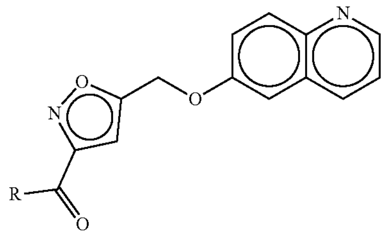

wherein R is an atom or a group of atoms.

Embodiment 2. The method of embodiment 1, wherein R is selected from the group consisting of:

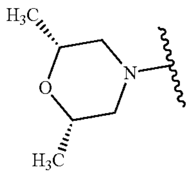
,
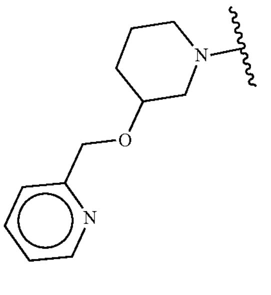
,

-continued

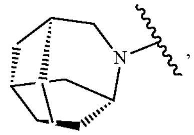
,
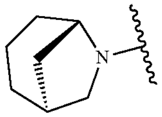
,
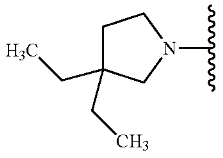
,
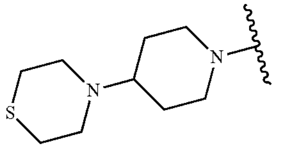
,
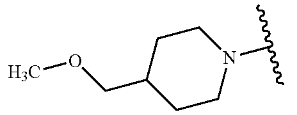
, and $NH_2$.

Embodiment 3. The method of embodiment 1, wherein the cells are eukaryotic cells.

Embodiment 4. The method of embodiment 3, wherein the cells are from a mammal or are in a mammal.

Embodiment 5. The method of c embodiment 4, wherein the mammal is a human and the population of cells is in the human.

Embodiment 6. The method of any one of embodiments 2-5, wherein the cells are somatic cells.

Embodiment 7. The method of any one of embodiments 2-5, wherein the cells are germ cells.

Embodiment 8. The method of any one of embodiments 2-5, wherein the cells are one or more of osteoblasts, osteoclasts, myocytes, neurons, hematopoietic cells, epithelial cells, and stem cells.

Embodiment 9. The method of any one of embodiments 2-5, wherein the cells are one or more of liver cells, pancreatic cells, kidney cells, adrenal cells, lung cells, prostate cells, skin cells, brain cells, breast cells, bladder cells, bone marrow cells, or blood cells.

Embodiment 10. The method of any one of embodiments 2-9, wherein the cells are cancer cells.

Embodiment 11. The method any one of embodiments 2-9, wherein administering is carried out in vivo.

Embodiment 12. The method of embodiment 11, wherein administering comprises one or more of the following routes: orally, parenterally, inhalation, and topically.

Embodiment 13. The method of embodiment 3, wherein the eukaryotic cells are from, or are in an animal, a protist, a plant, or a fungus.

Embodiment 14. The method of embodiment 1, wherein the cells are prokaryotic cells.

Embodiment 15. The method of embodiment 1, wherein the cells are mammalian cells in vitro.

Embodiment 16. The method of embodiment 15, wherein the mammalian cells in vitro are human cells.

Embodiment 17. The method of embodiment 1, wherein the compound of Formula I is formulated as a pharmaceutical composition.

Embodiment 18. A method of treating a disease or condition, the method comprising: administering to a subject in need thereof an effective amount of a compound of Formula I, derivatives, isomers, or pharmaceutically acceptable salts thereof, wherein Formula I is:

(I)

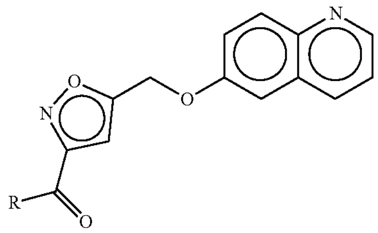

wherein R is an atom or a group of atoms.

Embodiment 19. The method of embodiment 18, wherein R is selected from the group consisting of:

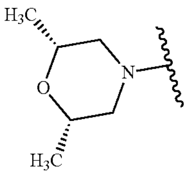 ,

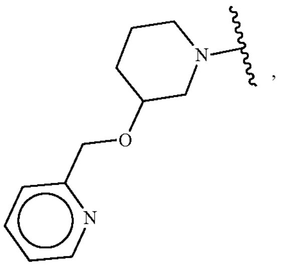 ,

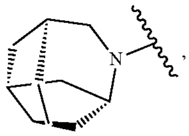 ,

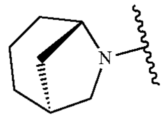 ,

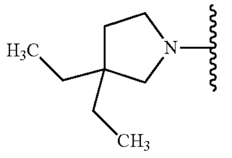 ,

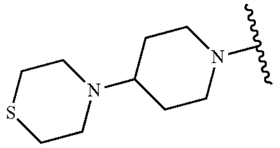 ,

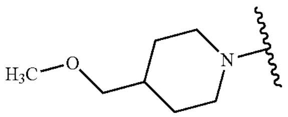 , and $NH_2$.

Embodiment 20. The method of embodiment 18, wherein the disease is cancer and the subject is a human.

Embodiment 21. A method of reversibly decreasing the activity of phospholipase D and/or reducing the amount of phosphatidic acid in a population of cells, the method comprising: administering to the population of cells a compound of Formula I, derivatives, isomers, or pharmaceutically acceptable salts thereof, at a dosage effective to reversibly decrease the activity of phospholipase D and/or reduce the amount of phosphatidic acid, wherein Formula I is:

(I)

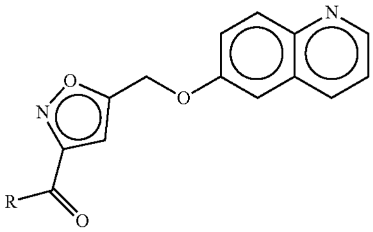

wherein R is an atom or a group of atoms.

Embodiment 22. The method of embodiment 21, wherein R is selected from the group consisting of:

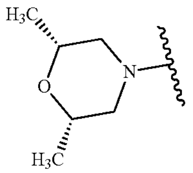 ,

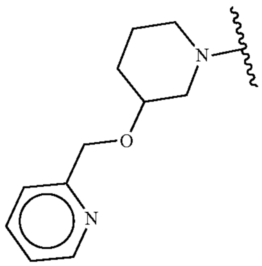 ,

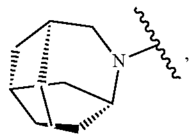 ,

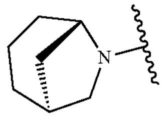 ,

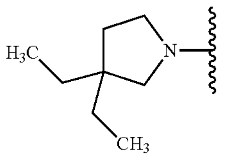 ,

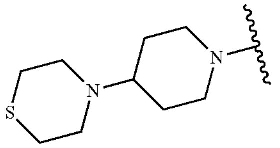 ,

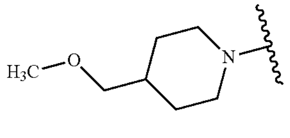 , and $NH_2$.

Embodiment 23. A method of increasing the activity of phospholipase A and/or phospholipase C in a population of cells, the method comprising:

administering to the population of cells a compound of Formula I, derivatives, isomers, or pharmaceutically acceptable salts thereof, at a dosage effective to increase the activity of phospholipase A and/or phospholipase C, wherein Formula I is:

(I)

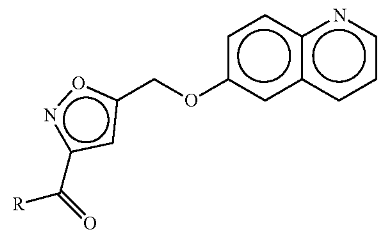

wherein R is an atom or a group of atoms.

Embodiment 24. The method of embodiment 23, wherein R is selected from the group consisting of:

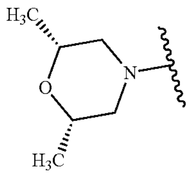
,
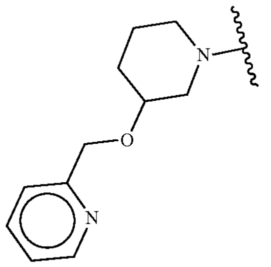
,
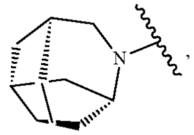
,
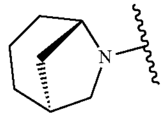
,
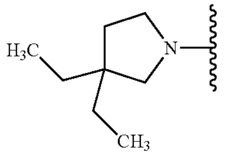
,
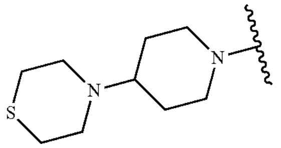
,
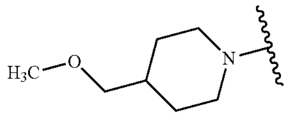
, and $NH_2$.

Embodiment 25. The method of any one of embodiments 23 or 24, wherein the cells are eukaryotic cells.

Embodiment 26. The method of any one of embodiments 23 or 24, wherein the cells are from a mammal or are in a mammal.

Embodiment 27. The method of embodiment 26, wherein the mammal is a human and the population of cells is in the human.

Embodiment 28. The method of any one of embodiments 23 to 27, wherein administering is carried out in vivo.

Embodiment 29. The method of any one of embodiments 23 to 27, wherein the cells are mammalian cells in vitro.

Embodiment 30. The method of embodiment 29, wherein the mammalian cells in vitro are human cells.

Embodiment 31. The method of any one of embodiments 1, 18, 21 or 23, wherein the cells are vertebrate cells.

EXPERIMENTAL EXAMPLES

The following Examples are illustrative and should not be interpreted to limit the scope of the claimed subject matter.

Overview

To validate a vertebrate model to annotate libraries across a broad set of in vivo phenotypes, we began by systematically annotating 'any and all' observable binary dissection microscopy phenotypes in embryonic zebrafish following exposure to a 'yeast active' (henceforth 'yactive') library of 4,182 compounds previously identified to have bioactivity in yeast and to be enriched for activity a number of model organisms[29], but without other characterization. We observed a high hit rate for several binary phenotypic classes (cardiac abnormality, pigmentation defects, death, developmental delay, cranial edema, and body axis defects), finding distinct chemical sub-structures to be specifically enriched for each phenotypic class. Using a machine learning framework, we evaluated the likelihood of specific phenotypic effects for 56 million compounds contained in PubChem[30], overlaying bioassay data[31] to identify common themes of bioactivity among compounds predicted to cause specific phenotypic effects. We also prioritized over 900,000 commercially available compounds for their likelihood of causing specific phenotypes, allowing identification of a class of compounds eliciting developmental arrest through an apparent alteration in plasma membrane composition. These results outline a clear pipeline for en masse structure-phenotype association using mechanism agnostic library annotation in vertebrates.

Example 1 Bioactive Compounds Exhibit a Range of Developmental Phenotypes

Figure 1B:
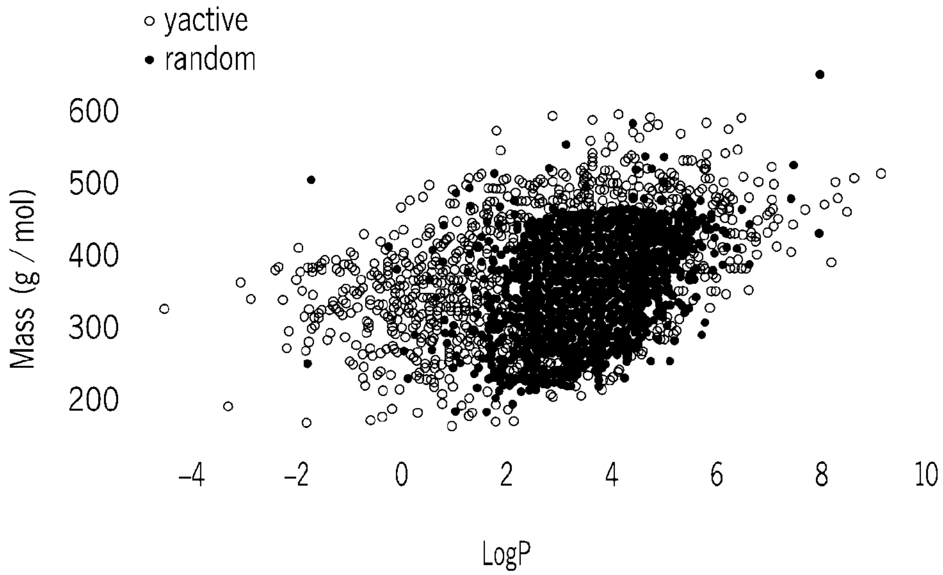

In an effort to associate chemical structures with vertebrate phenotypes, we began by screening the yactive library of 4,182 bioactive small molecules[29], for which bioactivity in yeast is evidence for a (usually unknown) eukaryotic target. Screening was performed for a range of observable associated phenotypes in embryonic zebrafish (see Methods and FIG. 1*a*). While still structurally diverse, these compounds had higher partition coefficients (3.93 versus 2.88) and higher formula weights (377.07 versus 360.965) than compounds randomly selected from the ChemBridge library ($p<0.0001$). The compounds also appeared to have a narrower distribution of partition coefficient and molar mass values (FIG. 1*b*), suggesting a potential 'sweet spot'32 for yeast activity in this range.

Figure 1D:
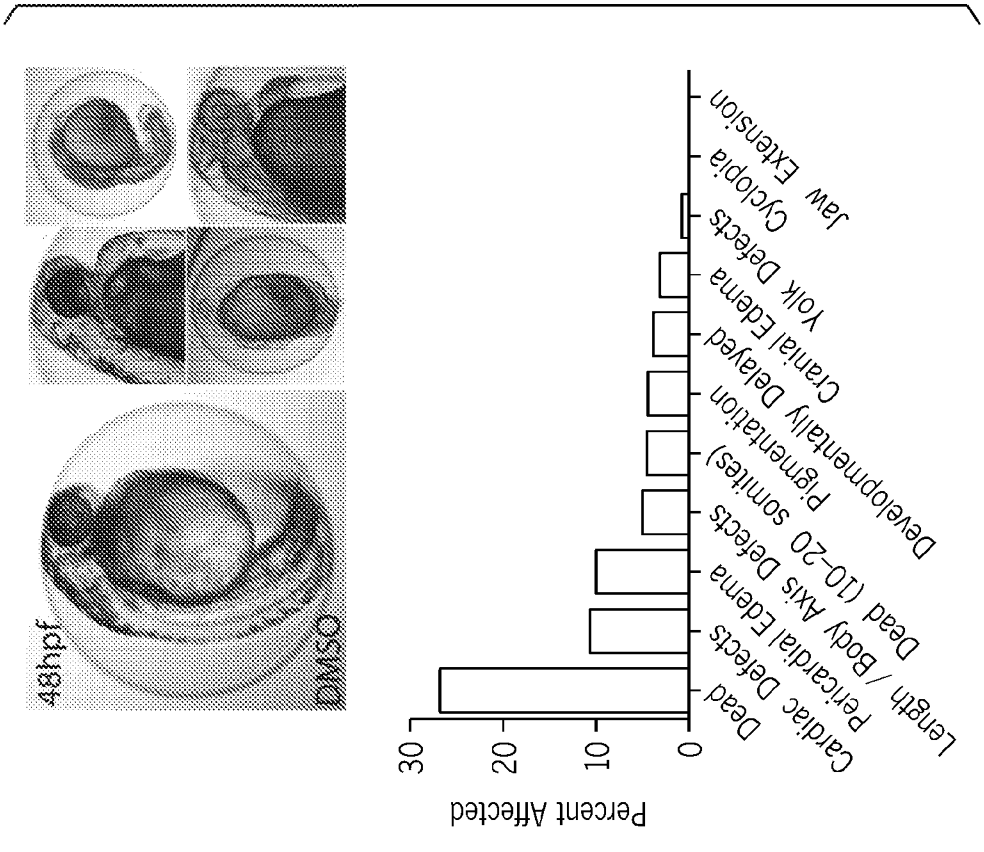
Figure 1C:
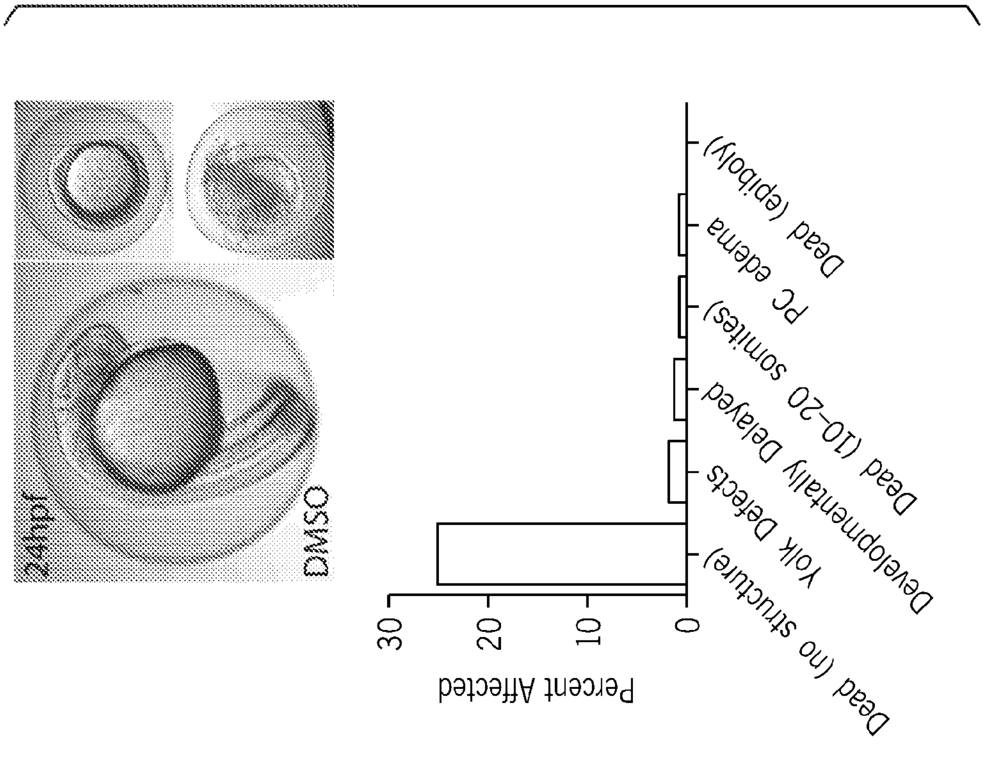
Figure 2A:
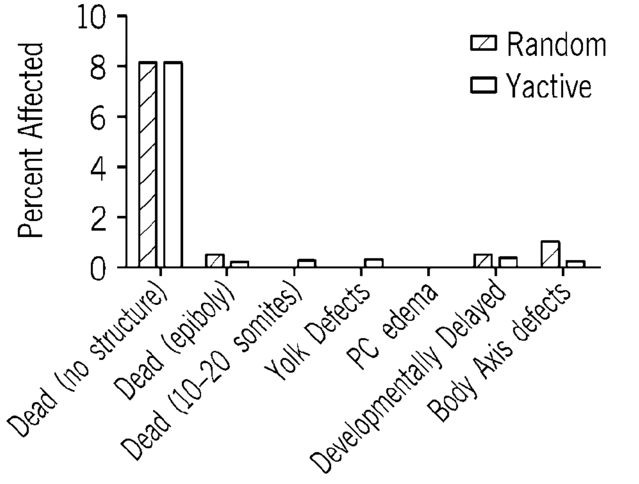
FIG. 2 (A)-(D): The relationship between structure and phenotype. Panels A and B show the relative proportion of phenotypes observed when screening the yeast active library (blue) versus compounds selected at random from the ChemBridge library (red) at 24 (A) and 48 (B) hours post fertilization. To evaluate the relationship between structural similarity of small molecules and observed phenotypes, propensity of structurally similar compounds to elicit similar phenotypes was compared versus randomly selected groups of compounds (see Methods). Over 10,000 simulations (shown in histogram, D), randomly selected compound sets did not match the average similarity in phenotype seen in the true set (vertical red line). The 4,182 small molecules screened for zebrafish phenotypes are displayed in panel C associated by structural similarity (as assessed by Tanimoto Coefficient of molecular fingerprints). Compounds were grouped into clusters using Markov Clustering (see Methods), and phenotypes observed are overlayed with the indicated colors. The 2 inset clusters show resulting groups of compounds with consistent (green box) and inconsistent (red box) phenotypic effects. These findings suggest a clear relationship between structure and phenotype for surveyed compounds, but also suggest that chemical structure alone does not strictly dictate observed phenotype.
Figure 2B:
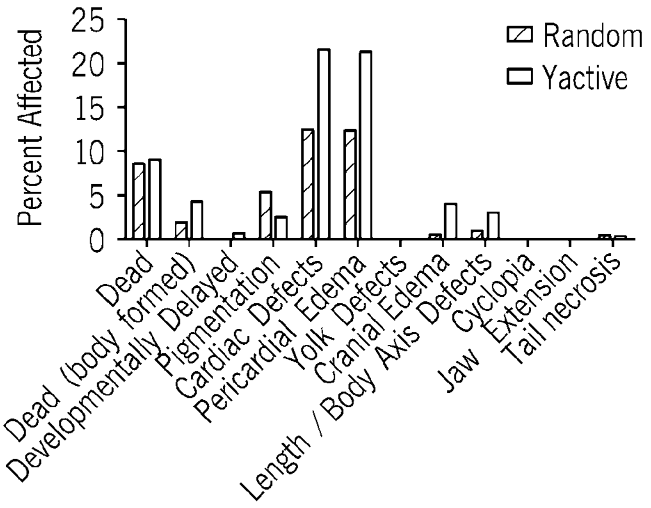

Using only a stereo microscope, we observed a range of phenotypes following exposure to this set of small molecules (FIG. 1*c-d*; see U.S. Appl. No. 62/944,864 Table S1), with 1,604 out of 4,182 (38%) eliciting at least one observable phenotype that could be classified in a binary manner. Mortality and cardiac phenotypes (classified as alterations in heart rate, heart size, or defects in conduction) were the most prevalent phenotypes observed (FIG. 1). Additional phenotypic effects such as abnormal appearance of the yolk, cranial edema, or profoundly altered developmental timing (herein developmental delay/arrest) were found in at least 1% of surveyed compounds (see U.S. Appl. No. 62/944,864 Table S1). Despite previous findings that compounds with bioactivity in one eukaryote are more likely to yield phenotypes in another[29], overall activity rates were generally consistent between the yactive and random libraries (FIG. 2*a-b*). One explanation for this general phenomenon is that prior annotations of the yactive library were obtained from bioactivity in organisms that are difficult to penetrate due to cell walls (yeast and bacteria), thick cuticles, and active extrusion (worm). A notable exception to this lack of correlation was aggregated cardiac phenotypes, which were nearly twice as common when using the yactive library (22% of compounds in the yactive library versus 12% of compounds in the random library; Bonferroni corrected $p<0.05$, Fisher's Exact Test). Given the breadth of observed phenotypes, we next sought to identify structural commonalities among compounds eliciting the same phenotype.

Example 2 Molecular Structure Dictates Developmental Phenotype

Figure 2D:
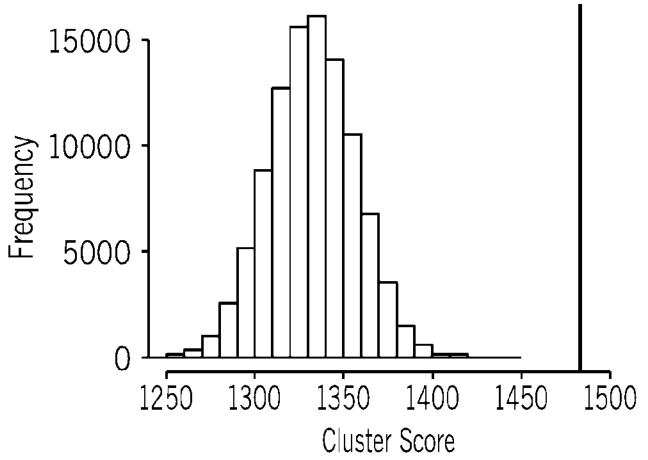
Figure 2C:
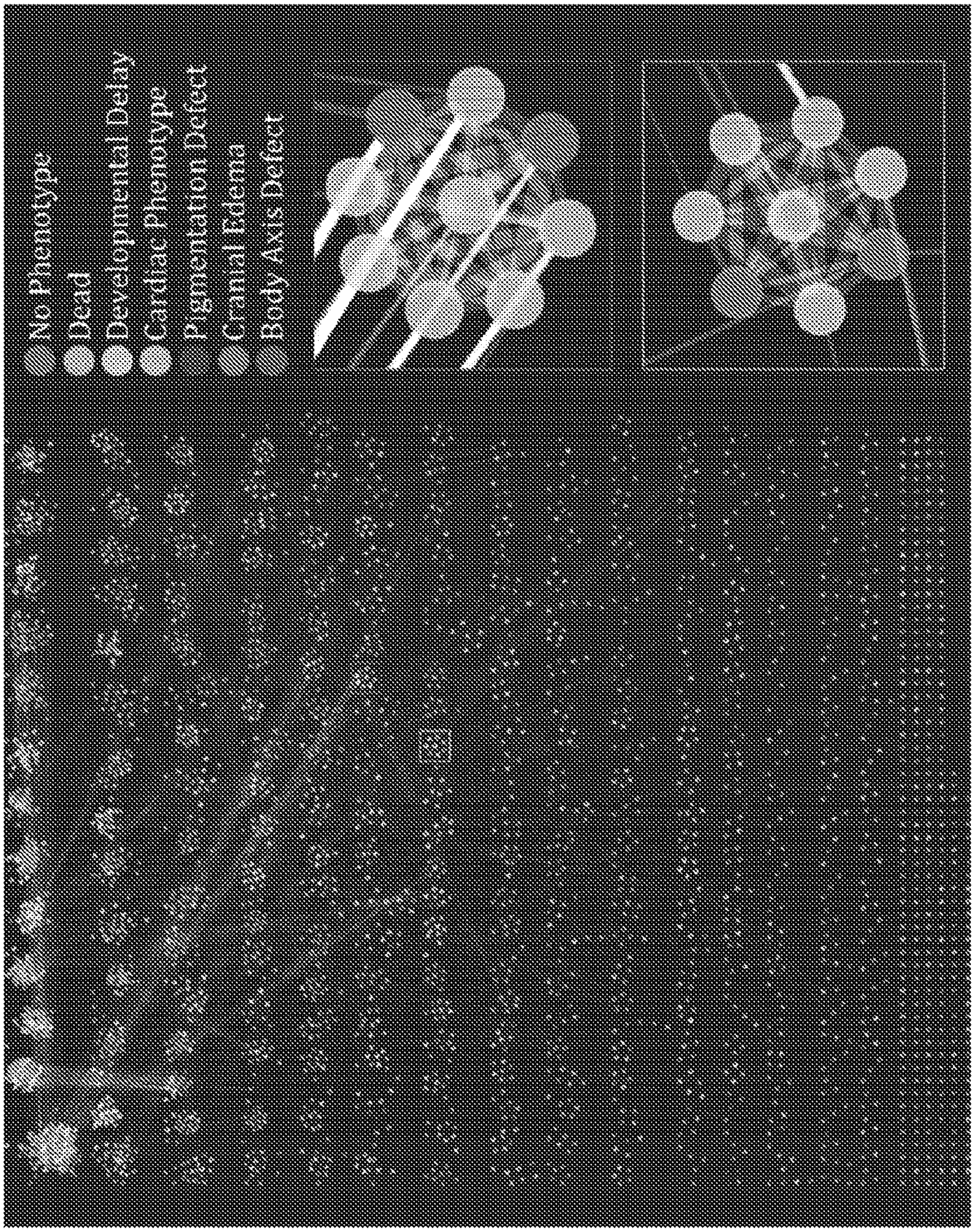

We first examined whether there was a systematic relationship between the chemical structures of screened compounds and the phenotypes associated with each compound. After computing pairwise similarity for all 4,182 screened small molecules, graph clustering was used to sort small molecules into groups based on shared structure (FIG. 2*d*; see Methods). While small molecules grouped together based on structural similarity did not display uniform phenotypic results (FIG. 2*c*, inset plots), they did have significantly higher similarity in phenotypic effect than would be expected based on random permutation (z-score 6.215, $p<0.0001$; FIG. 2*d*).

Figure 3:
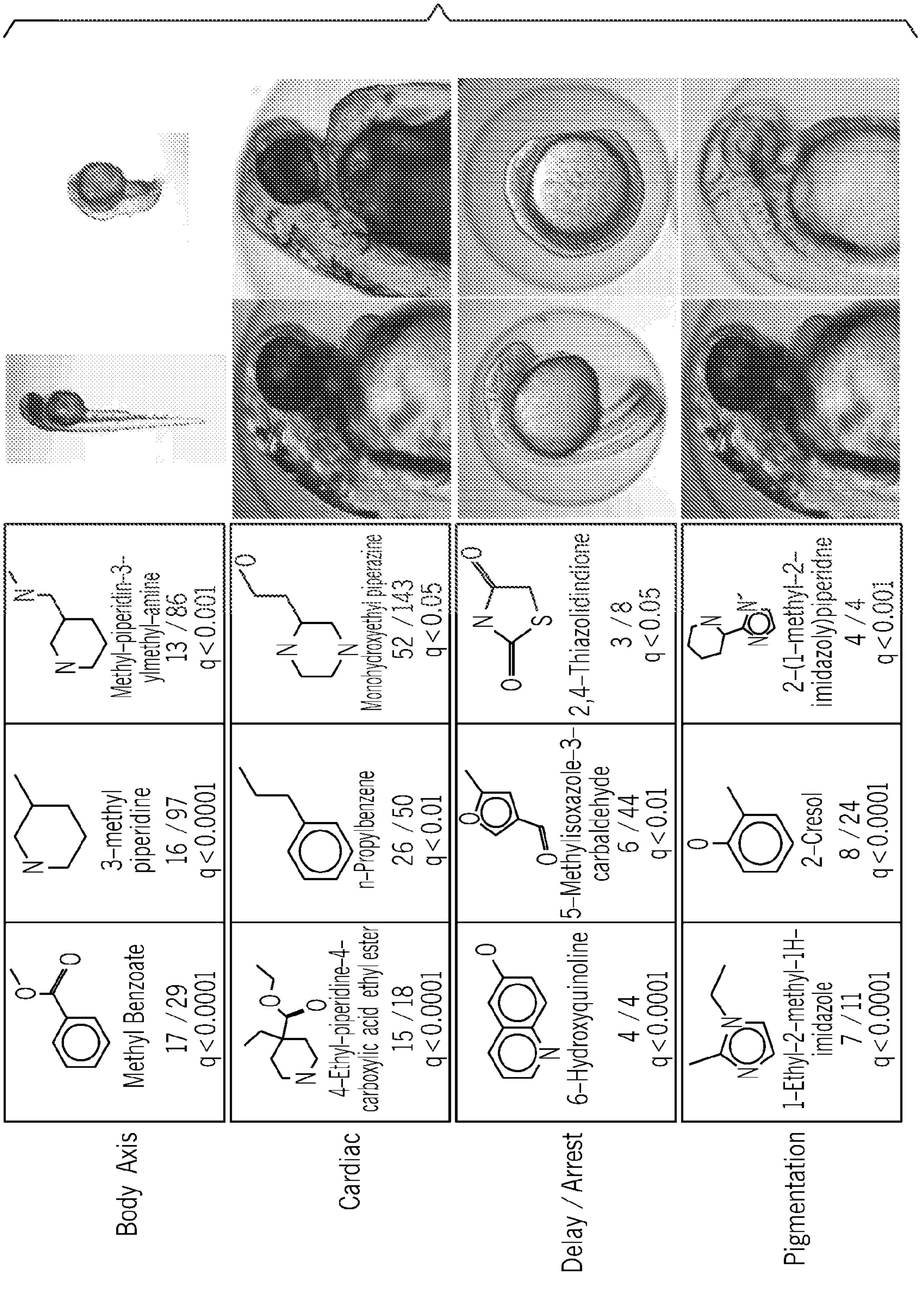
FIG. 3: Phenotype-specific sub-structure enrichment. Shown are molecular sub-structures enriched among screened yeast active compounds, for the given phenotype. In each row, control images are given on the left and exemplars of each phenotype shown on the right (images for cardiac, pigmentation, and body axis phenotypes were taken at 48 hpf, images for delay/arrest were taken at 24 hpf). Scores for each sub-structure indicate the number of compounds containing the given sub-structure that elicited the phenotype, as a proportion of the total number of compounds containing the sub-structure. P-values were determined using Fisher's Exact test and adjusted for multiple hypothesis testing using a Benjamini-Hochberg correction. The resulting q-value is displayed for each comparison.
Figure 5:
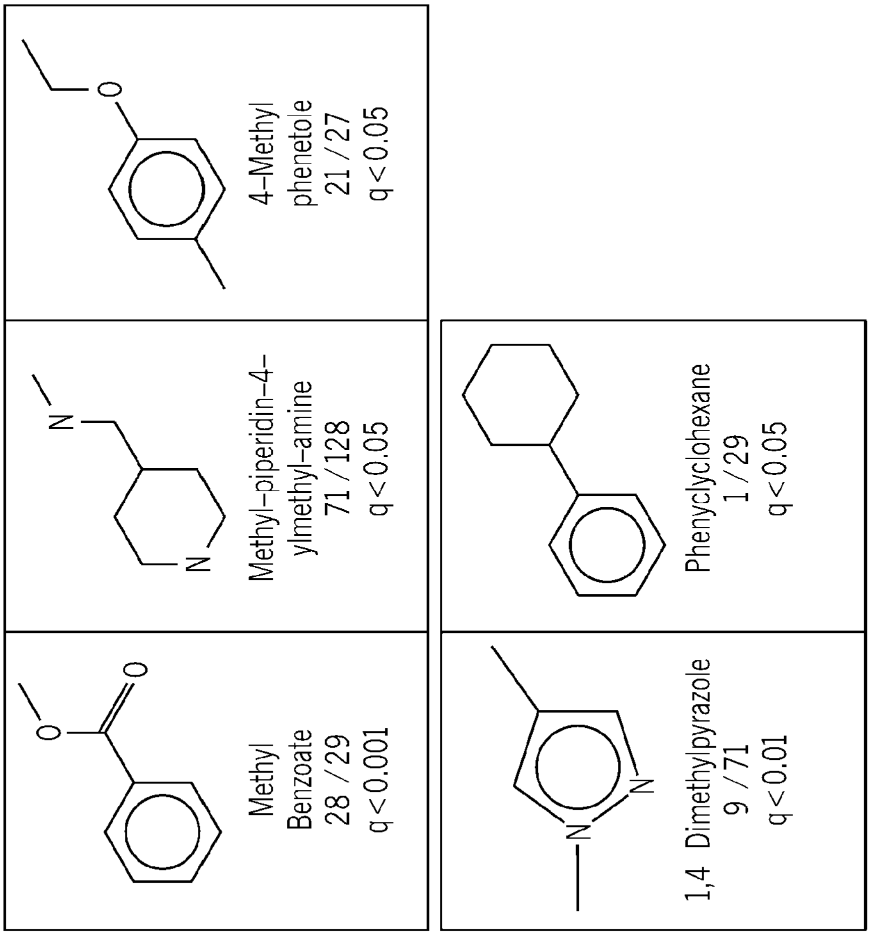
FIG. 5: Overall sub-structure enrichment. Displayed are molecular sub-structures enriched for yeast active compounds either causing any phenotype (positive enrichment), or no phenotype (negative enrichment). Scores for each sub-structure indicate the number of compounds containing the given sub-structure that elicited a phenotype, as a proportion of the total number of compounds containing the sub-structure. P-values were determined using Fisher's Exact test and adjusted for multiple hypothesis testing using a Benjamini-Hochberg correction. The resulting q-value is displayed for each comparison

Examining the chemical structures of compounds eliciting specific phenotypic effects it became clear that there were multiple chemical motifs capable of eliciting the same phenotype. Specifically, certain chemical substructures were consistently associated with some phenotypic classes (see U.S. Appl. No. 62/944,864 Table S2). For example, as shown in FIG. 5, 28 of 29 small molecules containing methyl benzoate produced a phenotypic response in embryonic zebrafish. Conversely, only 1 of 29 small molecules containing phenylcyclohexane caused any phenotypic effect, suggesting a reduced bioavailability, potentially either due to limited solubility in embryonic medium or reduced permeation through the chorion. Notably, this may result in a false negative result, as the bioactivity may be present, were the compound introduced via a different means. Particular molecular sub-structures were also significantly associated with specific phenotypic endpoints (FIG. 3). For example, 52 of 143 compounds containing monohydroxyethyl piperazine caused cardiac effects in zebrafish. Notably, piperazine is an anthelmintic with described effects on cardiac function in mammals[33], however a more detailed description of the zebrafish cardiac phenotypic response would be required before assertion that the zebrafish phenotype was occurring by the same mechanism as the human cardiac effects.

Figure 6:
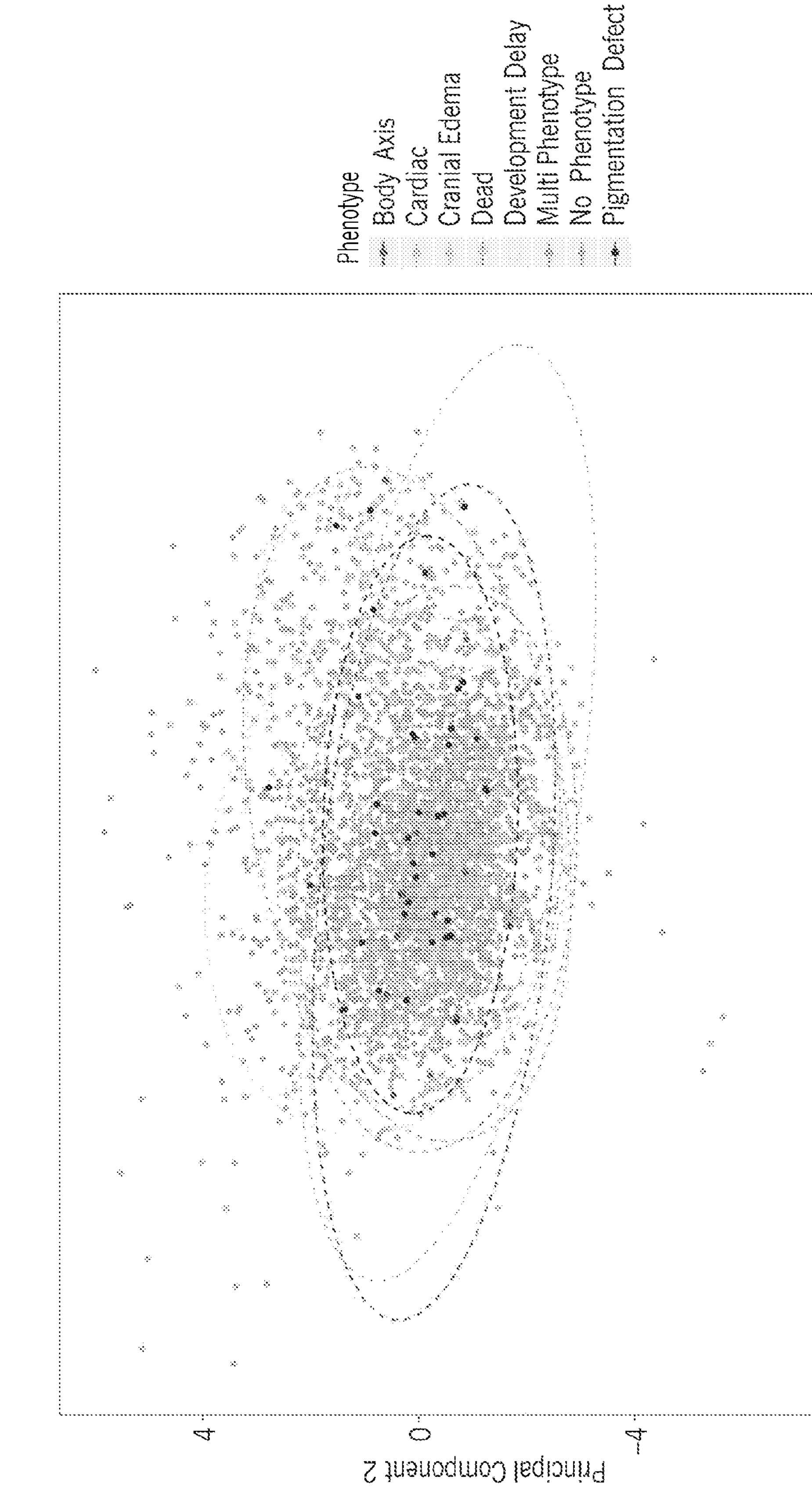
FIG. 6: Principal components analysis. Plot shows the 4,182 screened compounds with respective phenotypic classes indicated by color and respective ellipses. Compounds are plotted by the first (x-axis) and second (y-axis) principal components, showing minor physical-chemical separation of the phenotypic classes.

We next sought to determine whether the physical properties of screened compounds were unique among certain phenotypic classes. Small molecules causing any phenotypic effect had significantly lower molecular weights than non-active compounds, although this difference was modest in magnitude (MW=374.3 for active compounds, 379.4 for non-actives; $p<0.05$). Active compounds also had higher lipophilicity (mean log P 4.14 versus 3.95 for non-actives; $p<0.0001$; log P calculated as in Viswanadhan et al[34], see Online Methods) and lower polar surface area (44 $Å^2$ for active compounds, 46 for non-actives; $p<0.001$), but again, despite their statistical significance, these differences were modest in magnitude. Finally, we examined all screened compounds in the physical chemical space (as described previously[35,36]) using Principal Components Analysis (PCA; FIG. 6). The input to the PCA was all collected physical chemical properties (number of benzene rings, log P, total polar surface area, number of hydrogen bond donors, number of hydrogen bond acceptors, and molecular weight), and the resulting first two principal components were plotted (62.71% of the total variance explained). Examining the PCA plot, small molecules causing the same developmental phenotype appeared largely indistinguishable from others. Because neither structural nor physical properties of small molecules alone could strongly predict phenotypic effect, we sought to utilize models capable of incorporating both feature types.

Figure 7:
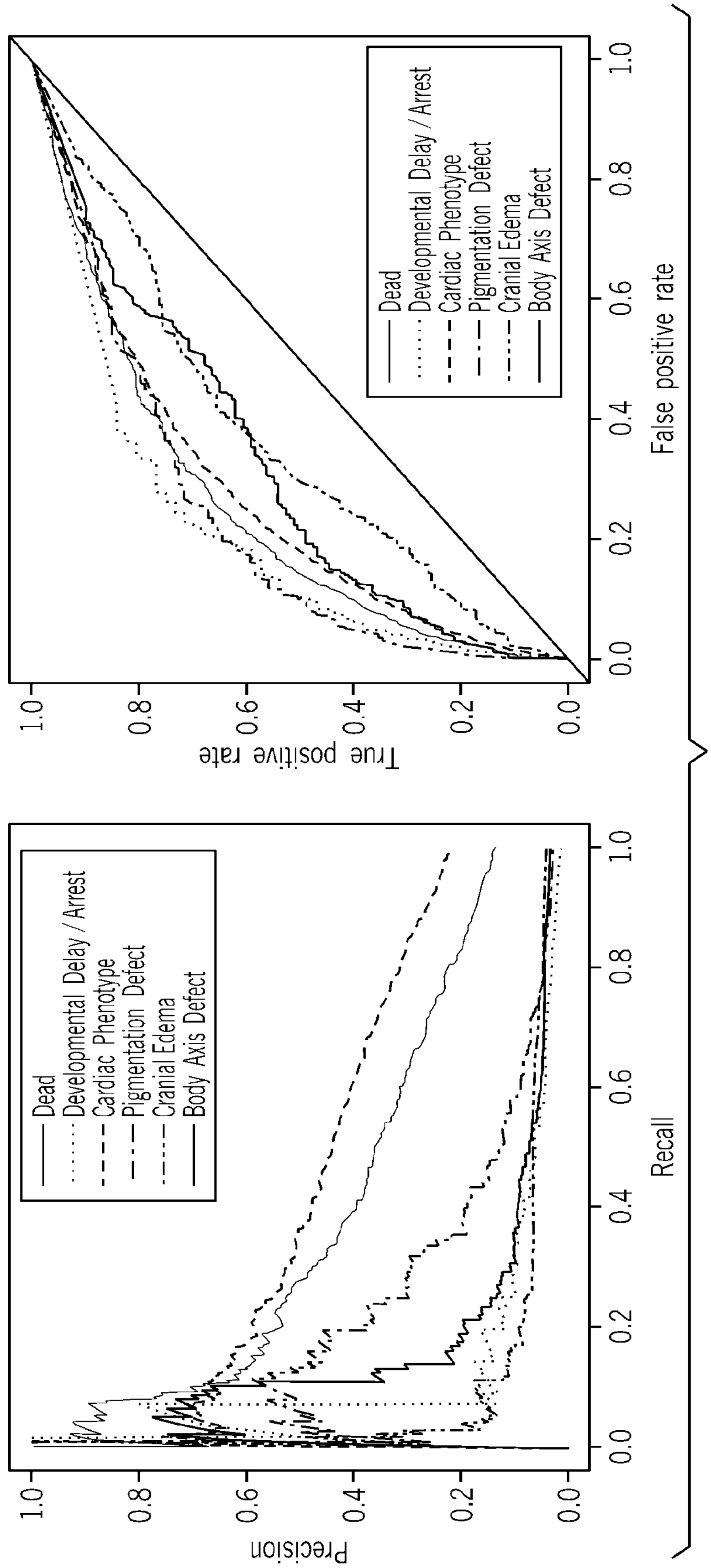
FIG. 7: Cross validation results. Shown are the performance estimates of the 6 Random Forest models by Precision/Recall plot on the left and Receiver Operating Characteristic (ROC) curve on the right (grey line indicates performance of a random classifier).

Example 3 Machine Learning Predicts Specific Phenotypes Using Structural and Physical Properties Given their known efficacy in compound classification and activity modeling[37], we used random forest ensemble classifiers to build models capable of predicting phenotypic effects for small molecules based on the combination of structural and physical properties (see Methods). For each of the six binary phenotypes chosen as prediction exemplars, the random forest classifiers out-performed a naïve prediction model based on structure similarity alone (see FIG. 7 and Table 6), below.

TABLE 6

Performance versus Naïve model.

| | Prior | Naïve | Random Forest |
|---|---|---|---|
| Dead | 0.092 | 0.251 | 0.538 |
| Cardiac | 0.219 | 0.362 | 0.577 |
| Body Axis | 0.033 | 0.074 | 0.206 |
| Pigmentation | 0.027 | 0.076 | 0.434 |
| Cranail Edema | 0.040 | 0.070 | 0.088 |
| Arrest/Delay | 0.007 | 0.050 | 0.152 |

Table 6 shows the expected performance of a random model (Prior association), the performance of a Naïve model based solely on identifying structural analogs (see Methods), and the performance of the Random Forest models based on structural and physical chemical properties for each phenotypic class. In each case, the Random Forest model out performs the Naïve model substantially. Performance is indicated by precision at 20% recall.

Random forest classifiers offer a natural way for features to be scored based on their importance in developing each model[38] (on the decrease in accuracy seen in trees generated without using each specific feature). Notably, each predictor ranked both structural and physical properties as being informative in phenotype prediction (see U.S. Appl. No. 62/944,864 Table S3). For example, the four most informative features for the classifier predicting body axis phenotypes included two molecular fingerprints as well as polar surface area and molecular weight. Thus, decision trees appeared to be based largely on combinations of the binary incorporation of molecular fingerprints, and size/polarity in specific threshold windows, allowing a more nuanced prediction than through either set of features alone.

Once generated, we used these models to predict additional, potentially active compounds, as has been shown to be possible following both phenotypic[39] and iterative focused[40-43] screening approaches. Once models were generated, we sought to identify the known activities of compounds predicted to elicit the major phenotypic outcomes that were observed empirically. Using our prediction models, we assigned confidence scores to the 56 million compounds assayable in the PubChem[30] library (see Methods). The phenotypic classes predicted included the six binary phenotypes described above (body axis, cardiac, pigmentation, cranial edema, death and developmental arrest) that were chosen as exemplars, phenotype-specific models (cardiac-only and pigmentation-only phenotypes, as well as death at 24 and 48 hours), and combinatorial models (cardiac and pigmentation, property of producing at least one or more than one phenotype). Collectively the models yielded 677,440,884 compound-phenotype predictions.

Figure 8:
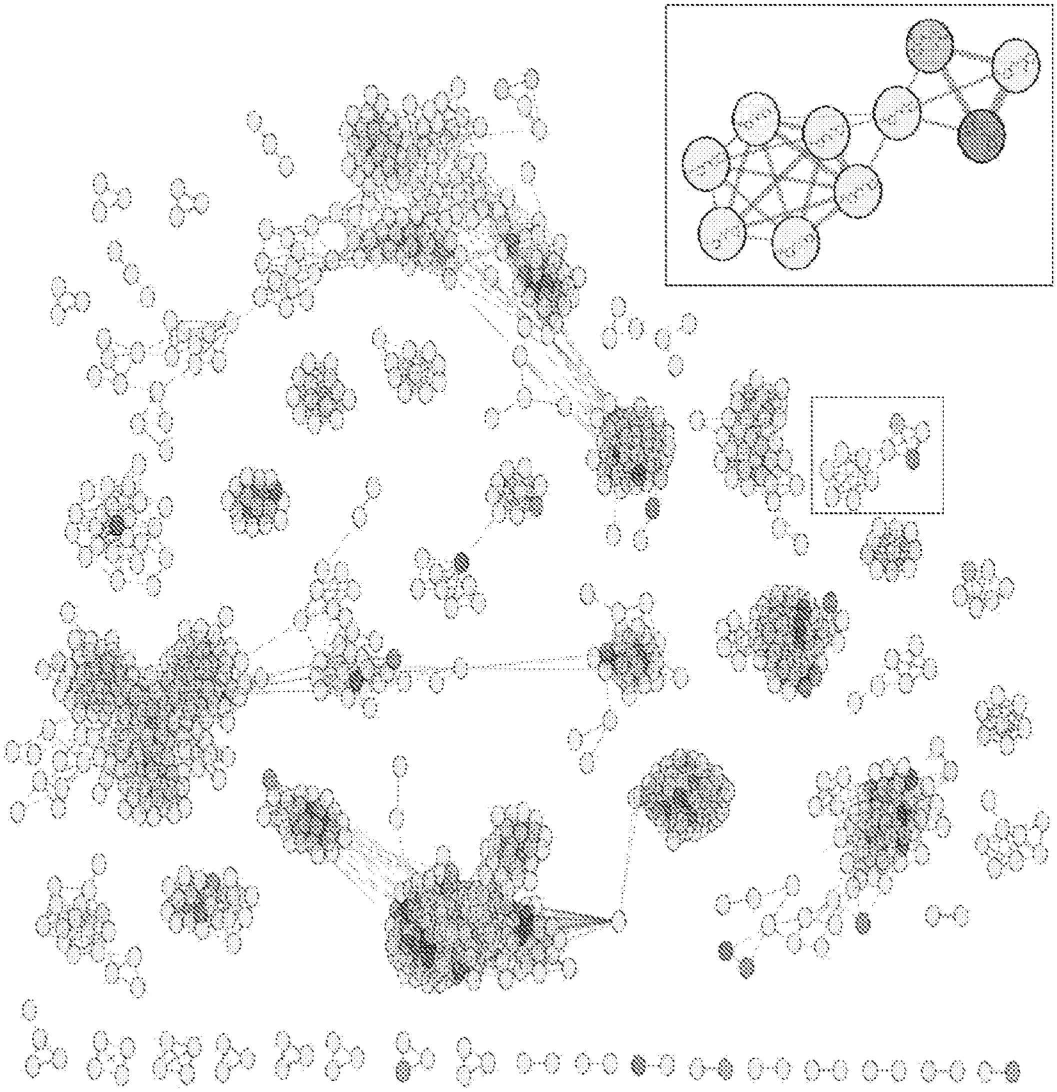
FIG. 8: Structural similarity and bioactivity among compounds predicted to kill embryonic zebrafish. Compounds passing the high-confidence (>0.8) threshold for the 'death' phenotype are displayed in this interaction graph with each of the 1264 compounds as a node, and structural similarity (Tanimoto coefficient>0.7) as edges. Bioactivity annotations from PubChem are displayed using all colors except light blue (default).

Despite the large size of the PubChem library, few (2,728) compound-phenotype associations achieved a high (>0.8) confidence score (FIG. 8, Table 7).

TABLE 7 phenotype and confidence scores

| Phenotype | Cutoff 0.5 | 0.55 | 0.6 | 0.65 | 0.7 | 0.75 | 0.8 |
|---|---|---|---|---|---|---|---|
| Body Axis | 542 | 343 | 166 | 98 | 55 | 31 | 18 |
| Cardiac | 15694 | 7828 | 4413 | 2668 | 1593 | 869 | 404 |
| Cardiac and Pigmentation | 85 | 36 | 10 | 0 | 0 | 0 | 0 |
| Cardiac Only | 3304 | 2387 | 1724 | 1172 | 754 | 393 | 160 |
| Cranial Edema | 288 | 203 | 2 | 29 | 5 | 3 | 3 |
| Dead 24 h | 407134 | 145902 | 271165 | 96923 | 28177 | 6527 | 1264 |
| Dead 48 h | 625491 | 255150 | 48087 | 13896 | 3772 | 1092 | 351 |
| Dead | 1528456 | 670623 | 90565 | 26928 | 7043 | 1803 | 487 |
| Delay Arrest | 274 | 186 | 94 | 45 | 22 | 10 | 7 |
| More than One | 1062 | 750 | 466 | 203 | 131 | 71 | 34 |
| Pigmentation | 82 | 47 | 110 | 46 | 18 | 10 | 0 |
| Pigmentation Only | 275 | 189 | 25 | 15 | 6 | 0 | 0 |

As has previously been observed, structure-activity models can be limited by the overall similarity between training and test sets[44]. Therefore, the small number of high confidence hits observed may be due to structural and physical differences between the training set, which had very specific physical and chemical properties (see above), and the PubChem Library. Notably, phenotypic classes with the largest training sets (Cardiac, Death) produced the largest number of high confidence predictions. We next examined each phenotypic class for enrichment in 250,873 published bioactivity assays[31] (see Methods, Table at FIG. 17). For cardio-active compounds, we noticed that stringency in phenotype definition affected described bioactivities. For example, compounds predicted to have a 'cardiac' phenotype with high confidence (>0.8) were significantly enriched (q<0.05) for activity in KCNH2 (HERG) assays. However, KCHN2 activity was not significantly enriched in compounds predicted to have a 'cardiac only' phenotype with high confidence, instead this group was enriched for compounds with D3 dopamine receptor antagonist activity. Notably, this may reflect dose sensitivity, and may be further discernable based on phenotypes not quantified here.

As anticipated for such a generic endpoint, compounds that were predicted with high (>0.8) confidence to kill zebrafish, whether at a non-specific stage ('death') or at more specific time-points ('death at 24 h', 'death at 48 h') showed multiple associated bioactivities (FIG. 8, Table at FIG. 17). This may represent a general cytotoxic effect of these compounds in cell-based assays. Notably, enriched bioactivities for the 'death' compounds were not limited to a subset of structurally related analogs (FIG. 8), emphasizing the strength of the in silico screening approach to identify shared bioactivity among diverse compounds. The high-confidence set of delay/arrest compounds did not show enrichment for any bioactivities; however, when relaxing the confidence cutoff (>0.6) we observed enrichment of delay/arrest compounds for cell-based activity against nuclear receptors NR2E3 and NR2F2/COUP-TFII, transcription factors that modulate discrete aspects of development[45]. Compounds predicted to elicit our least specific phenotypic category ('more than one') and our worst-performing phenotypic category ('cranial edema') as scored through cross validation of the random forest model were enriched for inhibitory activity of lytic granule exocytosis (cutoffs of 0.5 and 0.6, respectively), suggesting inconsistent or non-specific phenotypic effects of inhibiting this core set of physiologic processes.

While cross-validation estimates of predictor accuracy and known activities of phenotype-associated compounds were encouraging, we next sought to evaluate our predictors using an experimentally verifiable compound set. Specifically, each phenotype prediction model was used to assign a confidence score to the over 900,000 compounds in the ChemBridge commercial library based on likelihood to cause that respective phenotype (data not shown). It became clear that ranking by these scores also served to prioritize chemical analogs of compounds with known clinical application (Table 8; see Methods).

TABLE 8

Clinical uses of in silico screened compounds.

| Phenotype | Enrichment Term | NOM p-val | FDR q-val | FWER p-val |
|---|---|---|---|---|
| body axis | antineoplastic agents | 0 | 0 | 0 |
| Cardiac | Vasodilator agents | 0 | 0.002 | 0.002 |
| Cranial Edema | Detergents | 0 | 0 | 0 |
| Cranial Edema | Anti-infective agents, local | 0 | 0 | 0.001 |
| Dead | Herbicides | 0 | 0 | 0 |
| Dead | Anti-infective agents, local | 0 | 0.001 | 0.002 |
| Dead | Antioxidants | 0 | 0.003 | 0.011 |

Table 8 shows significant results obtained using Gene Set Enrichment Analysis (GSEA) to identify enrichment of known clinical uses of compounds predicted to elicit one of the 6 major phenotypic categories. Results are as obtained from GSEA, and include the nominal p-value (NOM p-val), q-value resulting from false discovery rate correction (FDR q-val) and q-value resulting from Family Wise Error Rate correction (FWER q-val).

For example, compounds that we had scored as being likely to cause cardiac defects were enriched for analogs of known vasodilator agents (FWER q<0.001), and compounds predicted to be lethal were analogs of known herbicides and antioxidants (FWER q<0.05). These findings are in keeping with previous observations regarding the utility of phenotype enrichment analysis for potential drug target and mechanism deconvolution[46-49], and strongly suggest that an agnostic zebrafish phenotypic platform can be used to annotate compounds with clinical and agricultural relevance.

To directly validate the predictions made on the 900,000 compound ChemBridge library, we experimentally re-screened the top 10 prioritized compounds for each phenotypic class and evaluated them in blinded fashion (Table 9).

TABLE 9

| Prediction and body phenotype observed | | | |
|---|---|---|---|
| ID | Prediction | Phenotype Observed | Hit |
| 22685803 | Body Axis | Most dead, remaining have small bodies | Yes |
| 52229810 | Body Axis | Dead(24 h) | No |
| 71349083 | Body Axis | Pericardial edema, no heart beat | No |
| 20494296 | Body Axis | Short, no heads | Yes |
| 56638922 | Body Axis | Small heads, short bodies | Yes |
| 86606851 | Body Axis | Some dead, alive have no head, necrotic | Yes |
| 26476480 | Body Axis | Weak heart beat | No |
| 39884980 | Body Axis | Most dead, some small with no hearts | No |
| 34105851 | Body Axis | Small body (no head) | Yes |
| 18809966 | Body Axis | Small body (appear dorsalized) | Yes |
| 87194463 | Cardiac | Dead (48 h) | No |
| 37690524 | Cardiac | Pericardial edema, no heart beat | Yes |
| 23490385 | Cardiac | Pericardial edema, no heart beat | Yes |
| 26410496 | Cardiac | Pericardial edema, no heart beat | Yes |
| 39911836 | Cardiac | Pericardial edema, no heart beat | Yes |
| 59314184 | Cardiac | Pericardial edema, no heart beat | Yes |
| 35983174 | Cardiac | Pericardial edema, no heart beat | Yes |
| 18069546 | Cardiac | Pericardial edema, no heart beat | Yes |
| 63198169 | Cardiac | Dying, pericardial edema | No |
| 38617825 | Cardiac | Dead (48 h) | No |
| 6942573 | Cranial Edema | Pericardial edema, no heart beat | No |
| 6944551 | Cranial Edema | Pericardial edema, no heart beat | No |
| 7008803 | Cranial Edema | slight discoloration | No |
| 21174986 | Cranial Edema | Pericardial edema, no heart beat | No |
| 23490385 | Cranial Edema | Pericardial edema, no heart beat | No |
| 19078129 | Cranial Edema | None | No |
| 13470943 | Cranial Edema | Dead(24 h) | No |
| 31472786 | Cranial Edema | Dying, pericardial edema | No |
| 99115299 | Cranial Edema | Pericardial edema, no heart beat | No |
| 63198169 | Cranial Edema | Dying, pericardial edema | No |
| 5246769 | Dead | None | No |
| 5745969 | Dead | Multiple severe phenotypes | No |
| 5931065 | Dead | Dead (48 h) | Yes |
| 6430515 | Dead | Dead (48 h) | Yes |
| 6432171 | Dead | Dead (48 h) | Yes |
| 7851920 | Dead | Multiple severe phenotypes, dying | Yes |
| 7861299 | Dead | Dead (48 h) | Yes |
| 7865333 | Dead | Dead (24 h) | Yes |
| 7872719 | Dead | Multiple severe phenotypes, dying | Yes |
| 7883437 | Dead | None | No |
| 44889923 | Delay/Arrest | Look 24 h at 48 h | Yes |
| 21652166 | Delay/Arrest | 5-10 somite stage at 48 h | Yes |
| 19759648 | Delay/Arrest | Bud stage at 24 h, dead at 48 h | Yes |
| 31551504 | Delay/Arrest | None | No |
| 59138912 | Delay/Arrest | None | No |
| 54305680 | Delay/Arrest | Bud stage at 24 h, dead at 48 h | Yes |
| 95188692 | Delay/Arrest | None | No |
| 65692859 | Delay/Arrest | Bud stage at 24 h, dead at 48 h | Yes |
| 45187255 | Delay/Arrest | Bud stage at 24 h, 5-18 somites at 48 h | Yes |
| 13197878 | Delay/Arrest | Bud stage at 24 h, dead at 48 h | Yes |
| 6108849 | Pigmentation | No pigmentation | Yes |
| 40726422 | Pigmentation | None | No |
| 85065584 | Pigmentation | None | No |
| 69904708 | Pigmentation | No pigmentation, | Yes |
| 31829597 | Pigmentation | 10-20 somites at 48 hpf | No |
| 38433186 | Pigmentation | No pigmentation | Yes |
| 13300080 | Pigmentation | No pigmentation, dying | Yes |
| 91866361 | Pigmentation | No pigmentation, cranial edema, slow heart beat | Yes |
| 23702187 | Pigmentation | No pigmentation, cranial edema, slow heart beat | Yes |
| 98334673 | Pigmentation | No pigmentation, cranial edema | Yes |
| 35983174 | Cardiac Only | Pericardial edema, no heart beat | Yes |
| 74596193 | Cardiac Only | Pericardial edema, no/weak heart beat | Yes |
| 18214265 | Cardiac Only | Dead (48 h) | No |
| 20489978 | Cardiac Only | Pericardial edema, no/weak heart beat | Yes |
| 33886139 | Cardiac Only | Pericardial edema, no/weak heart beat | Yes |

TABLE 9-continued

| Prediction and body phenotype observed | | | |
|---|---|---|---|
| ID | Prediction | Phenotype Observed | Hit |
| 14423654 | Cardiac Only | Pericardial edema, no/weak heart beat | Yes |
| 91267731 | Cardiac Only | Pericardial edema, no/weak heart beat | Yes |
| 19415191 | Cardiac Only | Pericardial edema, no/weak heart beat | Yes |
| 94082236 | Cardiac Only | Pericardial edema, no/weak heart beat | Yes |
| 85286054 | Cardiac Only | Pericardial edema, no/weak heart beat | Yes |
| 31829597 | Pigmentation Only | Developmental Delay | No |
| 98334673 | Pigmentation Only | No pigmentation, cranial edema | Yes |
| 6108849 | Pigmentation Only | No pigmentation, dying | Yes |
| 85065584 | Pigmentation Only | None | No |
| 13300080 | Pigmentation Only | No pigmentation, slow heart beat | Yes |
| 38433186 | Pigmentation Only | No pigmentation | Yes |
| 70713756 | Pigmentation Only | No pigmentation, cranial edema | Yes |
| 69904708 | Pigmentation Only | No pigmentation, cranial edema, slow heart beat | Yes |
| 60541916 | Pigmentation Only | None | No |
| 40726422 | Pigmentation Only | None | No |

Figure 9:
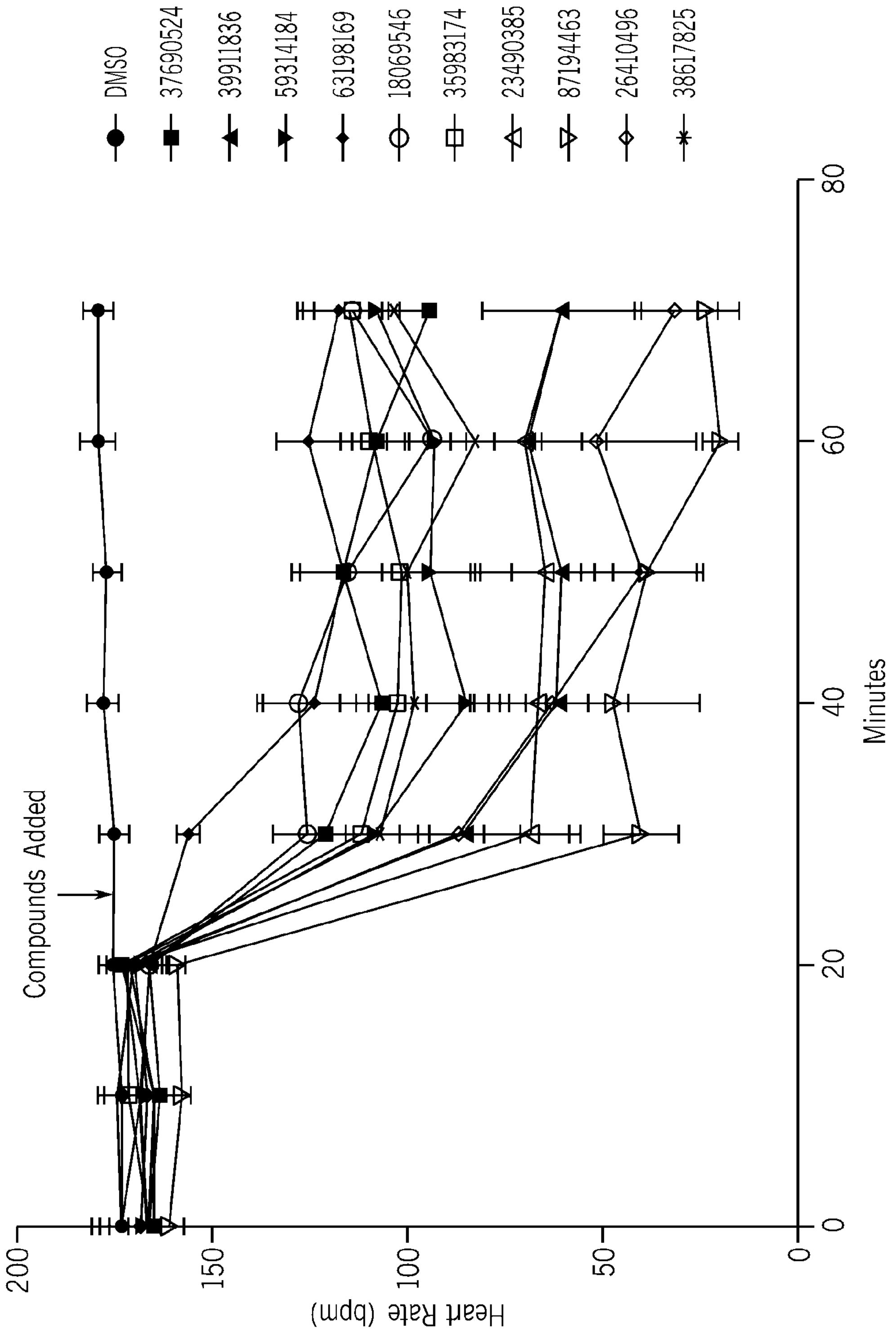
FIG. 9: Cardiac phenotype confirmations. The 10 compounds from the Chembridge library with the highest confidence score to elicit cardiac phenotypes were introduced at 10 uM to 48 hpf embryos. Heart rate was evaluated before and after compound or DMSO addition through manual measurement from bright field videos of each well.

The Chembridge "test" set was edited to exclude the yactive compounds, so none of the top 10 compounds for any phenotypic class had been evaluated at this point. For 5 of the 6 phenotypic categories (all except cranial edema), the 10 screened compounds were significantly enriched for the predicted phenotype (as compared to the phenotype rates seen in the yactive library, $p<0.05$; Fisher's Exact test). Examining the fidelity of these predictions, compounds predicted to elicit 'Body Axis', 'Cardiac', 'Death' and 'Delay/Arrest' were not significantly enriched for any other phenotypes, while compounds in the 'Pigmentation' prediction set were enriched also for appearance of cranial edema. This is unsurprising given the overlap of the cranial edema and pigmentation phenotypes in the training set. For the cardiac phenotype, in which acute affects can be quantified through assay of heart beat, we also found that all 10 compounds predicted to have a cardiac phenotype significantly reduced heart rate in 48 hpf embryos within 40 minutes of their introduction (FIG. 9).

For the case in which we did not observe the expected phenotype, cranial edema, failure in blind evaluations was foreseeable in that cross-validation for this model showed it to have both the lowest precision overall and the lowest relative increase in precision over the naïve, structure-based prediction model (Table 6, above). As with previous phenotypic models[50], this lack of precision appears to arise from noise in the initial observation of phenotypic data, as cranial edema was only observed in combination with other, more prominent, phenotypes. Consistent with this observation, we trained a second model to predict cardiac phenotypes using only compounds causing exclusively cardiac phenotypes as positive reference examples (i.e. excluding compounds that caused additional phenotypes; Table 9) and found that experimental performance improved. Specifically, we found that 9 of the 10 highest ranked compounds from the 900,000 ChemBridge library scored using this refined model had an exclusively cardiac phenotype ($p<1\times10^{6}$)

Figure 4A:
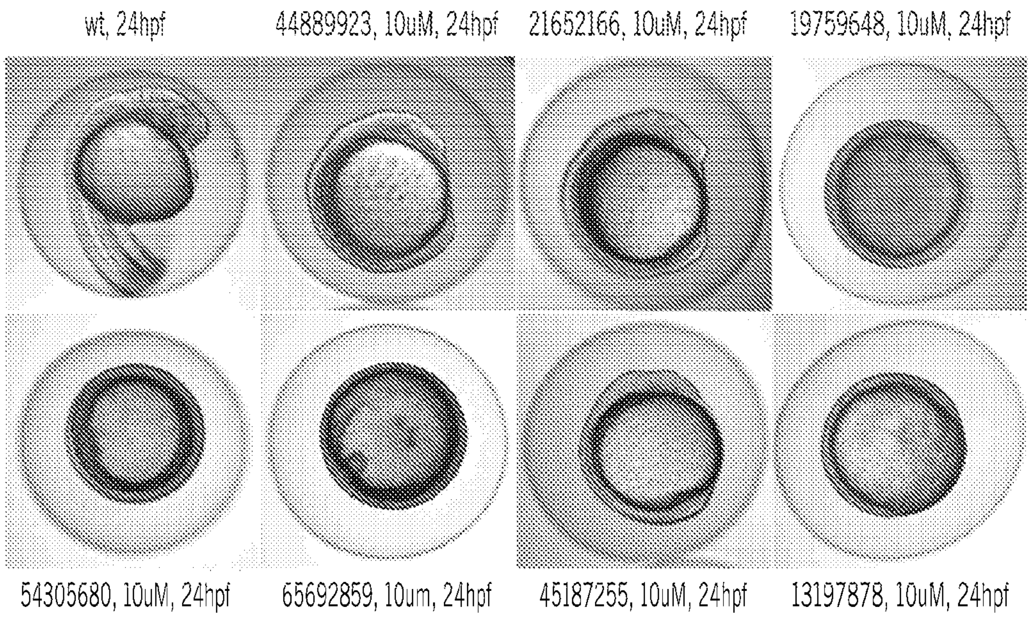
FIG. 4 (A)-(E): Function of delay/arrest compounds. 7 of the 10 compounds predicted as having a delay/arrest phenotype with the highest confidence caused obvious but divergent delay/arrest effects (A). For chemical structures associated with these Chembridge IDs see Figure S13. (www.chembridge.com). Some arrested development at shield stage, while others caused a slower developmental progression. One exemplar of this group, DA5 (ChemBridge ID 65692859—see FIG. 18) arrested development at any stage of early (<12 h) development (B). Analysis of oxygen consumption rate (C) showed a pattern of arrest for DA5 that differed from that seen upon inhibition of mitochondrial respiration through oligomycin A. DA5 was found to inhibit phospholipase D activity (D), with the product of phospholipase D, phosphatidic acid, showing rescue of the DA5 developmental arrest phenotype (E), suggesting the arrest phenotype to be due to a phospholipoase-dependent mechanism.
Figure 10:
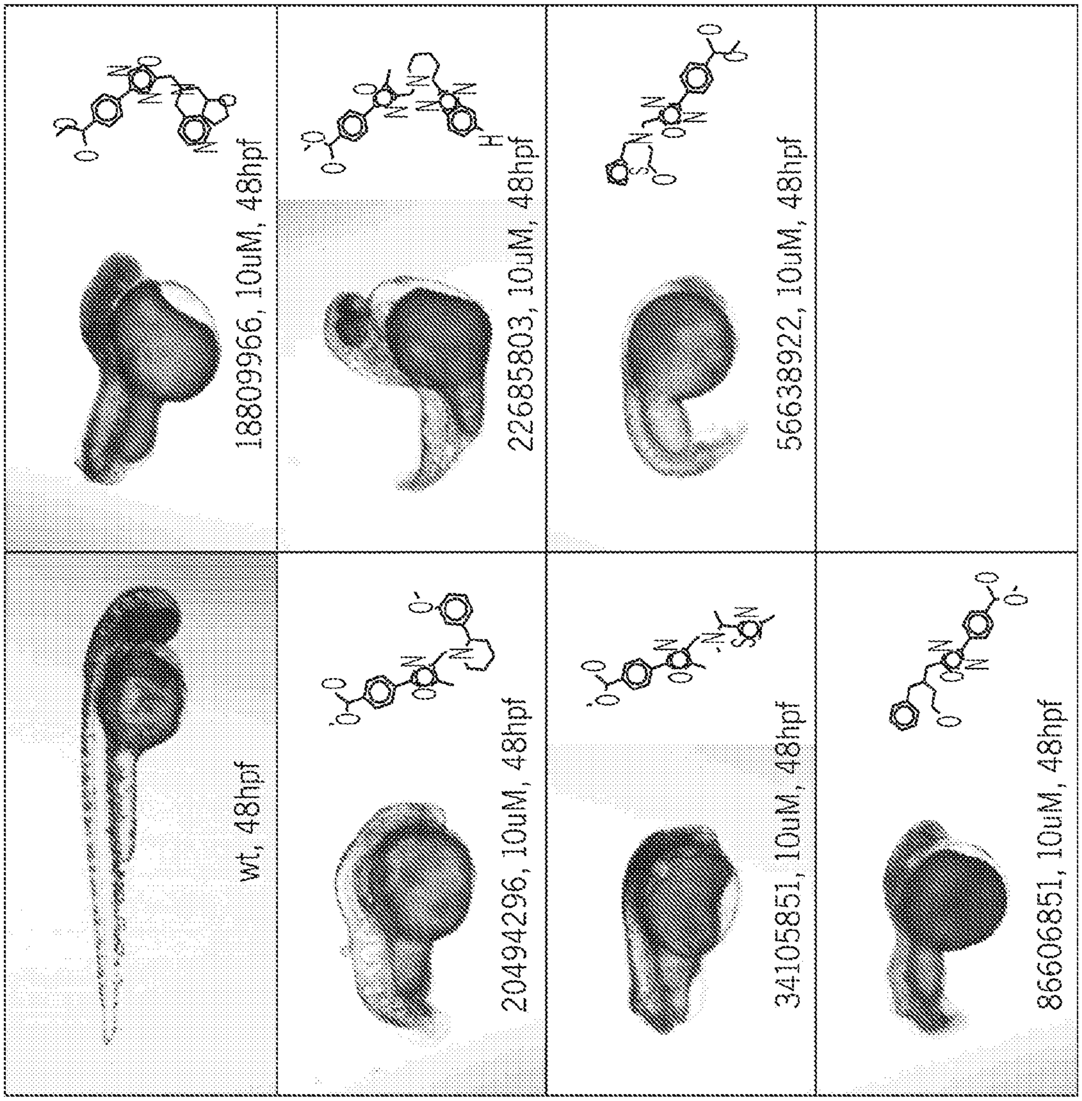
FIG. 10: Body axis phenotype confirmations. Shown are the 6 of the top 10 predictions from the ChemBridge library for the body axis phenotype that elicited the expected phenotypic effect. Compound identifiers are ChemBridge IDs.
Figure 11:
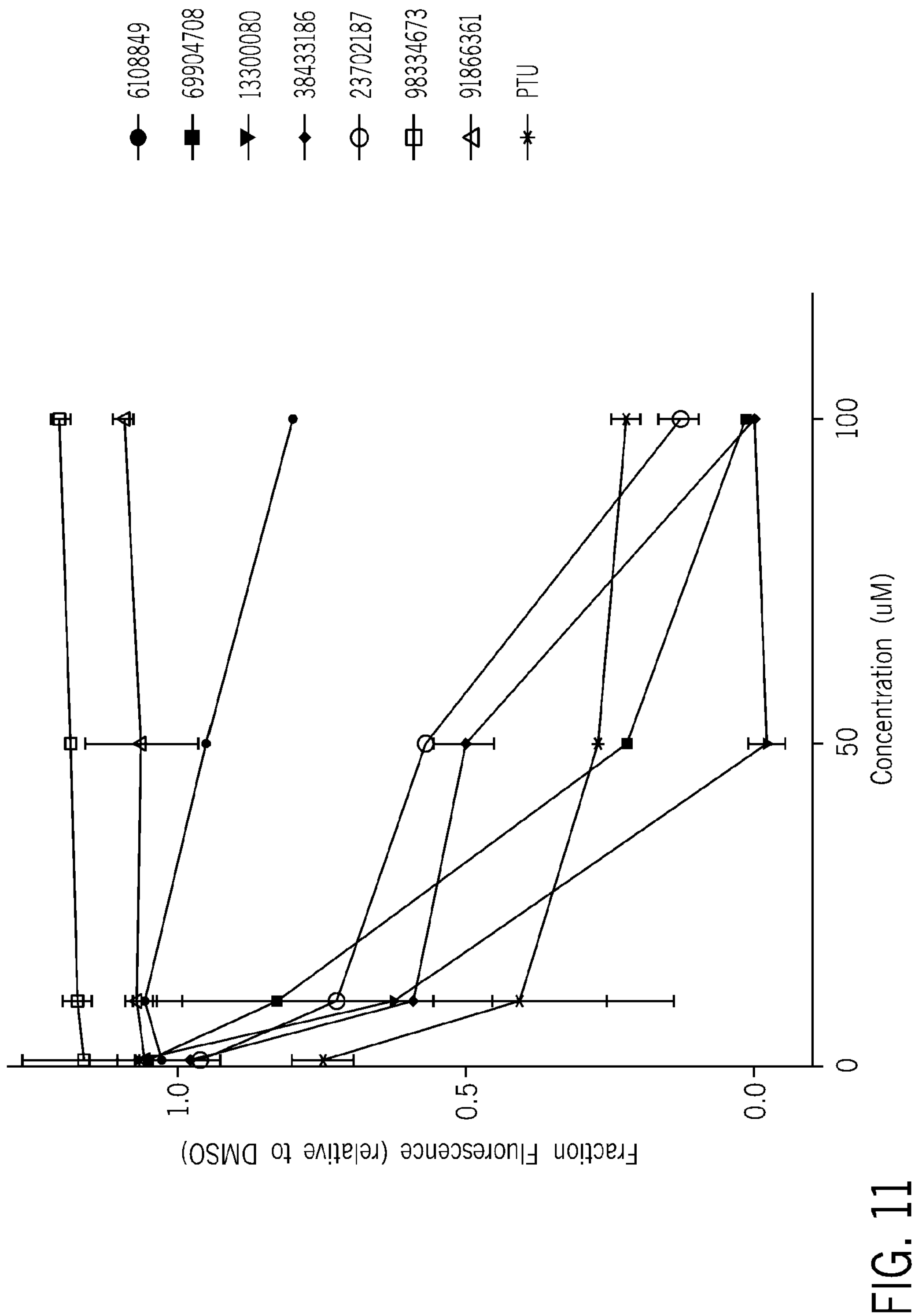
FIG. 11: In vitro tyrosinase inhibitory activity of pigmentation compounds. 7 of the top 10 compounds predicted to cause a pigmentation defect in embryonic zebrafish elicited the expected effect. In an in vitro assay, some of these 7 showed an inhibitory effect on the tyrosinase enzyme, which is required to convert tyrosine to melanin, while some showed no effect at all, suggesting a different mechanism of action.

Compounds predicted to affect development of the zebrafish body axis showed diversity in observed phenotypic effect. Specifically, while 6 of 10 predicted compounds did affect zebrafish body axis formation ($p<1\times10^{-5}$), the resulting effects appeared to be a combination of both dorsalization and ventralization of the body axis (FIG. 10). This likely reflects our lack of distinction in describing "body axis" phenotypes when assessing the initial training set. Similarly, while 7 of 10 compounds predicted to cause a pigmentation phenotype had the predicted effect ($p<1\times10^{-9}$), there was variation in the extent of melanocyte development evident after compound treatment. Of the seven compounds successfully predicted to have a pigmentation phenotype, five showed measurable tyrosinase inhibitory activity in vitro (two more so than PTU; FIG. 11), while the remaining two compounds exhibited no in vitro tyrosinase inhibition, suggesting their impact on pigmentation has an alternative mechanism. Finally, of the ten compounds predicted to cause developmental delay or arrest, seven did so upon screening ($p<1\times10^{-11}$) but did so at different developmental stages (FIG. 4*a*). This was likely a function of bioavailability, as we observed that even the same compound could have dose-dependent changes in the extent of developmental delay. Notably, all 10 compounds prioritized as potentially causing a delay/arrest phenotype had a similar molecular backbone (quinolines with an isoxasole group connected at the 6 position; FIG. 13). Because of the unique, dose-dependent nature of the delay effect, we chose to focus on this set of compounds for target identification.

Figure 4B:
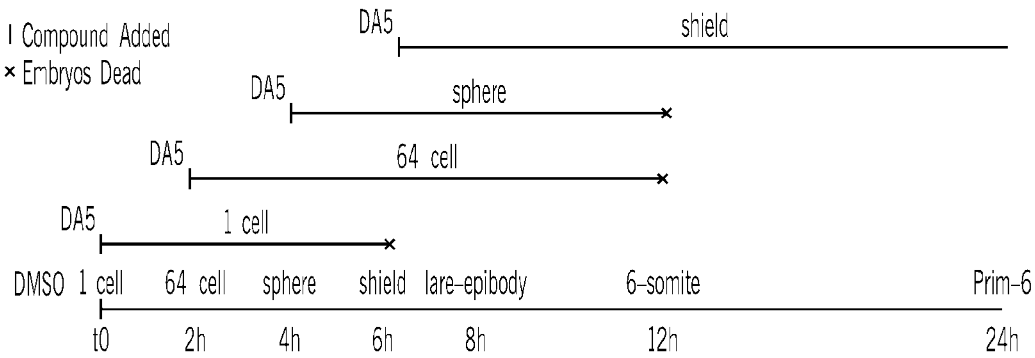

Example 4 Delay Arrest Phenotype Identifies a Novel Class of Phospholipase Modulators Given the high structural similarity between the class of compounds found to induce developmental delay/arrest (herein DA), we focused our experimental effort on one exemplar of this set (DA5: 6-([3-[(3,3-diethylpyrrolidin-1-yl)carbonyl]isoxazol-5-yl]methoxy)quinoline. DA5 caused sphere stage arrest when introduced in zebrafish embryo medium at 10 μM, and developmental delay when introduced at 5 μM (data not shown). Time course analysis (FIG. 4B) showed arrest up to and during gastrulation immediately after introduction of DA5, with mortality being almost immediate if DA5 was introduced in more developed embryos (24 hours post fertilization and beyond). While washout of DA5 did not allow embryos to recover, some other DA compounds did allow recovery when washed out (data not shown). We reasoned that this was likely due to differences in the target affinities of the various DA compounds.

Figure 4C:
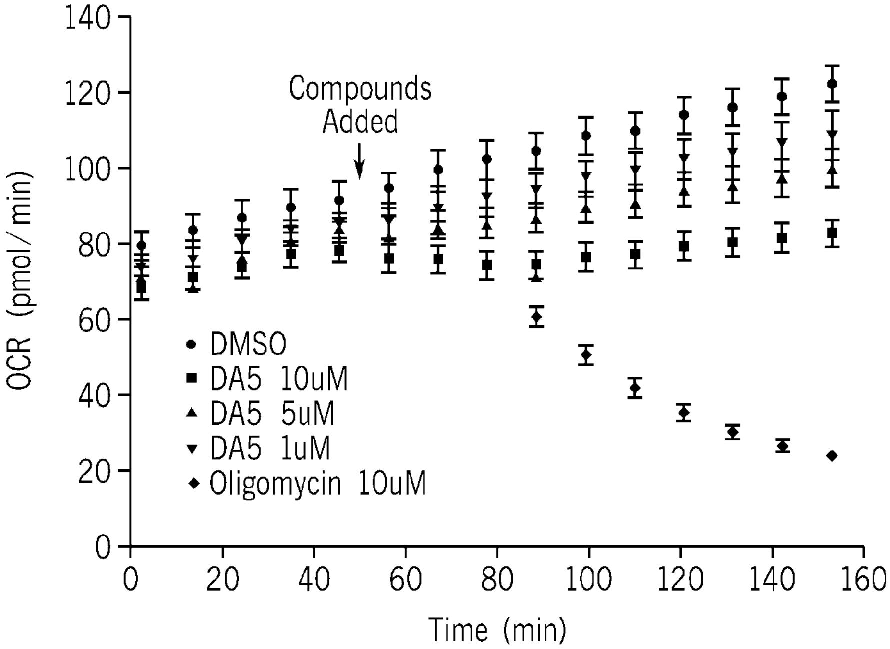
Figure 12:
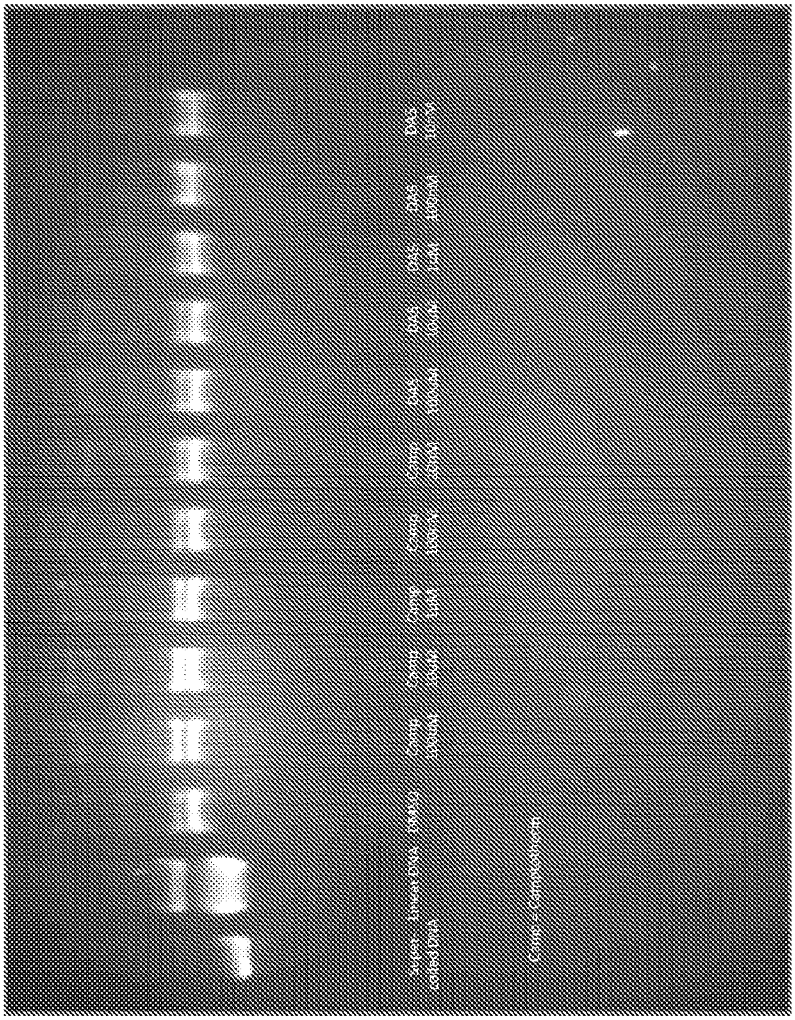
FIG. 12: Topoisomerase I and DNA binding assay for DA5. The effect of DA5 on Topoisomerase-mediated DNA unwinding is measured through a gel electrophoresis assay (see Methods). At concentrations up to 100 mM, DA5 appears to have no more effect on DNA cleavage than DMSO. By comparison, Camptothecin shows a dose-dependent effect on the amount of circular DNA present (upper band).

Developmental delay and arrest in zebrafish is a phenomenon known to occur upon oxidative stress, either via anoxia or inhibition of mitochondrial respiration[51,52]. However, measurement of respiration rate indicated that DA5 was not eliciting its effect through inhibition of mitochondrial respiration. Specifically, whereas introduction of oligomycin A (an inhibitor of ATP synthesis) caused an exponential reduction in respiration rate stabilizing at a baseline rate, DA5 treated embryos showed a consistent respiration rate (FIG. 4*c*). Conversely, while the respiration rate will steadily increase with growth over this same time period in control (DMSO treated) embryos (see FIG. 4*c*), this increase in respiration was attenuated in DA5 treated embryos. DNA intercalation analysis also suggested that the effect of DA5 was not due to DNA-binding or inhibition of Topoisomerase (TOPO) I (FIG. 12), a known effect of quinolines.

To further investigate this class of delay-/arrest-inducing compounds, we selected a compound from the yactive library containing the same core structure as the DAs (FIG. 18) and subjected it to genome-scale phenotype profiling in *S. cerevisiae*. More specifically, we used the haploinsufficiency profiling (HIP) and homozygous profiling (HOP) approaches (collectively termed HIP/HOP), which have been shown to provide insight into mechanism and genetic modifiers for a wide range of compounds[17]. The hit with the largest effect size was SEC14 (log 2 ratio of relative growth of 3.35 for control over SEC14 (formerly PIT1) heterozygous deletion strains in haploinsufficiency screening; data not shown), a phosphatidylinositol/phosphatidylcholine transfer protein involved in the localization of lipid rafts and essential for cell growth in yeast[53]. Notably, PIT1 is not essential for embryonic development in zebrafish[54], suggesting that while the HIP/HOP findings may lend mechanistic insight into the action of DA5, SEC14/PIT1 itself is likely not the molecular target causing the observed phenotype in zebrafish. To provide further insight regarding the potential target of the DA compounds, we next performed computational target prediction using the similarity ensemble approach[55] (SEA; online interface, default options selected) with the 10 highly-ranked delay/arrest compounds as input. SEA showed phosphodiesterases as being potential targets ($e<0.05$, data not shown). Since SEC14 demonstrates activity in concert with the phosphodiesterase phospholipase-D[56-59], we assayed DA5 for a potential inhibitory effect on phospholipases.

Figure 4D:
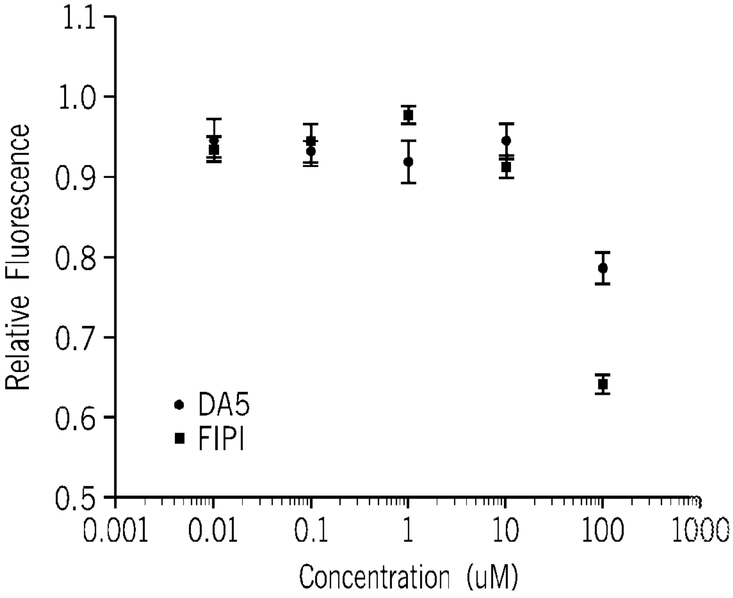
Figure 4E:
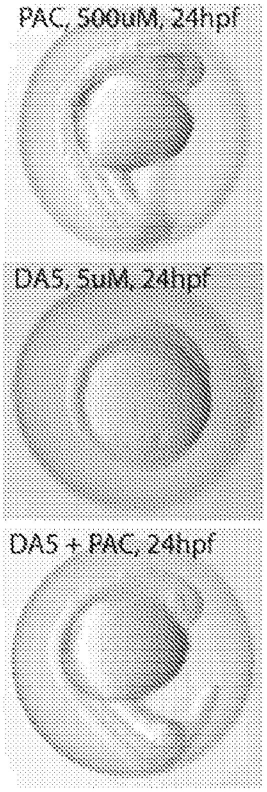
Figure 14A:
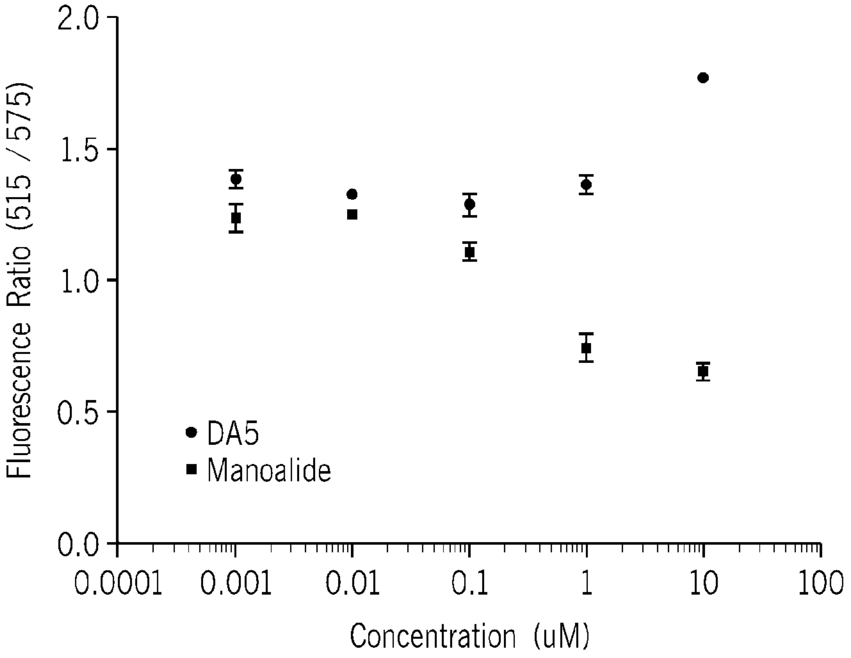
FIG. 14 (A)-(B): DA5 activates phospholipase A2 and C. The delay/arrest inducing compound DA5 caused an increased activity of phospholipase A2 (A) and phospholipase C (B) in vitro.
Figure 14B:
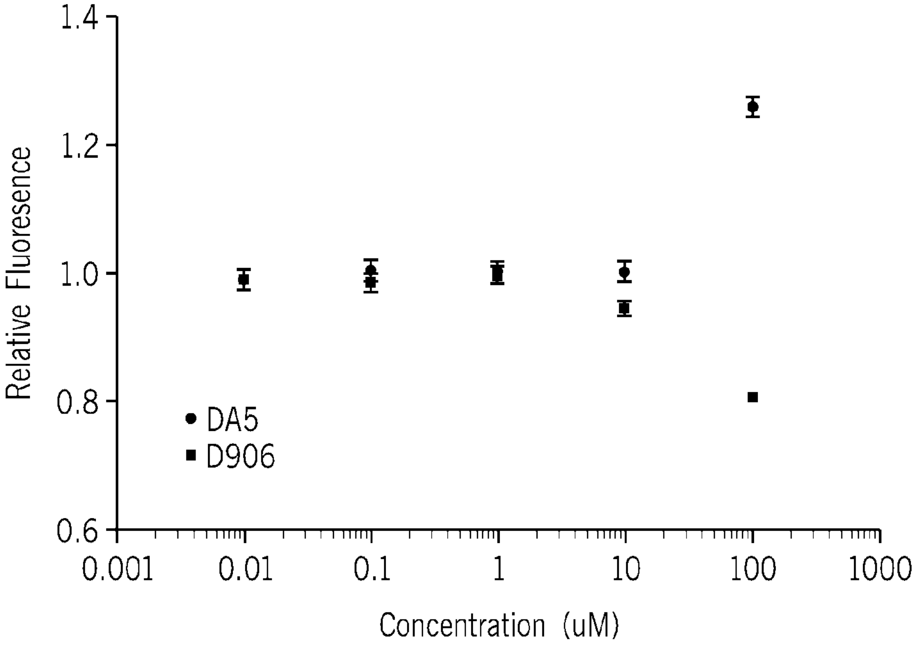
Figure 15A:
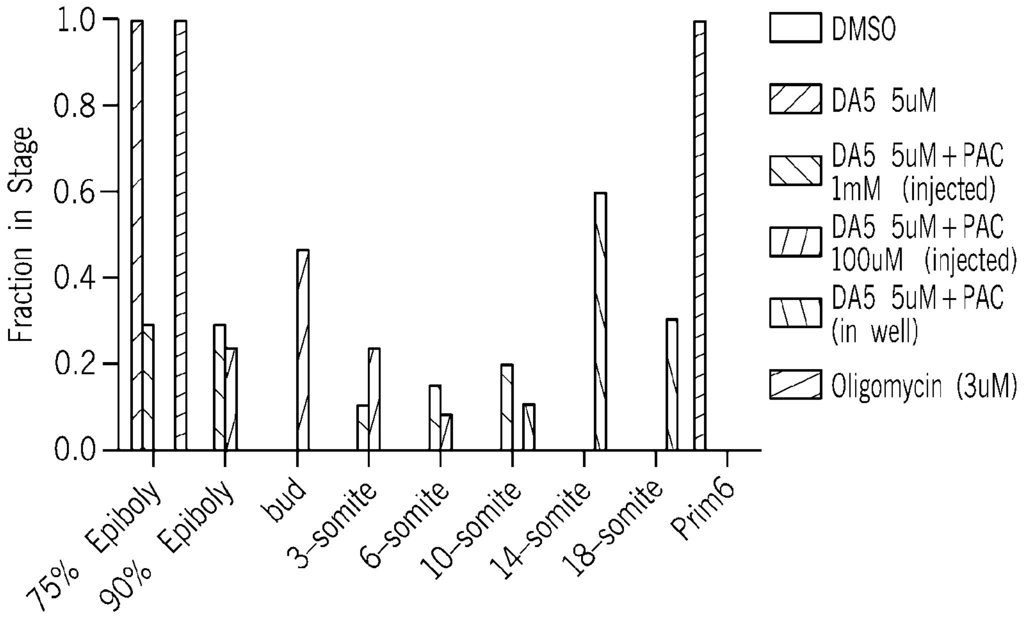
FIG. 15 (A)-(B): Effect of timing and injection on DA5 rescue. Rescue of the DA5 phenotype was compared using introduction of phosphatidic acid (PAC) in-well, versus injected into the embryo at the 1-cell developmental stage (A; DA5 introduced at 5 hpf). Also, to demonstrate that the rescue is not the effect of in-well binding of DA5 to PAC, DA5 was introduced at 5 hpf, PAC in-well at 24 hpf, and phenotypes surveyed at 36 hpf (B), with rescue still observed.
Figure 15B:
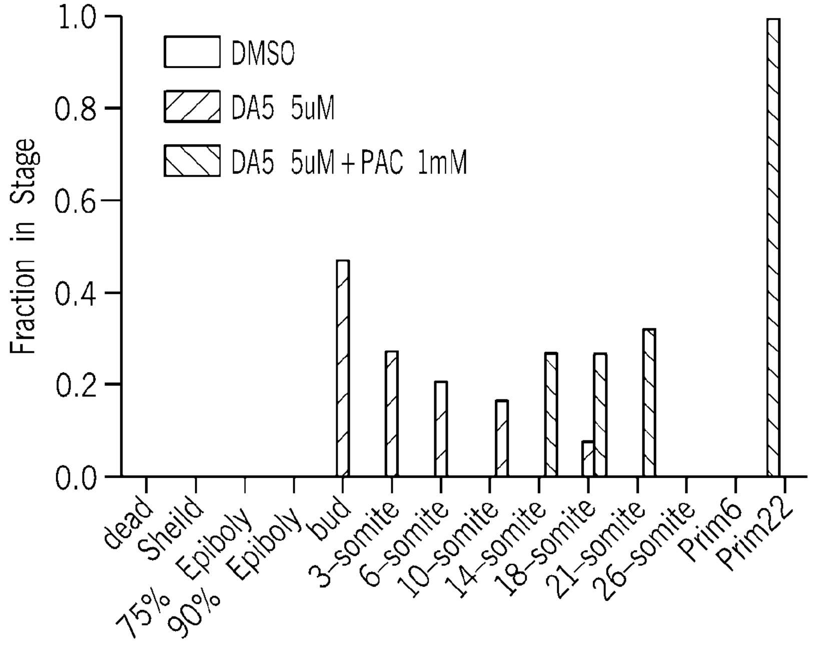
Figure 16A:
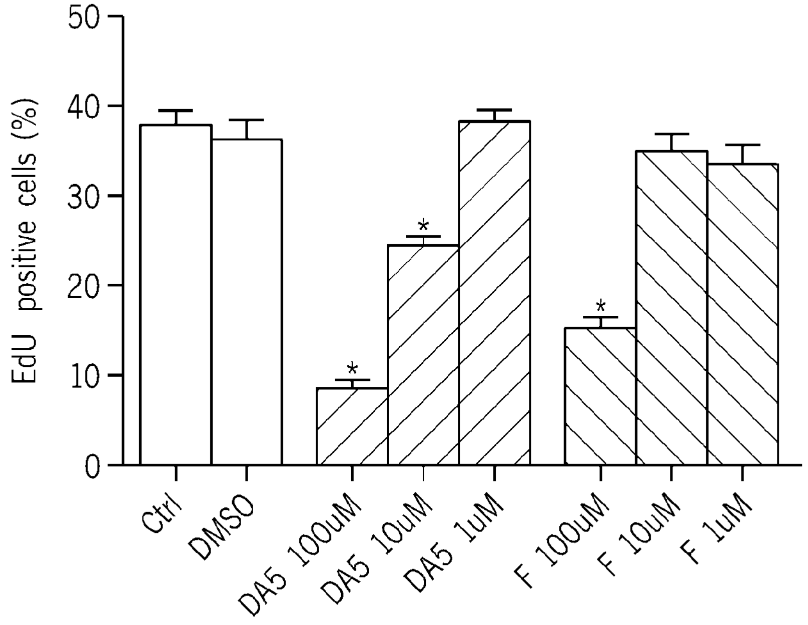
FIG. 16 (A)-(C): Effect of DA5 in human cell culture. Proliferation of osteoblastic cells was measured following introduction of DA5. Suppression of cell proliferation was found to be greater than that seen with positive control (c-Myc inhibitor 10058-F4; A), and as seen with 12 other randomly selected compounds eliciting other zebrafish phenotypes (B), whose structures are shown in panel (C) (all compounds shown in panel B were screened at 10 μM).
Figure 16B:
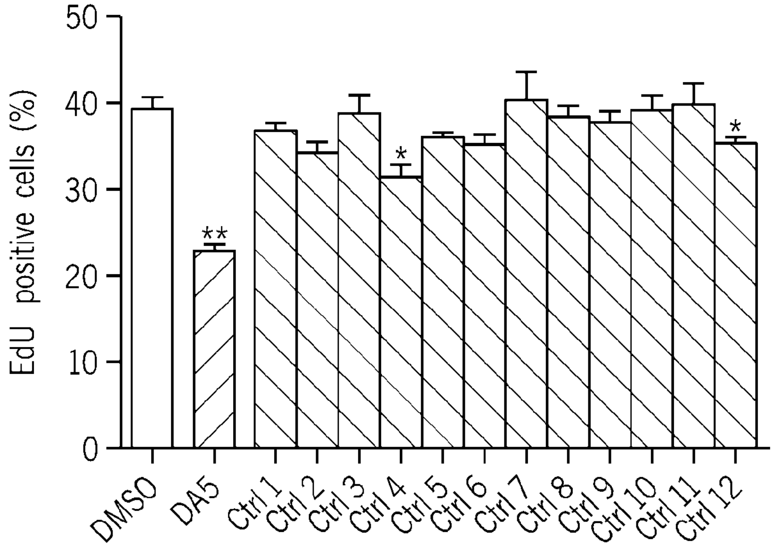
Figure 16C:
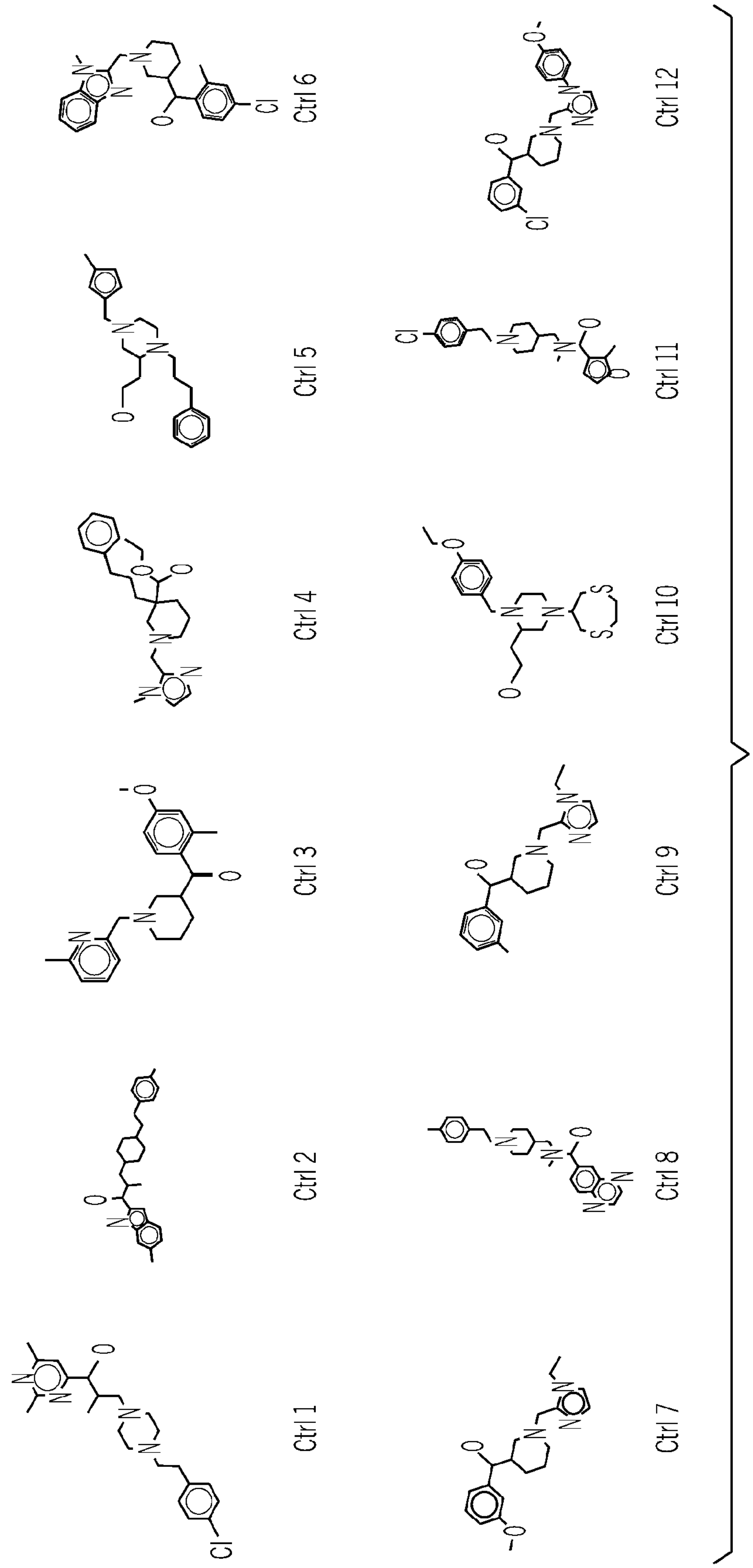

Using in vitro activity assays, DA5 was observed to cause a decrease in the activity of phospholipase D (FIG. 4*d*). Surprisingly, DA5 also increased activity of phospholipases A and C in vitro (FIG. 14), suggesting the capacity to potentially modulate the effect of multiple phosphatase classes in vivo. Phosphatidic acid (the product of phospholipase D) rescued the developmental delay phenotype of DA5 (FIG. 4*e*). We did not observe rescue of the DA5 phenotype with D-myo-Inositol-1,4,5-triphosphate (the product of phospholipase C). Phosphatidic acid did not rescue the phenotype of oligomycin A, suggesting that the rescue effect is not generalizable to compounds causing developmental delay/arrest through alternate means. Additionally, phosphatidic acid rescued the DA5 phenotype both upon injection and introduction in to embryonic medium, and at multiple time points after introduction of DA5 (FIG. 15 *a-b*) suggesting that the rescue effect is not due to reduced availability of DA5 in the medium. Given the known role of anoxia in cancer cell proliferation, we investigated the potential of the DA compounds to inhibit cancer cell growth in cell culture. We found a significant reduction in the proliferation of immortalized cells upon introduction of all DA compounds (FIG. 16).

Discussion

Traditional target-based drug discovery screens depend on the identification of lead compounds modulating a defined protein of interest. Leads can subsequently be evaluated and optimized for more general phenotypic effects (both efficacy and toxicity) in whole organisms and ultimately for clinical trial suitability. Phenotype-driven drug screens typically identify compounds capable of complementing or exacerbating a strictly-defined observable phenotype-ideally in the context of a known mechanism shared by the model and the disease. Here, using a phenotype screen in which observed outcomes were undefined at the outset, we were able to generate a varied initial seed set of compound-phenotype associations, which we used to perform over 700 million in silico phenotype association screens. Through manual re-screening of commercially available compounds, we demonstrate high reproducibility of confident small-molecule phenotype associations at an organismal level, identifying among others a class of compounds eliciting developmental arrest through an apparent novel phospholipid-dependent mechanism. This proof of concept study supports an overarching strategy of unbiased annotation of libraries with automated in vivo phenotypes used to narrow the chemical space for exploration and to accelerate drug discovery: critical prerequisites for the success of precision medicine.

In choosing the phenotypic endpoints for these initial experiments, we initially sought to characterize those binary endpoints commonly elicited by our compound library, and easily confirmed by independent, blinded observers. Notably, we do not necessarily view these phenotypes as having direct relevance to a human counterpart, but rather as cognate phenotypes that may integrate different potential bioactivities in humans. By design, some endpoints were readily recognized (e.g. body axis), while others were less readily identified on a consistent basis by observers (e.g. cranial edema). A more stringent approach with more explicitly defined quantitative phenotypic endpoints (including directionality of pigmentation, cardiac, or body axis phenotypes), computer vision, or potentially integrating effects on transgenic reporters, would increase the specificity of compound-phenotype associations in the training data, resulting in more accurate learners that could be iteratively improved upon. Nevertheless, these proof of concept experiments performed with phenotypes of modest information content establish the rigorous basis for continuously optimizable annotation of small molecule function using a learning system. This potential approach is exemplified by our focus on compounds targeting delay/arrest, in which an initially broad phenotype identified a novel class of compounds with a highly specific phenotype and a novel and potentially therapeutically relevant mechanism of action. This phenotype has not previously been actively screened, and highlights the relevance of broad multidimensional endpoints when they can be continuously optimized through machine learning. With enriched sets of vertebrate-active compounds, subsequent screens might be more focused on discrete chemical space and based on an initial set of annotations, so that only a modest number of small molecules would be require to be tested to complement or induce known gene-associated phenotypes (as has recently shown to be effective in therapeutic development[26]). The results of these screens can then be used to further seed in silico screening of much larger datasets, greatly expanding the set of tangible leads for the disruption of highly specific molecular targets.

Further improvements could come through a number of technical approaches including simple modifications such as creating dose response relationships at scale. While compounds were screened at a single concentration consistent with previous approaches, some molecules lethal at this concentration may have had more nuanced phenotypes at lower concentrations. Conversely, some inactive compounds may simply have not been able to meet the bioavailability threshold to elicit a phenotype. While 5 of our 6 individual phenotypic models performed well, future models based on data from improved criteria or obtained over a range of concentrations can likely improve on our results. Similarly, while screening the relatively small set of yactive small molecules ensured bioactivity of screened compounds, a more structurally diverse training set may have resulted in a larger number of high confidence phenotype predictions in the PubChem and Chembridge libraries[44].

Rather than relying on a single common lead structure or physico-chemical properties, our approach inherently exploits complex relationships between structure and physico-chemical properties to evaluate each candidate compound for specific phenotypic effects. Our approach is also more effective than a naïve model based on structural similarity alone. Relying on a combination of sub-structures and physico-chemical properties should also increase the potential for novel discovery beyond explicitly structure-based models, as structure-only models more faithfully recapitulate previously observed structure-activity relationships. Bioactivity analysis highlighted some notable properties of these in silico predictions. HERG is widely acknowledged as a prominent 'anti-target', causing severe cardiac side effects when inadvertently modulated by clinical compounds[60]. As a result, prediction of HERG activity is a major focus of preclinical toxicology[61]. The observation that high-confidence 'cardiac' compounds, and not 'cardiac-only' compounds are strongly associated with HERG activity suggests that a predictive model of such cardiotoxic activity could be readily trained using a fingerprint of zebrafish phenotypes.

The DA compounds highlighted here for their effects on developmental arrest are large quinolines. Quinolines have anti-malarial activity, although the mechanism is largely unknown[62]. While some quinolines can induce cell cycle arrest in cancer cell lines[63,64], typically this is due to DNA intercalation, which was not observed with DA5 (FIG. 12) This set of experiments identifies a novel, dose-dependent and reversible mechanism for the coordinated arrest of a broad set of biological processes. Rescue of the developmental arrest phenotype by phosphatidic acid suggests this mechanism to be lipid-dependent, implying a novel avenue for the programmable control of integrated biological processes, for example in organ procurement. An appropriate next step in the evaluation of these compounds would be assay of their effects in such a model.

While previous screening efforts typically examine large libraries to identify a small subset of compounds producing a phenotype or in vitro effect of interest, this study demonstrates the utility of defining class-specific activity patterns based on ensembles of compounds. The emphasis on whole-animal observation not only identifies compounds that are bioactive, but also demands that they be sufficiently specific to avoid global cytotoxicity or other non-specific pathway effects in vivo. While the in silico efforts described here applied these rules to a 56 million compound library, the largest we could obtain, this approach could have been applied to a much larger chemical space, limited only by computational hardware. Similarly, these results illustrate the feasibility of an in vivo phenotypic profiling platform, in which a substantial proportion of all potential biological characteristics are systematically and reliably quantified. We feel these results highlight that such an approach, while lacking the throughput of cell-based screening, could present a low-cost readout of in vivo efficacy and toxicity as the objective basis for prediction of precise clinical applications.

Methods

Zebrafish Husbandry and Compound Screening

Male and female wild-type (AB) fish were housed and embryos bred for screening using standard protocols. Embryos were collected in E3 solution (5 mM NaCl, 0.17 mM KCl, 0.33 mM $CaCl_2$), 0.33 mM $MgSO_4$) supplemented with 100 mM HEPES, put in 96-well plates at 3 embryos per well, and kept at 28.5° C. Compounds used were the commercially available subset of the 7,500 compounds identified by Wallace et al as inhibiting yeast growth[29] (4,182 total; ChemBridge). 10 mM compound stocks were diluted to 2 mM using DMSO, and 1 μL of each diluted compound solution was introduced into individual wells at 5 hours post fertilization (hpf) using a manual multichannel pipettor (10 uM final concentration). The first and last column of each plate received only DMSO, serving as negative control wells.

Phenotype Evaluation

Embryos were screened for a series of developmental phenotypes at both 24 and 48 hpf using standard light microscopy. At 24 hpf a single observer examined each well for embryo death or obvious developmental delay. Only those wells where at least two of the three embryos were dead or delayed were annotated as a hit for 24 hour death or delay/arrest, respectively. If any of the 16 control wells had evidence of a 24 hour death or delay/arrest phenotype, the plate was discarded. At 48 hpf two independent observers screened the plate, examining for embryo death, developmental delay, pigmentation defects, cardiac defects (pericardial edema, alterations in heart size, conduction, or contraction rate), jaw defects, cyclopia, and body axis formation defects. Again, only wells where multiple embryos exhibited the same phenotype (as scored by both observers) were taken as a hit for that phenotype.

Compound Similarity Analysis

Structural similarity among all compounds was calculated as the Tanimoto coefficient of FP2 fingerprints using Open Babel[65]. The resulting 4,182 by 4,182 matrix of similarity scores was then filtered to exclude all similarity scores below 0.7, and all self-matches. The filtered matrix was then clustered using the Markov Clustering algorithm[66] and visualized using Cytoscape[67]. The number of compounds appearing within the same cluster and having the same phenotype was then calculated for all clusters of size greater than 3 and summed to give an overall phenotype enrichment score to the cluster set. The resulting score was then compared against that from each of 100,000 randomly-derived cluster sets drawn from the same initial compounds and using clusters of identical size (i.e. label shuffling). An empirical p-value was calculated as the number of times a randomly-derived compound set scored better in phenotype co-clustering than the true compound set, divided by the total number of iterations (100,000). For maximum common substructure (MCS) analysis, the MCS was identified using the ChemViz plugin for Cytoscape[67].

Machine Learning and Compound Prioritization

A separate random forest ensemble classifier was trained for each of the 6 most commonly observed binary phenotypes: death (24 or 48 hours post fertilization), cardiac effects, pigmentation, body axis defects, delay/arrest, and cranial edema. In each of the six models, small molecules causing the given phenotype were used as positive training examples, and all remaining small molecules were used as negative training examples. Feature data used for classification included: molecular fingerprints, total polar surface area, molecular weight, log P, number of rotatable bonds, number of hydrogen bond donors, and number of hydrogen bond acceptors (all calculated using plugins of the JChem Suite (http://www.chemaxon.com)). The learning procedure then identified patterns in physical properties (e.g. molecular weight, log P, polar surface area) and structural properties (presence or absence of any of several thousand small molecular fingerprints) that could be used in combination to predict activity. Accuracy of the six predictors was evaluated through 'out of bag' (OOB) scoring (i.e. compounds are assigned scores using only models that had not been trained using information for that gene), and resulting receiver operating characteristic (ROC) curves plotted using the ROCR package[68] for R.

The 6 trained learners were then used to predict the likelihood that each of the 919,683 currently commercially available compounds in the ChemBridge library may cause the given phenotype (this list excludes the 4,182 compounds initially screened). Resulting scores for each phenotype were used to rank the over 900,000 compounds. Enrichment for compounds with high (>0.95) similarity to known therapeutics (defined using Tanimoto Coefficient of molecular fingerprints) was calculated for each of the 6 ranked lists using gene set enrichment analysis[69]. The top 10 highest-ranking compounds from each of the 6 lists were screened as described above, blinded and in duplicate.

Screening in Human Cell Lines

Human osteosarcoma cells (U-2 OS) were obtained from ATCC (HTB-96) and re-suspended in McCoy's 5a medium (ATCC 30-2007) containing 10% FBS and penicillin/streptomycin. Cells were passaged at least 5 times before use in proliferation assays. To perform the proliferation assay, cells were trypsinized using standard protocols, plated at 1000 cells per well in 96-well clear-bottom black cell culture treated plates, and allowed 24 hours to attach. Compounds of interest were dissolved in DMSO and introduced at an overall DMSO concentration not exceeding 0.1% by volume. Four hours after drug introduction, cells were stained and fixed using the protocol described in the Click-iT EdU Alexa Fluor 488 Imaging kit (Thermo Fisher), with Hoescht staining used to identify total cell numbers. Each well was imaged using a Nikon Eclipse Ti Epifluorescent microscope with automated stage and counts of dividing and total cells were obtained in an automated fashion using Nikon's NIS Elements software. Percent of dividing cells reported is the result of at least 4 replicates. Controls were given the same DMSO concentration by volume as compound-treated wells.

HIP/HOP Screening

Haploinsufficiency profiling (HIP) and homozygous profiling (HOP) of yeast strains was performed as previously described[70]. Briefly, the tagged yeast deletion collection[16] obtained from Angela Chu at the Stanford Genome Technology Centre was grown such that 20 μL of saturated media containing each strain was combined to produce two pools: one containing the 1194 distinct heterozygous mutants, and the other containing the 5054 homozygous strains. 700 μL of pooled cultures were grown at 30° C. in the presence of enough of the compound of interest to cause a 10-20% decrease in wild-type growth rate. 0.7 $OD_{600}$ of the heterozygous pool and 1.4 $OD_{600}$ of the homozygous pool were extracted after 20 and 5 generations of growth, respectively. DNA was isolated as previously described[71], amplified using primers containing the sequences of the common barcode primers and sequences required for attachment to the SOLiD slide, then sequenced using SOLiD sequencing. To analyze the resulting data, all counts were quantile normalized such that each experiment had equivalent count distributions. Fitness defect ratios for each strain were then calculated and expressed as the log 2 ratio of control to treatment (as in Smith et al[70]).

Respiration Rate Analysis

Analysis of embryonic respiration was performed using a Seahorse XF24 analyzer (Agilent). Embryos at 5 hours post fertilization were arrayed in E3 media at 3 per well in a 24-well standard Seahorse plate using an isolating mesh (as in Stackley et al[72]). Each plate contained four replicates of each indicated compound of interest, as well as 4 control wells receiving the equivalent DMSO as contained in the indicated compound solution, and 4 wells with no embryos present to act as a baseline for oxygen content of the media. The sample baseline was read for 5 cycles (3 minute mix, 2 minute wait, 5 minute measure), then compounds were introduced in a single 40-cycle injection phase (3 minute mix, 2 minute wait, 5 minute measure). Measurement data were exported using Seahorse software (Agilent) and averaged over 3 experimental days.

In Vitro Activity Assays

Phospholipase D, C, and A2 activity were measured in vitro using commercial kits. For Phospholipase D, the Amplex Red Phospholipase D Assay Kit (Thermo Fisher) was used with Phospholipase D (*Streptomyces chromofuscus*—Enzo Life Sciences) added, and FIPI (4-Fluoro-N-(2-(4-(5-fluoro-1H-indol-1-yl)piperidin-1-yl)ethyl)benzamide, 5-Fluoro-2-indolyl deschlorohalopemide) hydrochloride (Sigma) acting as a positive control. To assay Phospholipase A2 activity, we used an EnzChek Phospholipase A2 Assay kit (Thermo Fisher) with Manoalide (Santa Cruz) as a positive control. To assay Phospholipase C activity, we used an EnzChek Direct Phospholipase C Assay Kit (Thermo Fisher) with D609 (Sigma) as a positive control. Tyrosinase activity was measured using a colorimetric Tyrosinase inhibitor screening kit (BioVision) with PTU as a positive control. For each assay, solutions were prepared in 96-well black clear bottom plates and read using a FLUOstar Omega plate reader at the wavelengths recommended by the respective manufacturers, with each measurement representing the average of at least 4 plate wells.

DNA Binding 0.5 ug of pHOT-1 supercoiled DNA (TopoGEN, Inc. TG2030-2) was combined with 2× Topoisomerase I assay buffer (50 mM Tris-HCL (ph7.9), 1 mM EDTA, 1 mM DTT, 20% (v/v) glycerol, 50 mM NaCl), nuclease free water and either DMSO vehicle control, m-AMSA positive control (100-1000 uM; TopoGEN, Inc. TG4150) or DA5 (0.01-100 uM) as appropriate in 28 ul reactions, then incubated for 5 minutes at room temperature. 2 ul of 2 U/ul recombinant human Topoisomerase I (TopoGEN, Inc. TG2005H) was added to treatments corresponding to lanes 3-12 with 2 ul of dilution buffer (5 mM Tris-HCL (pH 7.9), 1 mM EDTA, 1 mM DTT, 50% (v/v) glycerol, 500 mM NaCl) added to control treatments lacking enzyme (lanes 2, 13 and 14). Reactions were mixed and incubated at 37° C. for 30 minutes. Reactions were terminated with the addition of 20 ul nuclease free water and 50 ul of 1-butanol (water-saturated) followed by vortex and centrifugation at 13,000 rpm for 1 minute. The lower aqueous phase was removed and added to 50 ul chloroform/isoamyl alcohol (24/1) and 50 ul of 2×STEB buffer (40% (w/v) sucrose, 100 mM Tris-HCL (pH 8), 1 mM EDTA, 0.5 mg/ml bromophenol blue) followed by mixing and centrifugation at 13,000 rpm for 1 minute. 20 ul of sample (lower aqueous phase) along with 0.5 ug of relaxed pHOT-1 control DNA (TopoGEN, Inc. TG2035-2; Lane 1) were resolved over 1% (w/v) agarose gel electrophoresis at 80V for 4 hours. The gel was stained with ethidium bromide for 15 minutes followed by de-staining in distilled water for 10 minutes. Gels were exposed and images acquired using the iBrightFL1000 gel documentation system (Invitrogen).

Phenotypic Profiling Using PubChem Data

Structural and bioactivity data was downloaded from PubChem using the NCBI FTP site (ftp://ftp.ncbi.nlm.nih.gov/pubchem/) on May 25, 2016. SDF files were batch processed with structural and physical chemical properties generated using JChem as described above. Prediction confidence scores were used to threshold compounds into each indicated phenotypic class, with enrichment in each of 250,873 PubChem bioactivity assays having at least one annotated 'active' and 'inactive' compound. These activity designations were included at the discretion of PubChem, and were not modified, thresholded, added, or removed. P-values for association between compounds assigned to a phenotypic class and a given bioactivity were assigned using Fisher's Exact test followed by a Bonferonni correction for the 250,873 potential comparisons.

REFERENCES

1. Swinney, D. C. & Anthony, J. How were new medicines discovered? *Nat Rev Drug Discov* 10, 507-519 (2011).
2. Hughes, J. P., Rees, S. S., Kalindjian, S. B. & Philpott, K. L. Principles of early drug discovery. *British Journal of Pharmacology* (2011). doi:10.1111/j.1476-5381.2010.01127.x
3. Paul, S. M. et al. How to improve R&D productivity: the pharmaceutical industry's grand challenge. *Nat Rev Drug Discov* 9, 203-214 (2010).
4. Zheng, W., Thorne, N. & McKew, J. C. Phenotypic screens as a renewed approach for drug discovery. *Drug Discov Today* 18, 1067-1073 (2013).
5. Paull, K. D. et al. Display and analysis of patterns of differential activity of drugs against human tumor cell lines: Development of mean graph and COMPARE algorithm. *J. Natl. Cancer Inst.* (1989). doi:10.1093/jnci/81.14.1088
6. Adams, C. L. et al. Compound Classification Using Image-Based Cellular Phenotypes. in *Methods in Enzymology* (2006). doi:10.1016/S0076-6879(06)14024-0
7. Ljosa, V. et al. Comparison of methods for image-based profiling of cellular morphological responses to small-molecule treatment. *J Biomol. Screen.* (2013). doi: 10.1177/1087057113503553
8. Reisen, F. et al. Linking Phenotypes and Modes of Action Through High-Content Screen Fingerprints. *Assay Drug Dev. Technol.* (2015). doi:10.1089/adt.2015.656
9. Futamura, Y. et al. Morphobase, an encyclopedic cell morphology database, and its use for drug target identification. *Chem. Biol.* (2012). doi:10.1016/j.chembiol.2012.10.014
10. Sundaramurthy, V. et al. Integration of chemical and RNAi multiparametric profiles identifies triggers of intracellular mycobacterial killing. *Cell Host Microbe* (2013). doi:10.1016/j.chom.2013.01.008
11. Bray, M. A. et al. Cell Painting, a high-content image-based assay for morphological profiling using multiplexed fluorescent dyes. *Nat. Protoc.* (2016). doi:10.1038/nprot.2016.105
12. Bray, M. A. et al. A dataset of images and morphological profiles of 30 000 small-molecule treatments using the Cell Painting assay. *GigaScience* (2017). doi:10.1093/gigascience/giw014
13. Weinstein, J. N. et al. An information-intensive approach to the molecular pharmacology of cancer. *Science* (80-.). (1997). doi:10.1126/science.275.5298.343
14. Barretina, J. et al. The Cancer Cell Line Encyclopedia enables predictive modelling of anticancer drug sensitivity. *Nature* (2012). doi:10.1038/nature11003
15. Johannessen, C. M., Clemons, P. A. & Wagner, B. K. Integrating phenotypic small-molecule profiling and human genetics: The next phase in drug discovery. *Trends in Genetics* (2015). doi:10.1016/j.tig.2014.11.002
16. Giaever, G. et al. Functional profiling of the *Saccharomyces cerevisiae* genome. *Nature* 418, 387-391 (2002).
17. Giaever, G. et al. Chemogenomic profiling: identifying the functional interactions of small molecules in yeast. *Proc Natl Acad Sci USA* 101, 793-798 (2004).
18. Kwok, T. C. et al. A small-molecule screen in *C. elegans* yields a new calcium channel antagonist. *Nature* 441, 91-95 (2006).
19. Burns, A. R. et al. *Caenorhabditis elegans* is a useful model for anthelmintic discovery. *Nat Commun* 6, 7485 (2015).
20. Hillenmeyer, M. E. et al. The chemical genomic portrait of yeast: uncovering a phenotype for all genes. *Science* (80-.). 320, 362-365 (2008).
21. Mathew, M. D. et al. Using *C. elegans* Forward and Reverse Genetics to Identify New Compounds with Anthelmintic Activity. *PLoS Negl Trop Dis* 10, e0005058 (2016).
22. Yu, P. B. et al. Dorsomorphin inhibits BMP signals required for embryogenesis and iron metabolism. *Nat. Chem. Biol.* (2008). doi:10.1038/nchembio.2007.54
23. Yu, P. B. et al. BMP type I receptor inhibition reduces heterotopic ossification. *Nat. Med.* (2008). doi:10.1038/nm.1888
24. North, T. E. et al. Prostaglandin E2 regulates vertebrate haematopoietic stem cell homeostasis. *Nature* (2007). doi:10.1038/nature05883
25. Peal, D. S., Peterson, R. T. & Milan, D. Small molecule screening in zebrafish. *Journal of Cardiovascular Translational Research* (2010). doi:10.1007/s12265-010-9212-8
26. Griffin, A. et al. Clemizole and modulators of serotonin signalling suppress seizures in Dravet syndrome. *Brain* 140, 669-683 (2017).
27. Rihel, J. & Schier, A. F. Behavioral screening for neuroactive drugs in zebrafish. *Dev Neurobiol* 72, 373-385 (2012).
28. Haggard, D. E., Noyes, P. D., Waters, K. M. & Tanguay, R. L. Transcriptomic and phenotypic profiling in developing zebrafish exposed to thyroid hormone receptor agonists. *Reprod. Toxicol.* (2018). doi:10.1016/j.reprotox.2018.02.006
29. Wallace, I. M. et al. Compound prioritization methods increase rates of chemical probe discovery in model organisms. *Chem Biol* 18, 1273-1283 (2011).
30. Kim, S. et al. PubChem Substance and Compound databases. *Nucleic Acids Res* 44, D1202-13 (2016).
31. Wang, Y. et al. PubChem BioAssay: 2014 update. *Nucleic Acids Res* 42, D1075-82 (2014).
32. Hann, M. M. & Keser, G. M. Finding the sweet spot: The role of nature and nurture in medicinal chemistry. Nature Reviews Drug Discovery (2012). doi:10.1038/nrd3701
33. Mason, P. A. & Sturman, G. Some pharmacological properties of piperazine. *Br J Pharmacol* 44, 169-176 (1972).
34. Viswanadhan, V. N., Ghose, A. K., Revankar, G. R. & Robins, R. K. Atomic physicochemical parameters for three dimensional structure directed quantitative structure-activity relationships. 4. Additional parameters for hydrophobic and dispersive interactions and their application for an automated superposition of certain. *J Chem Inf Comput Sci* 29, 163-172 (1989).
35. Shelat, A. A. & Guy, R. K. The interdependence between screening methods and screening libraries. *Curr Opin Chem Biol* 11, 244-251 (2007).
36. Kutchukian, P. S. et al. Chemistry informer libraries: a chemoinformatics enabled approach to evaluate and advance synthetic methods. *Chem Sci* 7, 2604-2613 (2016).
37. Svetnik, V. et al. Random forest: a classification and regression tool for compound classification and QSAR modeling. *J Chem Inf Comput Sci* 43, 1947-1958 (2003).
38. Breiman, L. Random Forests. *Mach. Learn.* 45, 5-32 (2001).
39. Riniker, S., Wang, Y., Jenkins, J. L. & Landrum, G. A. Using information from historical high-throughput screens to predict active compounds. *J Chem Inf Model* 54, 1880-1891 (2014).
40. Kutchukian, P. S. et al. Iterative Focused Screening with Biological Fingerprints Identifies Selective Asc-1 Inhibitors Distinct from Traditional High Throughput Screening. *ACS Chem Biol* 12, 519-527 (2017).
41. Sun, D. et al. Efficient identification of novel leads by dynamic focused screening: PDK1 case stud. *Comb Chem High Throughput Screen* 13, 16-26 (2010).
42. Wassermann, A. M. et al. Efficient search of chemical space: navigating from fragments to structurally diverse chemotypes. *J Med Chem* 56, 8879-8891 (2013).
43. Paricharak, S., AP, I. J., Bender, A. & Nigsch, F. Analysis of Iterative Screening with Stepwise Compound Selection Based on Novartis In-house HTS Data. *ACS Chem Biol* 11, 1255-1264 (2016).
44. Sheridan, R. P., Feuston, B. P., Maiorov, V. N. & Kearsley, S. K. Similarity to molecules in the training set is a good discriminator for prediction accuracy in QSAR. *J Chem Inf Comput Sci* 44, 1912-1928 (2004).
45. Chung, A. C. & Cooney, A. J. The varied roles of nuclear receptors during vertebrate embryonic development. *Nucl Recept Signal* 1, e007 (2003).
46. Polyakov, V. R., Moorcroft, N. D. & Drawid, A. Enrichment analysis for discovering biological associations in phenotypic screens. *J Chem Inf Model* 54, 377-386 (2014).
47. Mervin, L. H. et al. Understanding Cytotoxicity and Cytostaticity in a High-Throughput Screening Collection. *ACS Chem Biol* 11, 3007-3023 (2016).
48. Wassermann, A. M., Lounkine, E., Davies, J. W., Glick, M. & Camargo, L. M. The opportunities of mining historical and collective data in drug discovery. *Drug Discov Today* 20, 422-434 (2015).
49. Bornot, A., Blackett, C., Engkvist, O., Murray, C. & Bendtsen, C. The Role of Historical Bioactivity Data in the Deconvolution of Phenotypic Screens. *J Biomol Screen* 19, 696-706 (2014).
50. Musso, G. et al. Novel cardiovascular gene functions revealed via systematic phenotype prediction in zebrafish. *Development* 141, 224-235 (2014).
51. Pinho, B. R. et al. How mitochondrial dysfunction affects zebrafish development and cardiovascular function: an in vivo model for testing mitochondria-targeted drugs. *Br J Pharmacol* 169, 1072-1090 (2013).
52. Mendelsohn, B. A., Kassebaum, B. L. & Gitlin, J. D. The zebrafish embryo as a dynamic model of anoxia tolerance. *Dev Dyn* 237, 1780-1788 (2008).
53. Aitken, J. F., van Heusden, G. P., Temkin, M. & Dowhan, W. The gene encoding the phosphatidylinositol transfer protein is essential for cell growth. *J Biol Chem* 265, 4711-4717 (1990).
54. Nica, G., Herzog, W., Sonntag, C. & Hammerschmidt, M. Zebrafish pit1 mutants lack three pituitary cell types and develop severe dwarfism. *Mol Endocrinol* 18, 1196-1209 (2004).
55. Keiser, M. J. et al. Relating protein pharmacology by ligand chemistry. *Nat Biotechnol* 25, 197-206 (2007).
56. Mousley, C. J., Davison, J. M. & Bankaitis, V. A. Sec14 like PITPs couple lipid metabolism with phosphoinositide synthesis to regulate Golgi functionality. *Subcell Biochem* 59, 271-287 (2012).
57. Bankaitis, V. A., Mousley, C. J. & Schaaf, G. The Sec14 superfamily and mechanisms for crosstalk between lipid metabolism and lipid signaling. *Trends Biochem Sci* 35, 150-160 (2010).
58. Mousley, C. J., Tyeryar, K. R., Vincent-Pope, P. & Bankaitis, V. A. The Sec14-superfamily and the regulatory interface between phospholipid metabolism and membrane trafficking. *Biochim Biophys Acta* 1771, 727-736 (2007).
59. Rudge, S. A., Zhou, C. & Engebrecht, J. Differential regulation of *Saccharomyces cerevisiae* phospholipase D in sporulation and Sec14-independent secretion. *Genetics* 160, 1353-1361 (2002).
60. Recanatini, M., Poluzzi, E., Masetti, M., Cavalli, A. & De Ponti, F. QT prolongation through hERG K(+) channel blockade: current knowledge and strategies for the early prediction during drug development. *Med Res Rev* 25, 133-166 (2005).
61. Raschi, E., Ceccarini, L., De Ponti, F. & Recanatini, M. hERG-related drug toxicity and models for predicting hERG liability and QT prolongation. *Expert Opin Drug Metab Toxicol* 5, 1005-1021 (2009).
62. Foley, M. & Tilley, L. Quinoline antimalarials: mechanisms of action and resistance and prospects for new agents. *Pharmacol Ther* 79, 55-87 (1998).
63. RohitKumar, H. G., Asha, K. R., KiranKumar, H. N., Inamdar, L. S. & Rao, G. M. Cell Cycle Arrest and Induction of Apoptosis in Colon Adenocarcinoma Cells by a DNA Intercalative Quinoline Derivative, 4-Morpholinopyrimido [4',5':4,5] Selenolo (2,3-b) Quinoline. *Nucleosides Nucleotides Nucleic Acids* 34, 525-543 (2015).
64. RohitKumar, H. G., Asha, K. R., Raghavan, S. C. & Advi Rao, G. M. DNA intercalative 4-butylaminopyrimido[4',5':4,5]thieno(2,3-b)quinoline induces cell cycle arrest and apoptosis in leukemia cells. Cancer Chemother *Pharmacol* 75, 1121-1133 (2015).
65. O'Boyle, N. M. et al. Open Babel: An open chemical toolbox. *J Cheminform* 3, 33 (2011).
66. Enright, A. J., Van Dongen, S. & Ouzounis, C. A. An efficient algorithm for large-scale detection of protein families. *Nucleic Acids Res* 30, 1575-1584 (2002).
67. Shannon, P. et al. Cytoscape: a software environment for integrated models of biomolecular interaction networks. *Genome Res* 13, 2498-2504 (2003).
68. Sing, T., Sander, O., Beerenwinkel, N. & Lengauer, T. ROCR: visualizing classifier performance in R. *Bioinformatics* 21, 3940-3941 (2005).

69. Subramanian, A. et al. Gene set enrichment analysis: a knowledge-based approach for interpreting genome-wide expression profiles. *Proc Natl Acad Sci USA* 102, 15545-15550 (2005).

70. Smith, A. M. et al. Highly-multiplexed barcode sequencing: an efficient method for parallel analysis of pooled samples. *Nucleic Acids Res* 38, e142 (2010).

71. Pierce, S. E. et al. A unique and universal molecular barcode array. *Nat Methods* 3, 601-603 (2006).

72. Stackley, K. D., Beeson, C. C., Rahn, J. J. & Chan, S. S. Bioenergetic profiling of zebrafish embryonic development. *PLoS One* 6, e25652 (2011).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A method for inhibiting cell proliferation, cell growth, and/or cell survival comprising:

administering a compound of Formula I, derivatives, isomers, or pharmaceutically acceptable salts thereof, at a dosage effective to inhibit cell proliferation, cell growth, and/or survival of the cells, wherein Formula I is:

(I)

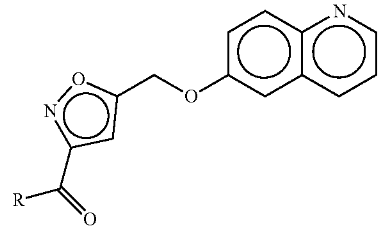

wherein R is selected from the group consisting of:

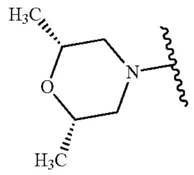,

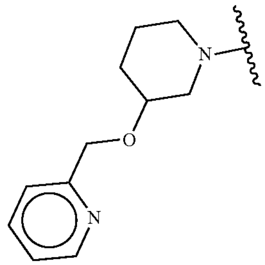,

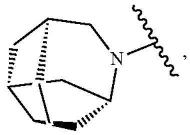,

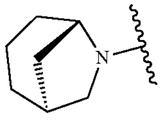,

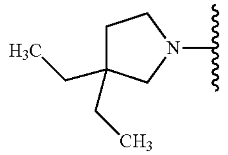,

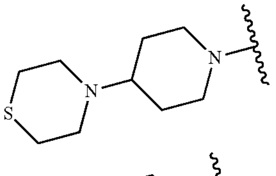,

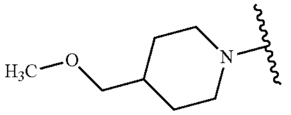, and $NH_2$.

2. The method of claim 1, wherein the cells are in a subject.

3. The method of claim 2, wherein the subject is a human.

4. The method of claim 3, wherein the subject has been diagnosed with cancer, and the cells comprise cancer cells.

5. The method of claim 1, wherein the compound comprises

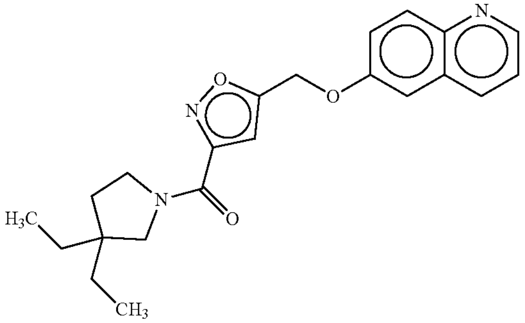.

6. The method of claim 4, wherein the cancer comprises bone cancer and the cells comprise-bone cancer cells.

7. A method of treating a disease or condition characterized by increased cell proliferation and/or cell growth in a subject in need thereof, the method comprising:

administering to the subject an effective amount of a compound of Formula I, derivatives, isomers, or pharmaceutically acceptable salts thereof, wherein Formula I is:

(I)

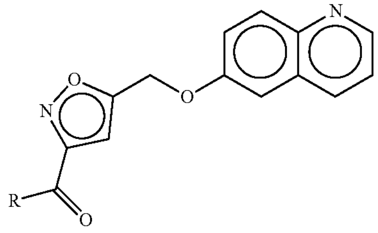

wherein R is selected from the group consisting of:

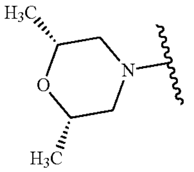,

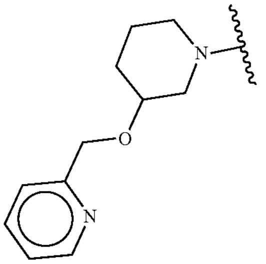,

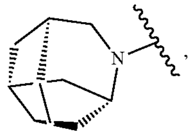,

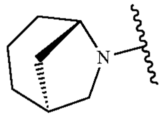,

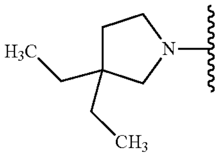,

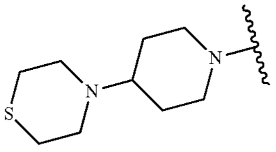,

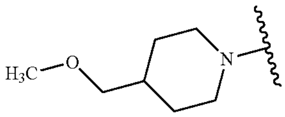, and $NH_2$.

8. The method of claim 7, wherein the disease or condition comprises cancer, and the subject in need thereof is a human.

9. The method of claim 8, wherein the cancer comprises bone cancer.

10. The method of claim 7, wherein the compound comprises

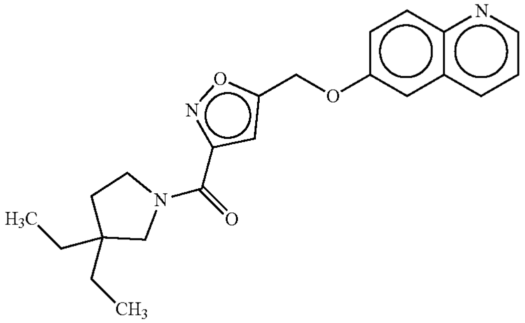.

11. A method of reversibly decreasing the activity of phospholipase D and/or reducing the amount of phosphatidic acid in a subject in need thereof, the method comprising:

administering to the subject a compound of Formula I, derivatives, isomers, or pharmaceutically acceptable salts thereof, at a dosage effective to reversibly decrease the activity of phospholipase D and/or reduce the amount of phosphatidic acid, wherein Formula I is:

(I)

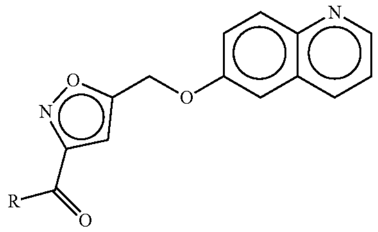

wherein R is selected from the group consisting of:

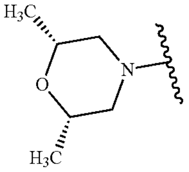,

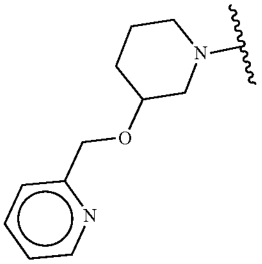,

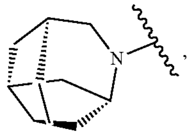,

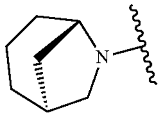,

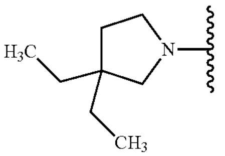,

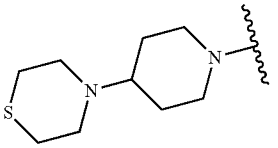,

-continued

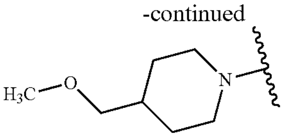

, and $NH_2$.

12. The method of claim 11, wherein the subject comprises a mammalian subject.

13. The method of claim 11, wherein the subject is a human.

14. The method of claim 13, wherein the subject has been diagnosed with Alzheimer's disease or is at risk of developing Alzheimer's disease.

15. The method of claim 11, wherein the compound comprises

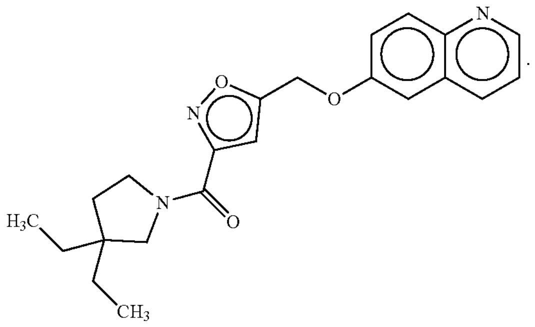

16. A method of increasing the activity of phospholipase A and/or phospholipase C in a population of cells, the method comprising:

administering to the population of cells a compound of Formula I, derivatives, isomers, or pharmaceutically acceptable salts thereof, at a dosage effective to increase the activity of phospholipase A and/or phospholipase C, wherein Formula I is:

(I)

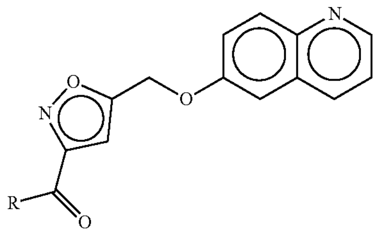

wherein R is selected from the group consisting of:

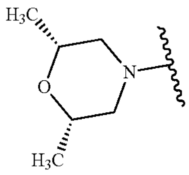

,

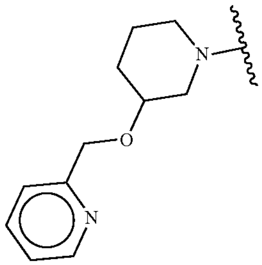

,

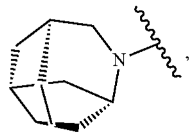

,

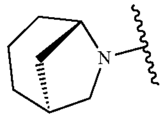

,

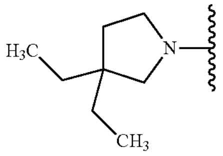

,

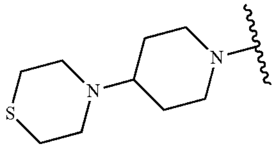

,

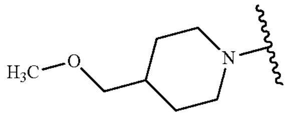

, and $NH_2$.

* * * * *